(12) United States Patent
Lund et al.

(10) Patent No.: US 8,460,169 B2
(45) Date of Patent: Jun. 11, 2013

(54) ADJUSTABLE TENSION INCONTINENCE SLING ASSEMBLIES

(75) Inventors: Robert E. Lund, St. Michael, MN (US); Jason Westrum Ogdahl, Minneapolis, MN (US); Jessica Lynn Roll, Minnetonka, MN (US); Kelly Ann Chapman, Altadena, CA (US)

(73) Assignee: AMS Research Corporation, Minnetonka, MN (US)

( * ) Notice: Subject to any disclaimer, the term of this patent is extended or adjusted under 35 U.S.C. 154(b) by 450 days.

(21) Appl. No.: 12/305,874

(22) PCT Filed: Jun. 22, 2007

(86) PCT No.: PCT/US2007/014553
§ 371 (c)(1),
(2), (4) Date: Jun. 30, 2010

(87) PCT Pub. No.: WO2007/149555
PCT Pub. Date: Dec. 27, 2007

(65) Prior Publication Data
US 2010/0261950 A1    Oct. 14, 2010

Related U.S. Application Data

(60) Provisional application No. 60/805,544, filed on Jun. 22, 2006, provisional application No. 60/806,664, filed on Jul. 6, 2006.

(51) Int. Cl.
*A61F 2/02* (2006.01)
*A61F 2/00* (2006.01)

(52) U.S. Cl.
USPC .............................................. 600/30; 600/29

(58) Field of Classification Search
USPC ................... 600/30, 29, 31, 37; 128/DIG. 25
See application file for complete search history.

(56) References Cited

U.S. PATENT DOCUMENTS

| 2,738,790 | A | 3/1956 | Todt et al. |
| 3,124,136 | A | 3/1964 | Usher |

(Continued)

FOREIGN PATENT DOCUMENTS

| AU | 2002241673 | 11/2005 |
| CA | 2404459 | 8/2005 |

(Continued)

OTHER PUBLICATIONS

"We're staying ahead of the curve" Introducing the IVS Tunneller Device for Tension Free Procedures, Tyco Healthcare, 3 pages (2002).

(Continued)

*Primary Examiner* — Christine Matthews
*Assistant Examiner* — Sunita Reddy
(74) *Attorney, Agent, or Firm* — Gregory L. Koeller; Kimberly K. Baxter

(57) ABSTRACT

Systems for providing support to body tissue to alleviate incontinence are disclosed that comprise an elongated incontinence sling having a central support portion adapted to be positioned to support any one of the urethra or anus and first and second sling end portions extending from the central support portion through body tissue and a tension adjustment mechanism acting on or within one or both of the sling end portions. The sling tension adjustment mechanism is attached to and extends through an adjustment spacing between sling intermediate ends within at least one sling end portion. The adjustment spacing is lengthened to decrease sling tension and shortened to increase sling tension.

10 Claims, 31 Drawing Sheets

U.S. PATENT DOCUMENTS

| | | |
|---|---|---|
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Velaquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |

| Patent No. | Date | Inventor |
|---|---|---|
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,407 B2 | 6/2007 | Kammerer et al. |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosley et al. |
| 7,789,821 B2 | 9/2010 | Browning |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0069469 A1* | 4/2003 | Li ..................... 600/30 |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0249396 A1* | 12/2004 | Lund et al. ..................... 606/151 |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0028828 A1 | 7/2006 | Cox et al. |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0241748 A1* | 10/2006 | Lee et al. ..................... 623/2.37 |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0167518 A1* | 7/2008 | Burton et al. ..................... 600/31 |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |

| | | | |
|---|---|---|---|
| EP | 0470308 A1 | 2/1992 | |
| EP | 0650703 A1 | 6/1994 | |
| EP | 0643945 A2 | 7/1994 | |
| EP | 0632999 A1 | 1/1995 | |
| EP | 1093758 A1 | 4/2001 | |
| EP | 1060714 A3 | 9/2002 | |
| EP | 1342450 B1 | 9/2003 | |
| FR | 2787990 A1 | 7/2000 | |
| FR | 2852813 A1 | 1/2004 | |
| GB | 2268690 A | 1/1994 | |
| GB | 2353220 A | 10/2000 | |
| IT | 1299162 | 4/1998 | |
| SU | 1225547 A1 | 4/1986 | |
| SU | 1342486 A | 10/1987 | |
| WO | WO9317635 A1 | 9/1993 | |
| WO | WO9319678 A2 | 10/1993 | |
| WO | WO9511631 A1 | 5/1995 | |
| WO | WO9525469 A1 | 9/1995 | |
| WO | WO9716121 A1 | 5/1997 | |
| WO | WO9730638 A1 | 8/1997 | |
| WO | WO9747244 A1 | 12/1997 | |
| WO | WO9819606 A1 | 5/1998 | |
| WO | WO9835606 A1 | 8/1998 | |
| WO | WO9835616 A1 | 8/1998 | |
| WO | WO9835632 A1 | 8/1998 | |
| WO | WO9842261 A1 | 10/1998 | |
| WO | WO9853746 A1 | 12/1998 | |
| WO | WO9916381 A1 | 4/1999 | |
| WO | WO9937217 A1 | 7/1999 | |
| WO | WO9952450 A1 | 10/1999 | |
| WO | WO9953844 A1 | 10/1999 | |
| WO | WO9959477 A1 | 11/1999 | |
| WO | WO0064370 A1 | 2/2000 | |
| WO | WO0013601 A1 | 3/2000 | |
| WO | WO0018319 A1 | 4/2000 | |
| WO | WO0027304 A1 | 5/2000 | |
| WO | WO0040158 A2 | 7/2000 | |
| WO | WO0057812 A1 | 10/2000 | |
| WO | WO0066030 A1 | 11/2000 | |
| WO | WO0074594 A1 | 12/2000 | |
| WO | WO0074613 A1 | 12/2000 | |
| WO | WO0074633 A2 | 12/2000 | |
| WO | WO0106951 A1 | 2/2001 | |
| WO | WO0126581 A1 | 4/2001 | |
| WO | WO0139670 A1 | 6/2001 | |
| WO | WO0145588 A1 | 6/2001 | |
| WO | WO0145589 A1 | 6/2001 | |
| WO | WO0156499 A1 | 8/2001 | |
| WO | WO0228312 A1 | 4/2002 | |
| WO | WO0228315 A2 | 4/2002 | |
| WO | WO0230293 A1 | 4/2002 | |
| WO | WO0232284 A2 | 4/2002 | |
| WO | WO0234124 A2 | 5/2002 | |
| WO | WO0238079 A2 | 5/2002 | |
| WO | WO0239890 A2 | 5/2002 | |
| WO | WO02058563 A1 | 8/2002 | |
| WO | WO02062237 A1 | 8/2002 | |
| WO | WO02069781 | 9/2002 | |
| WO | WO02071953 A2 | 9/2002 | |
| WO | WO02078552 A1 | 10/2002 | |
| WO | WO02089704 A2 | 11/2002 | |
| WO | WO03017848 A1 | 3/2003 | |
| WO | WO03003778 A1 | 4/2003 | |
| WO | WO03028585 A2 | 4/2003 | |
| WO | WO03037215 A2 | 5/2003 | |
| WO | WO03041613 A1 | 5/2003 | |
| WO | WO03047435 A1 | 6/2003 | |
| WO | WO03068107 A1 | 8/2003 | |
| WO | WO03075792 A1 | 9/2003 | |
| WO | WO03092546 A2 | 11/2003 | |
| WO | WO03096929 A1 | 11/2003 | |
| WO | WO2004012626 A1 | 2/2004 | |
| WO | WO2004016196 A2 | 2/2004 | |
| WO | WO2004017862 A2 | 3/2004 | |
| WO | WO2004034912 A1 | 4/2004 | |
| WO | WO2005037132 A2 | 4/2005 | |
| WO | WO2005079702 A1 | 9/2005 | |
| WO | WO2005122954 A1 | 12/2005 | |
| WO | WO2006015031 A2 | 2/2006 | |
| WO | WO2006108145 A1 | 10/2006 | |
| WO | WO2007011341 A1 | 1/2007 | |
| WO | WO2007014241 A1 | 2/2007 | |
| WO | WO2007016083 A1 | 2/2007 | |
| WO | WO2007027592 A2 | 3/2007 | |
| WO | WO2007059199 A2 | 5/2007 | |
| WO | WO2007081955 A1 | 7/2007 | |
| WO | WO2007097994 | 8/2007 | |
| WO | WO2007137226 A2 | 11/2007 | |
| WO | WO2007146784 A2 | 12/2007 | |
| WO | WO2007149348 A2 | 12/2007 | |
| WO | WO2007149555 A2 | 12/2007 | |
| WO | WO2008057261 A2 | 5/2008 | |
| WO | WO2008124056 A1 | 10/2008 | |
| WO | WO2009005714 A2 | 1/2009 | |
| WO | WO2009017680 A2 | 2/2009 | |

OTHER PUBLICATIONS

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology. V. 44, pp. 398-411, (1948).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology. vol. 144, pp. 319-323 (Aug. 1990).

Asmussen, M. et.al., Simultaneous Urethro-Cystometry With a New Technique, Scand J Urol Nephrol 10, p. 7-11 (1976).

Beck, Peter R. et al., Treatment of Urinary Stress Incontinence With Anterior Colporrhaphy, Obstetrics and Gynecology, vol. 59 (No. 3), pp. 269-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).

Blaivas, Jerry et al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blaivas, Jerry, Commentary: Pubovaginal Sling Procedure, Experience with Pubovaginal Slings, pp. 93-101 (1990).

Boyles, Sarah Hamilton et al., Procedures for Urinary Incontinence in the United States, 1979-1997, Am J Obstet Gynecol, vol. 189, n. 1, pp. 70-75 (Jul. 2003).

Bryans, Fred E., Marlex Gauze Hammock Sling Operation With Cooper's Ligament Attachment in the Management of Recurrent Urinary Stress Incontinence, American Journal of Obstetrics and Gynecology. vol. 133, pp. 292-294 (Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Capio™ CL—Transvaginal Suture Capturing Device—Transvaginal Suture Fixation to Cooper's Ligament for Sling Procedures, Boston Scientific, Microvasive®, 8 pages, (2002).

Cervigni, Mauro et al., The Use of Synthetics in the Treatment of Pelvic Organ Prolapse, Voiding Dysfunction and Female Urology, vol. 11, pp. 429-435 (2001).

Choe, Jong M. et al., Gore-Tex Patch Sling: 7 Years Later, Urology, vol. 54, pp. 641-646 (1999).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Das, Sakti et al., Laparoscopic Colpo-Suspension, The Journal of Urology, vol. 154, pp. 1119-1121 (Sep. 1995).

Debodinance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.

Decter, Ross M., Use of the Fascial Sling for Neurogenic Incontinence: Lessons Learned, The Journal of Urology, vol. 150, pp. 683-686 (Aug. 1993).

DeLancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50 (1990).

Falconer, C. et al., Clinical Outcome and Changes in Connective Tissue Metabolism After Intravaginal Slingplasty in Stress Incontinence Women, International Urogynecology Journal, pp. 133-137 (1966).

Falconer, C. et al., Influence of Different Sling Materials of Connective Tissue Metabolism in Stress Urinary Incontinent Women, International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce With Marlex Mesh for the Treatment of Cystoceles, International Urogynecology Journal, vol. 9, pp. 200-204 (1998).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138 (Sep. 1987).

Guner, et al., Transvaginal Sacrospinous Colpopexy for Marked Uterovaginal and Vault Prolapse, Inter J of Gynec & Obstetrics, vol. 74, pp. 165-170 (2001).

Gynecare TVT Tension-Free Support for Incontinence, The tension-free solution to female Incontinence, Gynecare Worldwide,6 pages, (2002).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Heit, Michael et al., Predicting Treatment Choice for Patients With Pelvic Organ Prolapse, Obstetrics & Gynecology, vol. 101, n. 6, pp. 1279-1284 (Jun. 2003).

Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).

Hodgkinson, C. Paul et.al., Urinary Stress Incontinence in the Female, Department of Gynecology and Obstetrics, Henry Ford Hospital, vol. 10, No. 5, p. 493-499, (Nov. 1957).

Holschneider, C. H., et al., The Modified Pereyra Procedure in Recurrent Stress Urinary incontinence: A 15-year Review, Obstetrics & Gynecology, vol. 83, No. 4, pp. 573-578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).

Ingelman-Sunberg, A. et al., Surgical Treatment of Female Urinary Stress Incontinence, Contr. Gynec. Obstet., vol. 10, pp. 51-69 (1983).

IVS Tunneller—A Universal instrument for anterior and posterior intra-vaginal tape placement, Tyco Healthcare, 4 pages (Aug. 2002).

IVS Tunneller—ein universelles Instrument fur die Intra Vaginal Schlingenplastik, Tyco Healthcare, 4 pages (2001).

Jeffcoate. T.N.A. et al., The Results of the Aldridge Sling Operation for Stress Incontinence, Journal of Obstetrics and Gynaecology, pp. 36-39 (1956).

Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).

Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

Karram, Mickey et al., Patch Procedure: Modified Transvaginal Fascia Lata Sling for Recurrent for Severe Stress Urinary Incontinence, vol. 75, pp. 461-463 (Mar. 1990).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Kersey, J., The Gauze Hammock Sling Operation in the Treatment of Stress Incontintence, British Journal of Obstetrics and Gynaecology. vol. 90, pp. 945-949 (Oct. 1983).

Klutke, Carl et al., The Anatomy of Stress Incontinence: Magentic Resonance Imaging of the Female Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Klutke, John M.D. et al, The promise of tension-free vaginal tape for female SUI, Contemporary Urology, 7 pages (Oct. 2000).

Korda, A. et al., Experience With Silastic Slings for Female Urinary Incontience, Aust NZ J. Obstet Gynaecol, vol. 29, pp. 150-154 (May 1989).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Kovac, Stephen Robert, M.D., Cirriculum Vitae, pp. 1-33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).

Lichtenstein, Irving L. et al, The Tension Free Hernioplasty, The American Journal of Surgery, vol. 157 pp. 188-193 (Feb. 1989).

Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).

Luber, Karl M. et al., The Demographics of Pelvic Floor Disorders; Current Observations and Future Projections, Am J Obstet Gynecol, vol. 184, n. 7, pp. 1496-1503 (Jun. 2001).

Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).

Marchionni, Mauro et al., True Incidence of Vaginal Vault Prolapse—Thirteen Years of Experience, Journal of Reproductive Medicine, vol. 44, n. 8, pp. 679-684 (Aug. 199).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics. vol. 88, pp. 509-518 (1949).

McGuire, Edward J. et al., Pubovaginal Sling Procedure for Stress Incontinence, The Journal of Urology, vol. 119, pp. 82-84 (Jan. 1978).

McGuire, Edward J. et al., Abdominal Procedures for Stress Incontinence, Urologic Clinics of North America, pp. 285-290, vol. 12, No. 2 (May 1985).

McGuire, Edward J. et al., Experience With Pubovaginal Slings for Urinary Incontinence at the University of Michigan, Journal of Urology, vol. 138, pp. 90-93(1987).

McGuire, Edwared J. et al., Abdominal Fascial Slings, Slings, Raz Female Urology, p. 369-375 (1996).

McGuire™ Suture Buide, The McGuire™ Suture Guide, a single use instrument designed for the placement of a suburethral sling, Bard, 2 pages (2001).

McIndoe, G. A. et al., The Aldridge Sling Procedure in the Treatment of Urinary Stress Incontinence, Aust. N Z Journal of Obstet Gynecology, pp. 238-239 (Aug. 1987).

McKiel, Charles F. Jr., et al, Marshall-Marchetti Procedure Modification, vol. 96, pp. 737-739 (Nov. 1966).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Morley, George W. et al., Sacrospinous Ligament Fixations for Eversion of the Vagina, Am J Obstet Gyn, vol. 158, n. 4, pp. 872-881 (Apr. 1988).

Narik, G. et.al., A Simplified Sling Operation Suitable for Routine Use, Gynecological and Obstetrical Clinic, University of Vienna, vol. 84, No. 3, p. 400-405, (Aug. 1, 1962).

Natale, F. et al., Tension Free Cystocele Repair (TCR): Long-Term Follow-Up, International Urogynecology Journal, vol. 11, supp. 1, p. S51 (Oct. 2000).

Nichols, David H., The Mersilene Mesh Gauze-Hammock for Severe Urinary Stress Incontinence, Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Norris, Jeffrey P. et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Paraiso et al., Laparoscopic Surgery for Enterocele, Vaginal Apex Prolapse and Rectocele, Int. Urogynecol J, vol. 10, pp. 223-229 (1999).

Parra, R. O., et al, Experience With a Simplified Technique for the Treatment of Female Stress Urinary Incontinence, British Journal of Urology, pp. 615-617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

Petros, Peter E. Papa et al., An Anatomical Basis for Success and Failure of Female Incontinence Surgery, Scandinavian Journal of Neurourology and Urodynamics, Sup 153, pp. 55-60 (1993).

Petros, Peter E. Papa et al., An Analysis of Rapid Pad Testing and the History for the Diagnosis of Stress Incontinence, Acta Obstet Gynecol Scand, vol. 71, pp. 529-536 (1992).

Petros, Peter E. Papa et al., An Integral Therory of Female Urinary Incontinence, Acta Obstetricia et Gynecologica Scandinavica, vol. 69 Sup. 153, pp. 7-31 (1990).

Petros, Peter E. Papa et al., Bladder Instability in Women: A Premature Activation of the Micturition Reflex, Scandinavian Journal of Neurourology and Urodynamics, Sup 153, pp. 235-239 (1993).

Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).

Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).

Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).

Petros, Peter E. Papa et al., Medium-Term Follow-Up of the Intravaginal Slingplasty Operation Indicates Minimal Deterioration of Urinary Continence With Time, (3 pages) ( 1999).

Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).

Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).

Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).

Petros, Peter E. Papa et al., Part III: Surgical Principles Deriving From the Theory, Scandinavian Journal of Neurourology and Urodynamics. Sup 153, pp. 41-52 (1993).

Petros, Peter E. Papa et al., Part IV: Surgical Appliations of the Theory—Development of the Intravaginal Sling Pklasty (IVS) Procedure, Scandinavian Journal of Neurourology and Urodynamics. Sup 153, pp. 53-54 (1993).

Petros, Peter E. Papa et al., Pinch Test for Diagnosis of Stress Urinary Incontinence, Acta Obstet Gynecol Scand, vol. 69, Sup 153, pp. 33-35 (1990).

Petros, Peter E. Papa et al., Pregnancy Effects on the Intravaginal Sling Operation, Acta Obstet Gynecol Scand, vol. 69, Sup 153, pp. 77-79 (1990).

Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).

Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).

Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).

Petros, Peter E. Papa et al., The Free Graft Procedure for Cure of the Tethered Vagina Syndrome, Scandinavian Journal of Neurourology and Urodynamics, Sup 153, pp. 85-87(1993).

Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).

Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).

Petros, Peter E. Papa et al., The Intravaginal Slingplasty Operation, a Minimally Invasive Technique for Cure of Urinary Incontinence in the Female, Aust. NZ J Obstet Gynaecol, vol. 36, n. 4, pp. 453-461 (1996).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).

Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).

Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).

Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).

Petros, Peter E. Papa, Development of Generic Models for Ambulatory Vaginal Surgery—Preliminary Report,International Urogynecology Journal, pp. 20-27 (1998).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).

Petros, Peter E. Papa, Vault Prolapse II; Restoration of Dynamic Vaginal Supports by Infracoccygeal Sacropexy, An Axial Day-Case Vaginal Procedure, Int Urogynecol J, vol. 12, pp. 296-303 (2001).

Rackley, Raymond R. et al., Tension-Free Vaginal Tape and Percutaneous Vaginal Tape Sling Procedures, Techniques in Urology, vol. 7, No. 2, pp. 90-100 (2001).

Rackley, Raymond R. M.D., Synthetic Slings: Five Steps for Successful Placement, Urology Times, p. 46,48,49 (Jun. 2000).

Raz, Shlomo, et al., The Raz Bladder Neck Suspension Results in 206 Patients, The Journal of Urology, pp. 845-846 (1992).

Raz, Shlomo, Female Urology, pp. 80-86, 369-398, 435-442 (1996).

Raz, Shlomo, MD, Modified Bladder Neck Suspension for Female Stress Incontinence, Urology, vol. XVII, No. 1, pp. 82-85 (Jan. 1981).

Richardson, David A. et al., Delayed Reaction to the Dacron Buttress Used in Urethropexy, The Journal of Reproductive Medicine, pp. 689-692, vol. 29, No. 9 (Sep. 1984).

Richter, K., Massive Eversion of the Vagina: Pathogenesis, Diagnosis and Therapy of the "True" Prolapse of the Vaginal Stump, Clin obstet gynecol, vol. 25, pp. 897-912 (1982).

Ridley, John H., Appraisal of the Goebell-Frangenheim-Stoeckel Sling Procedure, American Journal Obst & Gynec., vol. 95, No. 5, pp. 741-721 (Jul. 1, 1986).

Roberts, Henry, M.D., Cystourethrography in Women, Deptment of Obstetrics and Gynaecology, University of Liverpool, May 1952, vol. XXXV, No. 293, pp. 253-259.

Sabre™ Bioabsorbable Sling, Generation Now, Mentor, 4 pages (May 2002).

Sabre™ Surgical Procedure, Mentor, 6 pages (Aug. 2002).

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Seim, Arnfinn et al., A Study of Female Urinary Incontinence in General Practice—Demography, Medical History, and Clinical Findings, Scand J Urol Nephrol, vol. 30, pp. 465-472 (1996).

Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).

Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).

Stamey, Thomas A., M.D., Endoscopic Suspension of the Vesical Neck for Urinary Incontinence in Females, Ann. Surgery, vol. 192 No. 4, pp. 465-471 (Oct. 1980).

Stanton, Stuart L. Suprapubic Approaches for Stress Incontinence in Women, Journal of American Geriatrics Society, vol. 38, No. 3, pp. 348-351 (Mar. 1990).

Stanton, Stuart, Springer-Veglag, Surgery of Female Incontinence, pp. 105-113 (1986).

Staskin, David R. et al., The Gore-Tex Sling Procedure for Female Sphincteric Incontinence: Indications, Technique, and Results, World Journal of Urology, vol. 15, pp. 295-299 (1997).

Studdiford, William E., Transplantation of Abdominal Fascia for the Relief of Urinary Stress Incontinence, American Journal of Obstetrics and Gynecology, pp. 764-775 (1944).

Subak, Leslee L. et al., Cost of Pelvic Organ Prolapse Surgery in the United States, Obstetrics & Gynecology, vol. 98, n. 4, pp. 646-651 (Oct. 2001).

Sullivan, Eugene S. et al., Total Pelvic Mesh Repair a Ten-Year Experience, Dis. Colon Rectum, vol. 44, No. 6, pp. 857-863 (Jun. 2001).

Swift, S.E., et al., Case-Control Study of Etiologic Factors in the Development of Sever Pelvic Organ Prolapse, Int Urogynecol J, vol. 12, pp. 187-192 (2001).

T-Sling® (Totally Tension-free) Urinary Incontinence Procedure, Herniamesh, 2 pages (no date).

TVT Tension-free Vaginal Tape, Gynecare, Ethicon, Inc., 23 pages (1999).

Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).

Ulmsten, U. et al., An Ambulatory Surgical Procedure Under Local Anesthesia for Treatment of Female Urinary Incontinence, International Urogynecology Journal, vol. 7, pp. 81-86 (May 1996).

Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Ulmsten, Ulf et al., Different Biochemical Composition of Connective Tissue in Continent, Acta Obstet Gynecol Scand, pp. 455-457 (1987).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).

Ulmsten, Ulf et al., The Unstable Female Urethra, Am. J. Obstet. Gynecol., vol. 144 No. 1, pp. 93-97 (Sep. 1, 1982).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Villet, R., Réponse De R. Villet À L'Article De D. Dargent et al., Gynécolgie Obstétrique & Fertilité, vol. 31, p. 96 (2003).

Visco, Anthony G. et al., Vaginal Mesh Erosion After Abdominal Sacral Colpopexy, Am J Obstet Gynecol, vol. 184, n. 3, pp. 297-302 (297-302).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Weber, Anne M. et al., Anterior Vaginal Prolapse: Review of Anatomy and Techniques of Surgical Repair, Obstetrics and Gynecology. vol. 89, n. 2, pp. 311-318 (Feb. 1997).

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology, vol. XX, No. 4, pp. 408-411 (Oct. 1982).

Winters et al., Abdominal Sacral Colpopexy and Abdominal Enterocele Repair in the Management of Vaginal Vault Prolapse, Urology, vol. 56, supp. 6A, pp. 55-63 (2000).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et al., Pulsion Enterocele: Long-Term Results of an Abdominoperineal Technique, Obstetrics & Gynecology, vol. 55 No. 2, pp. 141-148 (Feb. 1980).

Zacharin, Robert, The Suspensory Mechanism of the Female Urethra, Journal of Anatomy, vol. 97, Part 3, pp. 423-427 (1963).

Zimmern, Phillippe E. et al., Four-Corner Bladder Neck Suspension, Vaginal Surgery fcr the Urologist, vol. 2, No. 1, pp. 29-36 (Apr. 1994).

Mouly, Patrick et al., Vaginal Reconstruction of a Complete Vaginal Prolapse: The Trans Obturator Repair, Journal of Urology, vol. 169, p. 183 (Apr. 2003).

Pourdeyhimi, B, Porosity of Surgical Mesh Fabrics: New Technology, J. Biomed. Mater. Res.: Applied Biomaterials, vol. 23, No. A1, pp. 145-152 (1989).

Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).

Petros, Papa PE et al., An Integral Theory and Its Method for the Diagnosis and Management of Female Urinary Incontinence, Scandinavian Journal of Urology and Nephrology, Supplement 153: p. 1 (1993).

Mentor Porges, Uratape, ICS/IUGA Symp, Jul. 2002.

\* cited by examiner

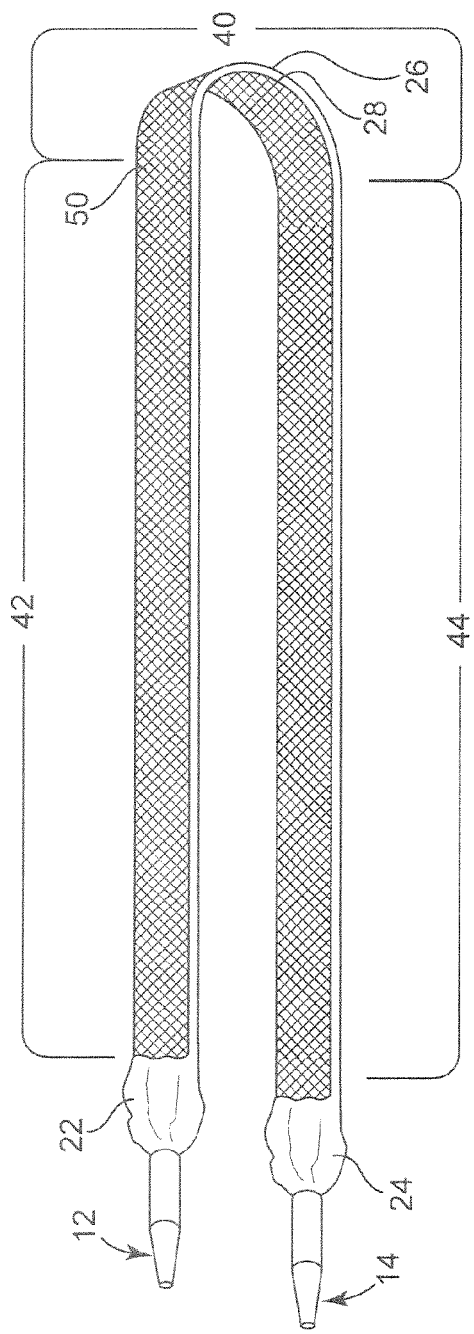
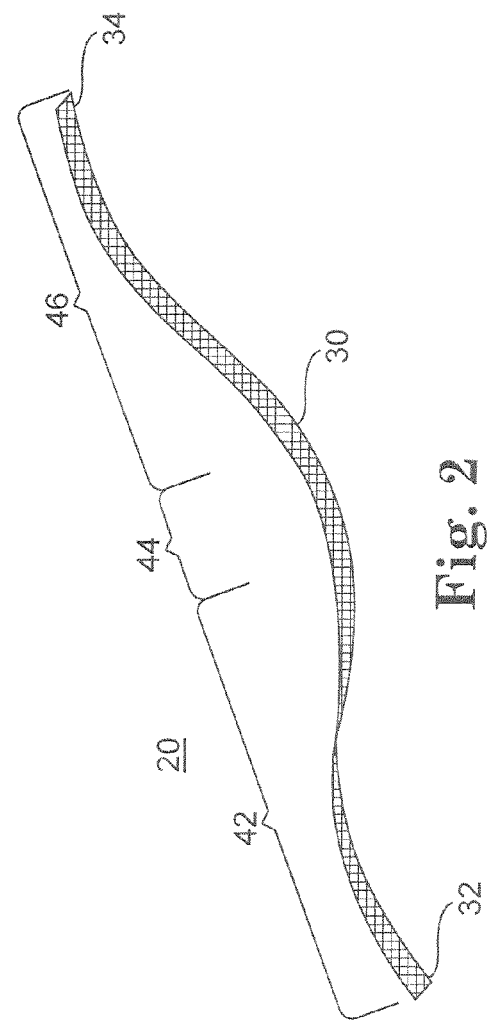

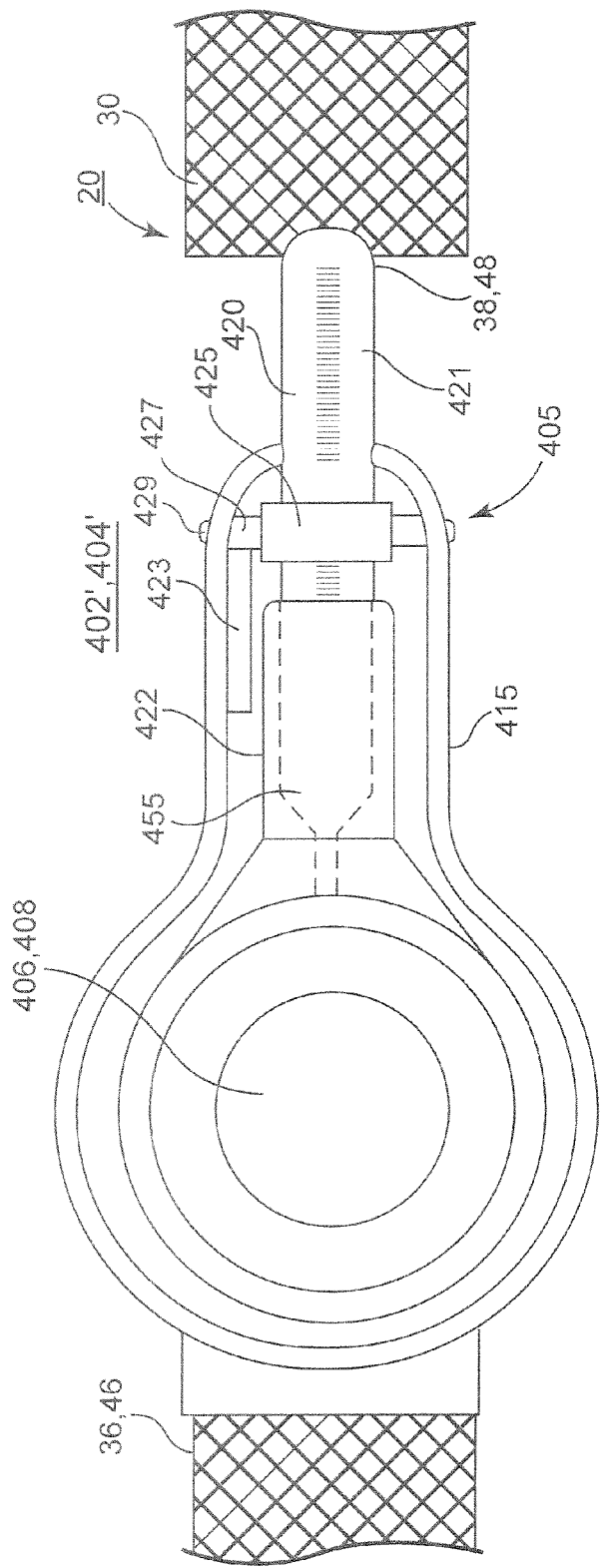
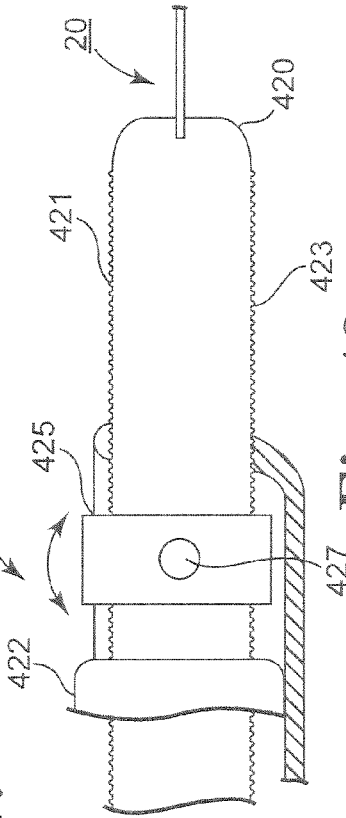

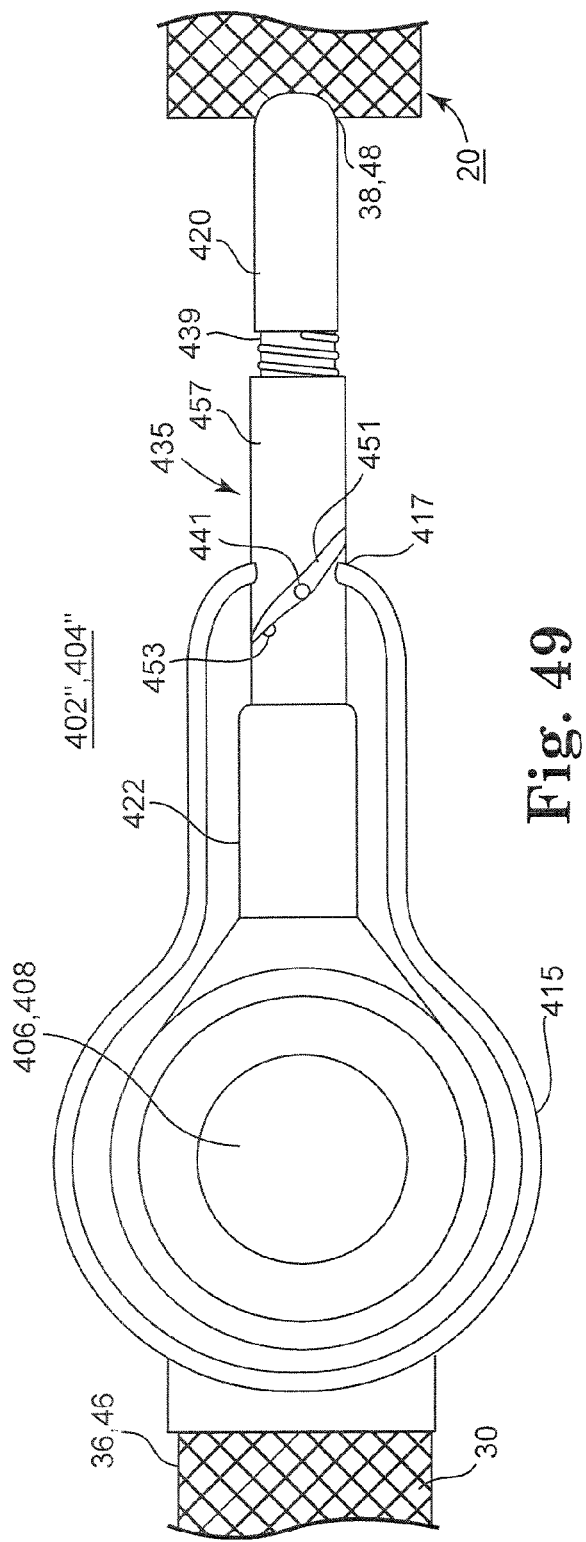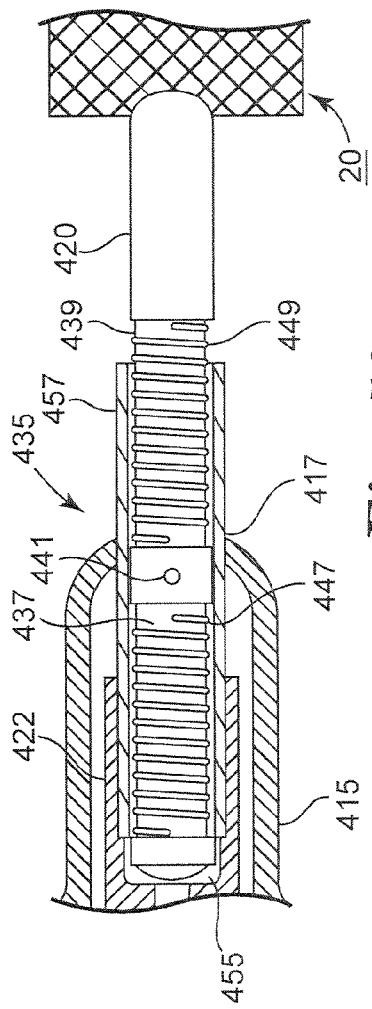

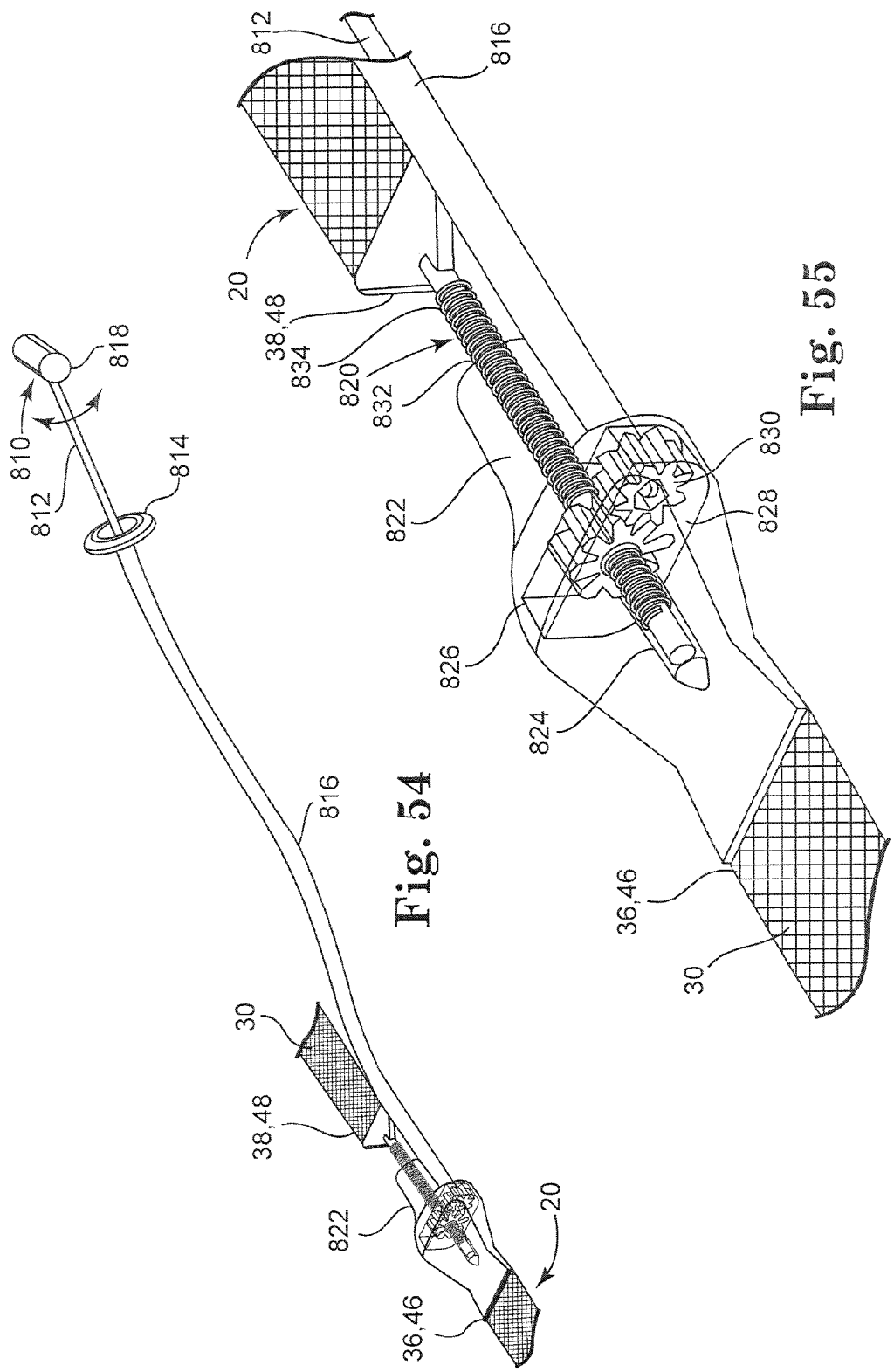

ADJUSTABLE TENSION INCONTINENCE SLING ASSEMBLIES

RELATED APPLICATIONS

This application claims priority to PCT Application No. PCT/US2007/014533 filed Jun. 22, 2007, which claims priority to U.S. Provisional Application Ser. No. 60/805,544 filed Jun. 22, 2006, and U.S. Provisional Application Ser. No. 60/806,664 filed Jul. 6, 2006, the entire contents of which are incorporated herein by reference.

TECHNICAL FIELD

The present invention pertains to improved methods and apparatus providing support to a portion of the urethra or rectum or anus to alleviate urinary or fecal incontinence and particularly to elongated slings having mechanisms for selectively adjusting the tension applied through the sling to body tissue.

BACKGROUND

Urinary incontinence is a condition characterized by involuntary loss of urine, beyond the individual's control, due to the loss or diminution of the ability to maintain the urethral sphincter closed as the bladder fills with urine. Male or female stress urinary incontinence (SUI) occurs when the patient is physically or emotionally stressed. Such patients may also experience urge incontinence.

Fecal incontinence is a condition characterized by involuntary defecation or passage of feces through the anal canal due to injury to or weakness of one or more of the internal anal sphincter, the external anal sphincter, and the levator ani.

Implantable urethral and anal prosthetic sphincter systems have been disclosed in the prior art to treat incontinence that comprise an inflatable balloon that is either pillow or cuff shaped, a balloon reservoir/pressure source filled with a fluid, a pump, and interconnecting tubing. The balloon is implantable beneath or surrounding the urethral tract (at or near the bladder neck in female patients) or around the anal sphincter and is coupled through tubing to the balloon reservoir/pressure source and pump that are implanted subcutaneously. The pump may be manually actuated to inflate the balloon, which in turn compresses the urethral tract and prevents incontinence. The balloon may be deflated to allow voiding. Examples of such prosthetic sphincter systems are disclosed in U.S. Pat. Nos. 4,222,377, 4,571,749, and 5,562,598, and one such system comprises the AMS-800 Urinary Control System available from American Medical Systems, Inc.

Urethral tapes or slings have been developed that are implanted in a urethral sling procedure in which the urethral sling is inserted beneath the urethra and advanced in the retro pubic space, perforating the abdominal fascia. In one procedure, peripheral or end portions of the elongated urethral sling are affixed to bone or body tissue, and a central support portion of the elongated urethral sling extends under the urethral or bladder neck to provide a platform that compresses the urethral sphincter, limits urethral distension, and pelvic drop, and thereby improves coaptation. Elongated "self-fixating" slings have also been clinically introduced for implantation in the body that do not require that the end portions be physically attached to tissue or bone and that rely upon tissue ingrowth into sling pores to stabilize the sling as disclosed, for example, in commonly assigned U.S. Pat. Nos. 6,382,214, 6,612,977, 6,641,524, 6,648,921, 6,652,450, 6,702,827, 6,802,807, and 6,911,003 and publications and patents cited therein.

The above-described slings comprise a central portion that is adapted to support the urethra, two end portions bracketing the support portion, a protective sheath or sheaths encasing at least the end portions, and connectors at the ends of the sling. Various ways of attaching a sleeve end and sling mesh end to a connector are detailed in the above-referenced '450 patent, for example. Further ways of attaching sling ends to sling implantation tools are disclosed in U.S. Patent Application Publication Nos. 2004/0087970, 2005/0245787, and 2005/0250977. The sling implantation tools are employed to form tissue pathways extending from a vaginal incision to two abdominal skin incisions and to draw the sling end portions through the pathways to dispose the sling free ends out of the skin incisions and the central portion around the urethra. The connectors are detached from the sling ends, and the sheaths are drawn out of the skin incisions, allowing the incisions to be closed.

Sling tension is typically adjusted at implantation sufficiently to take up any slack in the sling and impart at least a degree of increased tension to the urethra with the bladder empty. A surgical instrument may be placed between the sling central portion and the urethra, the sling ends drawn to tension and fully close the urethral tract, and the instrument withdrawn so that the uethra is relaxed sufficiently to function. Alternative tension adjustment mechanisms that may be employed during implantation are disclosed in the above-referenced commonly assigned '827 and '921 patents.

Typically, such urethral tapes or slings are fabricated of a loose weave sling fabric or mesh that acutely engages tissue and encourages tissue ingrowth along the pathway through mesh pores to achieve chronic stabilization or "self-fixation. Tissue ingrowth takes about 2-3 weeks in the typical patient in the absence of any significant intentional or unintentional movement of the mesh. During this post-operative time, the patient monitors the degree of success achieved in ameliorating leakage and any discomfort that might occur if the applied tension is so high as to unduly slow voluntary urination.

If any such problems occur, it may be necessary to reopen the incisions to access and pull on the sling ends to tighten the sling central portion around the urethra or to reopen the vaginal incision to pull on the sling central portion to loosen the sling central portion around the urethra. Several approaches have been taken to simplify or reduce the need for such post-operative adjustments.

One tension adjustment complication arises from the fact that the loose weave sling mesh inherently stretches and elongates when tension is applied at the ends or central support portion to overcome resistance of the tissue bearing against the sling mesh along the tissue pathway. It is difficult to judge just how much tension to apply to achieve adequate tightening or loosening in the central support portion. In one approach to overcoming this complication disclosed, for example, in the above-referenced '450 patent, an elongated repositioning means, e.g., an elongated inextensible tensioning member, is incorporated extending in or along the sling mesh from near the sling ends to or through the sling central portion. Tension applied to the repositioning means is transmitted along the length of the sling so the sling mesh does not substantially stretch during initial positioning and any repositioning during the acute healing phase.

In another approach disclosed, for example, in U.S. Patent Application Publication 2006/0058574 (FIGS. 4a-4f), an expandable member or container is incorporated on or in the sling central support portion that can be inflated or deflated with bulking agent to apply more or less tension to the urethra. As stated therein, optionally, the container has a touchable internal valve element to permit the surgeon to palpate the area prior to injecting or removing the bulking agent. Alternatively, the bulking agent may be injected and removed via a two-way external port. When a bulking agent is injected into the container, the tissue between the mesh and urethra will expand. This results in two effects; a simple vertical lifting due to expansion and a vertical lifting due to stretching the outside of the mesh. A suitable bulking agent may be water or saline. A similar approach is disclosed in U.S. Pat. Nos. 4,019,499 and 6,786,861.

Other approaches that enable increasing tension of the sling central portion against the urethra involve shortening the lengths of the sling end portions as described, for example in the above-referenced, commonly assigned '921 patent. Mesh folds are formed in the sling end portions using filaments that extend through vaginal incisions externally of the body. Depending on the embodiment, the mesh folds can be released to decrease sling tension or be tightened to increase sling tension by pulling on the filament ends following the initial implantation procedure. In other embodiments, filaments are extended substantially through the lengths of the sling end portions and extend from the vaginal incisions. The filaments may be gripped and pulled to tighten the mesh in the sling end portions to increase overall sling tension.

In still another approach disclosed, for example, in U.S. Patent Application Publication 2006/0058574 (FIGS. 5a-5c), the mesh sling or tape is further modified to include a mechanical adjustment means to adjust the length of the tape in the end portions on either side of the central portion after the tape has been implanted in the tissue pathways. The mechanical adjustment means incorporate a tie-wrap mechanism or sutures and one-way suture retaining devices of the type disclosed in U.S. Pat. No. 5,669,935 located along the tape on either side of the central portion. In each case, one suture end is affixed to the tape and extends along it and through a suture retaining device affixed to the tape closer to the central portion. The sutures or tie-wrap are not tensioned at implantation, and the tie-wrap or suture free ends extend through the vaginal incision. If the tension on the urethra is too light as determined during the acute healing phase, the surgeon may grasp and pull on the tie-wrap or suture free ends to shorten the lengths of the tape end portions and thereby increase sling tension. The exposed suture or tie-wrap ends may be severed during chronic implantation.

In yet another approach, tape or sling ends or the end of a tensioning cable coupled to a urethral support mechanism are coupled to an adjustment mechanism that is chronically implanted subcutaneously and can be accessed to adjust sling tension. See, for example, commonly assigned U.S. Pat. No. 4,969,892 and further U.S. Pat. Nos. 5,474,518 and 6,117,067 and the REMEEX® readjustable sling by Neomedic, Intl. (www.remeex.com). Ratchet or gear adjustment mechanisms that are accessed using a driver inserted through the skin and thereby rotated to increase or decrease sling tension are disclosed in the '892 and '518 patents. An inflatable/deflatable elastic chamber, adjustment mechanism that incorporates a fill port that is penetrable by a syringe needle advanced through the skin is disclosed in the '067 patent. The adjustment forces are applied to the sling ends and must be transmitted through the sling to effect any change in tension along the sling central portion adjacent the urethra.

Further sling tension adjustment mechanisms and techniques involve adding tensioning filaments to the sling free ends and extending the elements through the skin incisions and into engagement with buttons or pads implanted subcutaneously engaging a muscle or rectus fascia layer and/or having tissue engaging elements or anchors along the filament or at the sling ends that engage subcutaneous tissues as disclosed, for example, in U.S. Pat. No. 6,911,002 and in U.S. Patent Application Publication Nos. 2005/0004576 and 2006/0089525.

Although effective in alleviating SUI, further improvements in urethral and anal slings to post-operatively adjust tension applied to the urethra and anus are desirable.

SUMMARY

The preferred embodiments of the present invention incorporate a number of inventive features that address the above-described problems that may be combined as illustrated by the preferred embodiments or advantageously separately employed.

The present invention involves improvements in an elongated incontinence sling, or simply sling, comprising a central support portion and end portions extending from the central portion to sling ends. Herein, use of the term sling or the expression "incontinence sling" without further qualification shall embrace urethral slings adapted to be placed through a tissue pathway disposing the central support portion between the urethra or bladder neck (hereafter collectively referred to as the urethra for convenience) and the vaginal wall to alleviate urethral incontinence and fecal slings adapted to be placed through a tissue pathway disposing the central support portion inferior to the anus, the anal sphincter or the lower rectum (hereafter collectively referred to as the anus for convenience) to alleviate fecal incontinence. Certain embodiments employ tensioning filaments or lines or sutures that are referred to as sutures for convenience.

In accordance with the present invention, such slings are improved to enhance post-operative sling adjustment of the tension applied to the urethra or anus to enhance efficacy and patient comfort. Several categories of the invention are disclosed herein. The various embodiments disclosed herein are applicable to both males and females, to address issues of incontinence in both, to address issues of prolapse repair in female and perineal floor descent, as well as fecal incontinence in both. Also surgical techniques such as forming suprapubic, retropubic, transobturator, inside out, outside in tissue pathways between two skin incisions, or a tissue pathway formed from a single incision through the vagina or perineal floor (in male or female patients) are also contemplated for passage of a sling therethrough.

In various embodiments, sling tension adjustment mechanisms join separate sling pieces forming part of the sling mesh with the sling end portions such that the sling tension adjustment mechanisms are interposed between and attached to sling intermediate ends that are spaced apart by an adjustment spacing. Various adjustment actuators and techniques are employed to adjust the sling tension adjustment mechanisms to decrease or increase the adjustment spacing between the sling intermediate ends to thereby shorten or lengthen, respectively, the overall length of the sling end portions and to thereby increase or decrease, respectively, the tension applied by the central support portion to the urethra or anus. The sling tension adjustment mechanisms are disposed along the sling end portions so as to be disposed at tissue pathway locations that are proximate the patient's skin to enable application of the external adjustment actuator against the skin or through the skin and underlying tissues to operate the sling tension adjustment mechanisms.

In one embodiment, sutures are threaded back and forth through mesh pores adjacent the intermediate ends and across the respective adjustment spacings of each sling end portion. The suture ends are adapted to be extended through the skin incisions to function as adjustment actuators in the manner of draw strings for later adjustment of the adjustment spacings during the acute healing phase. The suture ends may be grasped and pulled to pull the sling intermediate ends closer together to decrease the adjustment spacing and thereby decrease the sling length and increase tension applied by the center support portion to the urethra or anus.

In a variation of this embodiment, the tensioning sutures are passed through suture or tissue anchors that engage subcutaneous muscle, the rectus fascia or the transobturator membrane and extend through the skin incisions employed to form the tissue pathway that the sling extends through. Alternatively, the tensioning sutures are passed through suture or tissue anchors that engage subcutaneous muscle, the rectus fascia or the transobturator membrane and extend through other skin incisions to be grasped and pulled on to adjust tension. For convenience, such subcutaneous muscle, the rectus fascia or the transobturator membrane or other membranes and fascia are collectively referred to as tissue layers herein.

In another embodiment, the external adjustment actuator comprises a signal transmitter that is employed to generate a sling adjustment command that passes transcutaneously (through the intact skin), and the adjustment mechanism comprises a receiver for receiving the transmitted commands and increases or decreases the adjustment spacing. In yet further embodiments, the external adjustment actuator is a magnetic field generator or permanent magnet that is employed to generate a magnetic field representing a sling adjustment command that passes transcutaneously through the skin, and the adjustment mechanism comprises a magnetic field responsive element that responds by increasing or decreasing the adjustment spacing. In still further embodiments, the sling tension adjustment mechanism comprises a temperature responsive element responsive to heat or cold applied transcutaneously by an external thermal heater or cooler to heat or cool the adjustment mechanism to thereby increase or decrease the adjustment spacing. In yet further embodiments, the sling tension adjustment mechanism comprises light responsive elements responsive to certain wavelengths of light that can be generated by an external adjustment actuator and transmitted transcutaneously to the sling tension adjustment mechanism to thereby increase or decrease the adjustment spacing.

In still another embodiment, the external adjustment actuator is inserted percutaneously (penetrating the skin) to engage and operate the sling tension adjustment mechanism to increase or decrease the adjustment spacing. Various sling tension adjustment mechanisms are provided that can be rotated by the external adjustment actuator in one direction to draw the sling intermediate ends together to increase sling tension and that can be rotated in the other direction to allow the sling intermediate ends to separate apart to decrease sling tension.

In yet another embodiment, the external adjustment actuator is a syringe or the like that is inserted percutaneously to engage a port of a fluid retaining chamber of the sling tension adjustment mechanism, whereby the adjustment spacing is adjusted by injecting or withdrawing fluid from the fluid chamber to increase or decrease the adjustment spacing. In certain variations, the sling tension adjustment mechanism comprises a fluid reservoir to be implanted just below the skin, a fluid chamber disposed in the adjustment spacing and coupled to the intermediate ends, and a tube extending between the fluid reservoir and the fluid chamber in each sling end portion. The fluid reservoir has a fluid delivery/withdrawal port that may be percutaneously accessed to introduce fluid into the fluid reservoir or to withdraw fluid from the fluid reservoir following implantation of the sling to thereby adjust the amount of fluid in the fluid chamber and adjust the length of the adjustable spacing.

In certain embodiments, the fluid chamber comprises a single action hydraulic cylinder disposed in the adjustment spacing coupled to one sling intermediate end, the cylinder containing a fluid operated piston within an elongated chamber, the cylinder coupled to a sling adjustment rod that is in turn coupled to the other sling intermediate end. The fluid volume introduced into the fluid chamber determines the piston location in the cylinder and the resulting length of the adjustment spacing. In a variation, a dual action hydraulic cylinder having a pair of opposed pistons in the fluid chamber are each coupled to rods that are in turn coupled to sling intermediate ends governs the adjustment spacing.

In these embodiments, the fluid chambers are preferably empty of fluid when the sterile sling is supplied in the sterile package from the manufacturer. Implantation of the sling through body pathways may be simpler and easier with the fluid chambers empty. The fluid, e.g., a sterile saline or other biocompatible hydraulic fluid, may be introduced through the fluid delivery port(s) while the port(s) are still accessible. The amount of fluid necessary to effect blockage of the urethral tract may be checked by draining and filling the patient's bladder through the urethral tract, determining efficacy, and adding or withdrawing fluid to adjust the applied urethral pressures in the pressurized and ambient pressure fluid distribution states. Similar procedures may be employed to effect constriction of the anal canal.

In further embodiments the external adjustment actuator comprises an elongated gear drive instrument having a shaft extending between a handle and an engaging end shaped to be percutaneously advanced through the skin. The adjustment mechanism comprises a driven gear means engageable by the engaging end the gear drive for operating the spacing adjustment means to increase or decrease the adjustment spacing.

Optionally, sling end tissue anchors may be provided on sling ends to engage tissues, e.g., the rectus fascia or the obturator membrane to fix the sling ends and aid in tension adjustment of the sling end portions.

Optionally, a sling adjustment mechanism may be incorporated into the sling central support portion to enable the separate tensioning of the sling central support portion.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 1 is a schematic view of an exemplary sling assembly enclosing a sling adapted to be modified in accordance with the invention to function as an adjustable tension urethral or fecal sling;

FIG. 2 is a schematic illustration of the sling of FIG. 1 adapted to be modified in accordance with the invention to provide an adjustable tension function;

FIGS. 47 and 48 are schematic plan views in partial section illustrating one form of locking mechanism incorporated into the single action hydraulic cylinder adjustment mechanism of FIGS. 28-31;

FIGS. 49 and 50 are schematic plan views in partial section illustrating another form of locking mechanism incorporated into the single action hydraulic cylinder adjustment mechanism of FIGS. 28-31;

FIG. 54 is a schematic Illustration of a miniaturized, mechanical gear, adjustment mechanism that is adjusted by a gear drive extended temporarily through the patient's skin;

FIG. 55 is a schematic expanded view in partial section illustrating the gear drive components within the adjustment mechanism of FIG. 54;

Figure 3:
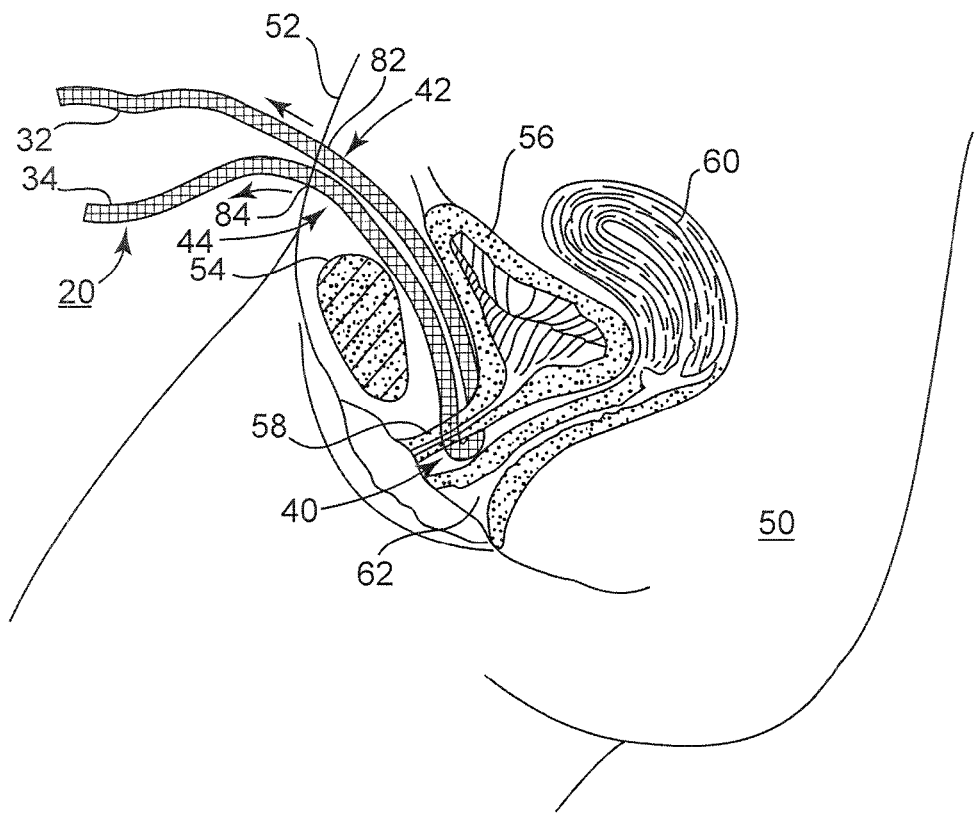
FIG. 3 is a schematic illustration of a urethral sling of FIG. 2 implanted in a female patient's body in relation to the urethra or bladder neck.

The drawing figures are not necessarily to scale.

DETAILED DESCRIPTION OF PREFERRED EMBODIMENTS

The various embodiments of the present invention are implemented in slings suitable for and methods of implanting such slings in the treatment of male and female urinary and fecal incontinence and to effect pelvic floor, perineal floor, and pelvic proplapse repairs employing a variety of surgical approaches. For example, female pelvic floor repair slings may be implanted by techniques that involve transvaginal, transobturator, suprapubic, pre-pubic, or transperineal exposures or pathways, and male urinary incontinence slings may be implanted by techniques that involve transobturator, suprapubic, or transperineal pathways. Any of the disclosed embodiments can be used as fecal incontinence slings which may be implanted by techniques that involve transvaginal, transobturator, suprapubic or via perineal floor pathways. In fecal incontinence applications, the disclosed embodiments can be used to correct the anorectal angle in the rectum to re-establish continence in patients. The above methods can, but are not necessarily limited to, utilize helical needles of the type described in U.S. Pat. No. 6,911,003 or C-shaped needles or elongate needles of the type used to perform suprapubic procedures.

Referring to FIG. 1, an exemplary embodiment of an elongated sling assembly 10 is depicted in which the embodiments of the present invention may be advantageously implemented. The elongated sling assembly 10 contains a sling 20 that may be implanted in any of the above-described manners and pathways through which at least end portions of the elongated sling assembly 10 is drawn to dispose a central support portion 40 of sling 20 in operative relation to the urethral or bladder neck or around the anal sphincter or elsewhere in the pelvic region. The sling assembly 10 comprises the sling 20 coupled to sling end connectors 12 and 14 and encased in protective sheaths 22 and 24.

The depicted exemplary sling assembly 10 thus extends between sling end connectors 12 and 14 that engage with the free ends of right hand and left hand sling implantation tools of the types described above, for example. The sling end connectors 12 and 14 are shaped to dilate the right and left passages or pathways through body tissue formed by the curved needles of the right and left hand implantation tools in the above-described trans-vaginal or transobturator procedures, for example.

In this example, the sling 20 is enclosed within protective sheaths 22 and 24 extending from the sling end connectors, 12 and 14, respectively, to respective free and open sheath ends 26 and 28. Preferably, the protective sheaths 22 and 24 are constructed of a flexible thin transparent plastic film that enables visual examination of the sling 20 and is sufficiently lubricious that it passes easily through the tissue pathways of the patient formed using the right hand and left hand sling implantation tools of the types described above or otherwise created. The sheaths 22 and 24 can include sheath indicia or tear scores, perforations or holes for assisting the surgeon in properly orienting sling 20 relative to the urethra. Embodiments of the present invention are contemplated that involve modifying the sheaths 22 and 24.

The sling 20 that is left in place chronically (following implantation and removal of sheaths 22 and 24 and end connectors 12 and 14) comprises an elongated, rectangular (in this depicted embodiment) braided or preferably knitted, mesh strip or simply mesh 30 as shown in FIG. 2. The sling 20 and mesh 30 are subdivided into a central support portion 40 that is adapted to be placed through a pathway extending between the urethra or bladder neck and the vaginal wall. Proximal end portions 42 and 44 of sling 20 extend from the central support portion 40 to the mesh ends 32 and 34. In FIGS. 1-5, the mesh 30 extends between mesh ends 32 and 34 and may be continuous throughout the length of the sling 20 between mesh ends 32 and 34. However, it will be understood that the central portion 40 of sling 20 may be formed of other materials such that the central portion 40 is physically attached to the end portions 42 and 44. In certain embodiments, the central portion 40 may be formed of any tissue-compatible synthetic material or any natural biocompatible material, including, but not limited to, treated autologous, allograft, or xenograft tissues, procine dermis, a tissue engineered matrix, or a combination thereof.

The sling 20 of sling assembly 10 is therefore similar to those disclosed in the above-referenced '450 and '003 patents but is modified herein to incorporate one or more of the aspects of the present invention. It will be understood that the mesh 30 may be dimensioned shaped in a variety of ways known in the art for implantation in the treatment of male and female urinary and fecal incontinence and to effect pelvic floor, perineal floor, and pelvic prolapse repairs employing a variety of surgical approaches. For example, the sling 20 may comprise more than two end portions 42 and 44 coupled to connectors and extending at a variety of angles from a particularly shaped center portion 40.

In the implantation procedures described in the above-referenced '214, '450, and '524 patents and U.S. Patent Application Publication Nos. 2005/0043580 and 2005/0065395, the sling connector ends 12 and 14 are fitted to the implantation tools and the proximal end portions 42 and 44 are drawn through the body passageway or pathway. The central support portion 40 is adapted to drawn against tissue to support the urethra or bladder neck or the anal sphincter or elsewhere in the pelvic region after the proximal end portions 42 and 44 are drawn through body pathways. The sling connector ends 12, and 14 are drawn out of the skin incision and detached from the implantation tool needle ends. The mesh 30 and sheaths 22 and 24 are severed just proximate to the connector ends 12 and 14, respectively. The remaining portions of the protective sheaths 22 and 24 are withdrawn over the mesh 30 and through the skin incisions. The sling 20 then remains in place, and tension adjustments are made to provide sufficient urethral or anal resistance to leakage. The incisions are closed upon completion of the tests, and tissue ingrowth into the pores of the mesh 30 takes place in a matter of weeks.

Before describing the embodiments of the invention, attention is directed to a step illustrated in FIG. 3 of one such sling implantation procedure that results in the sling 20 extending through a tissue pathway created in a female (for example) patient 50 extending around the urethra 58. In preceding steps, the tissue pathway was formed by passing needles through a vaginal skin incision 62 just adjacent to the vagina 60 through soft tissue between urethra 58 and vagina 60 and along each side of urethra 58 through layers of fat, muscle, and fascia and between pubic bone 54 and bladder 56 to first and second skin incisions through skin 52. Any of the known tissue pathways may be formed in this generally described manner. In a related embodiment, a sling is implanted via a single incision (vaginal incision 62) with the sling being pushed up into the transobturator or retro pubic space. The end connectors 12 and 14 of the sling assembly 10 were attached to the same or other needles to draw the sling assembly 10 through the tissue pathway to dispose the end connectors outside the patient's skin 52. As shown in FIG. 3, the connectors 12 and 14 and sheaths 22 and 24 were removed after being drawn out of the skin incisions, leaving the sling 20 in place. In a related embodiment, connectors 12 and 14 are eliminated.

Figure 4:
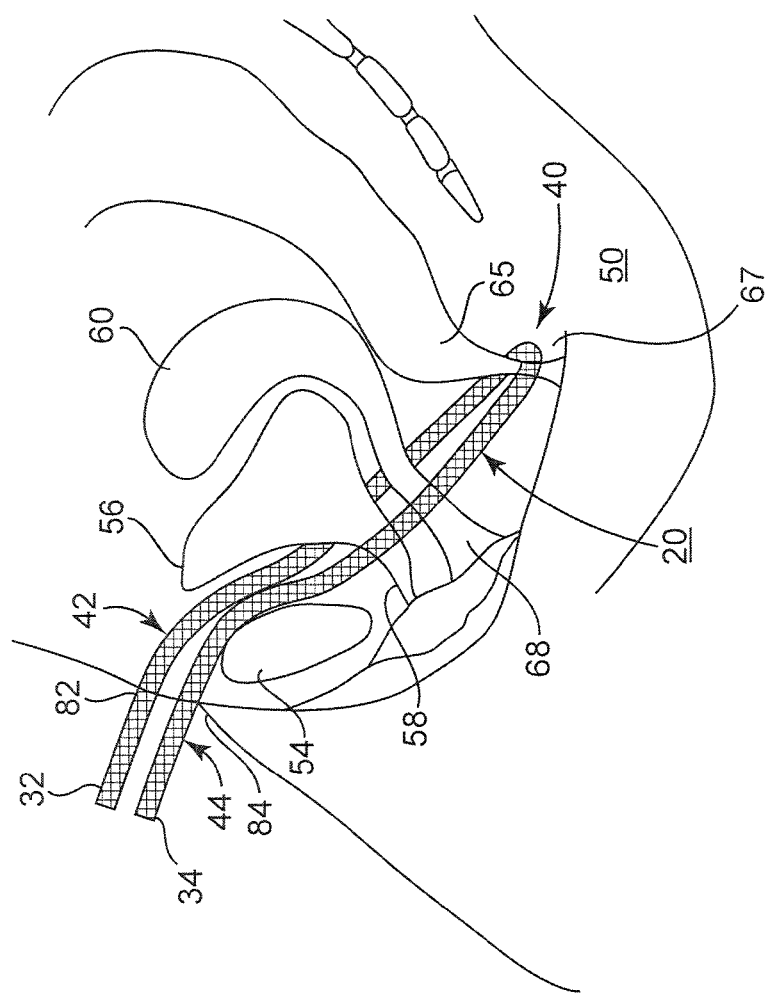
FIG. 4 is a schematic illustration of a fecal sling of FIG. 2 implanted in a female patient's body in relation to the anus and rectum.

Referring to FIG. 4, a schematic illustration of an incontinence sling implanted in a female (for example) patient's body for treating fecal incontinence is depicted. In this illustration, the sling central portion 40 extends underneath the anus or anal sphincter 67 or inferior portion of the rectum 65 (hereafter collectively referred to as the anus 67 for convenience) to correct the anorectal angle in the patient. Various surgical approaches can be used to implant sling 20 to correct fecal incontinence including suprapubic, transobturator, retropubic, prepubic, transperineal and transvaginal (including a single incision approach transvaginally or transperineally).

Figure 5:
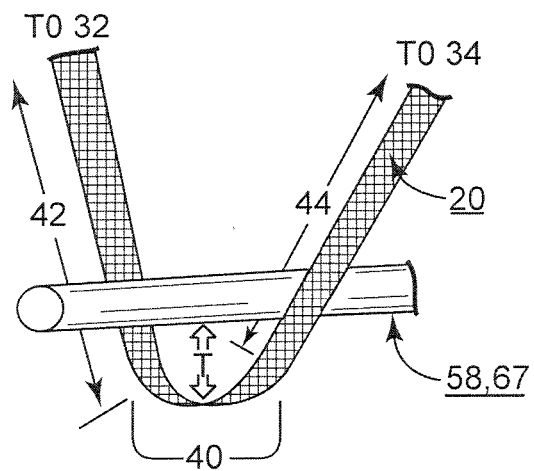
FIG. 5 is a schematic illustration of the relation of the sling central support portion and sling end portions to the urethra or anus.

At this point, the tension T that sling 20 applies against the urethra 58 or anus 67 is adjusted as schematically illustrated in FIG. 5. Since the procedure may be performed using a local anesthesia, the patient 50 is able to provide feedback to the surgeon during adjustment of sling tension. In the procedure illustrated in FIG. 3, typically, the bladder 56 is filled with saline using a catheter, and the patient is requested to cough. The surgeon is able to determine whether leakage occurs and may adjust the tension on the sling 20 by pulling on the exposed sling ends 32 and 34 to increase tension of the center support portion 40 against the urethra 58 or by pulling on center support portion through the vaginal incision to decrease the tension of the center support portion 40 against the urethra 58. The exposed end sections of the end portions 42 and 44 are trimmed away, and the abdominal incisions and the vaginal incision (as well as the labia fold incisions for the transobturator approach) are closed. In the various embodiments of the present invention, such slings as sling 20 are improved to enhance post-operative sling adjustment of the tension T applied to the urethra 58 or the anus 67 to enhance efficacy and patient comfort.

While not essential to the practice of the present invention, it may be desirable to provide mechanisms incorporated into or that act on the sling central support portion 40 to facilitate the adjustment of the tension T applied to the urethra 58 or the anus 67. For example, a sling central portion adjustment mechanism may be provided to increase and/or decrease the tension applied locally to the urethra 58 or the anus 67. The sling central portion adjustment mechanism is associated directly or indirectly with the sling central support portion 40 and is distinct from the sling tension adjustment mechanisms incorporated in the sling end portion or portions.

Figure 10:
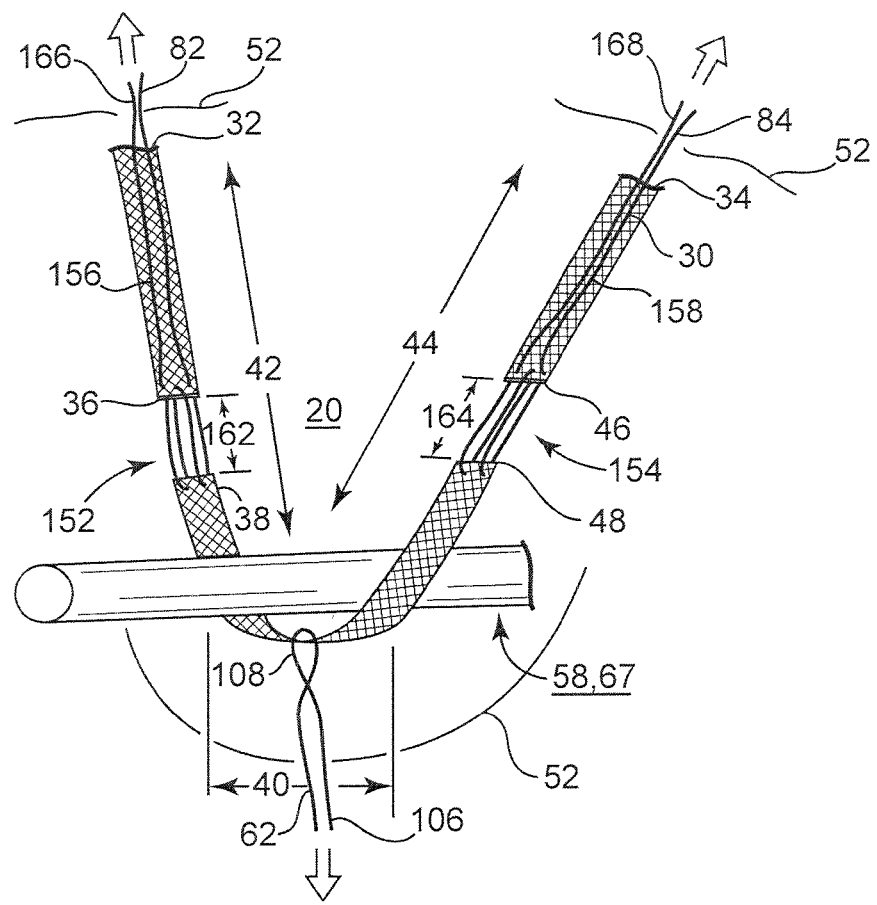
FIG. 10 is a schematic illustration of a further embodiment of an adjustable tension sling, wherein sling tension adjustment sutures bridge adjustment spacings in the sling end portions and extend through the skin to increase and/or decrease the sling tension.

For example, as shown in FIG. 10, the sling central portion tension adjustment may simply comprise a suture 108 extending around the sling central portion and passing through the skin incision to provide post-operative tension adjustment of the sling central portion 40 by pulling on suture ends 106. Adjustments may be made until the suture is withdrawn through the skin 52 or is absorbed by the body.

Longer-term post-operative adjustment of the sling central portion tension may be accomplished with sling central portion adjustment mechanisms that remain in place. In one approach, the mechanism may be accessed for tension adjustment employing an external adjustment actuator that is percutaneously advanced through the skin 52 to engage the sling central portion adjustment mechanism. For example, one such approach involves injecting or withdrawing fluid from a fluid chamber of a pillow of the sling central portion adjustment mechanism applying pressure to the urethra 58 or the anus 67.

In certain more complex embodiments of the second category, sling tension adjustment mechanisms are formed in gaps in the sling mesh forming the sling end portions such that the sling tension adjustment mechanisms are interposed between and attached to sling intermediate ends that are spaced apart by an adjustment spacing. Various mechanisms and techniques are employed to adjust the sling tension adjustment mechanisms to decrease or increase the adjustment spacing between the sling intermediate ends to thereby shorten or lengthen, respectively, the overall length of the sling end portions and to thereby increase or decrease, respectively, the tension applied by the central support portion to the urethra. The sling tension adjustment mechanisms are disposed along the sling end portions so as to be disposed at tissue pathway locations that are proximate the patient's skin to enable access to or application of the external adjustment actuator against the skin or through the skin and underlying tissues to operate the sling tension adjustment mechanisms.

Figure 6:
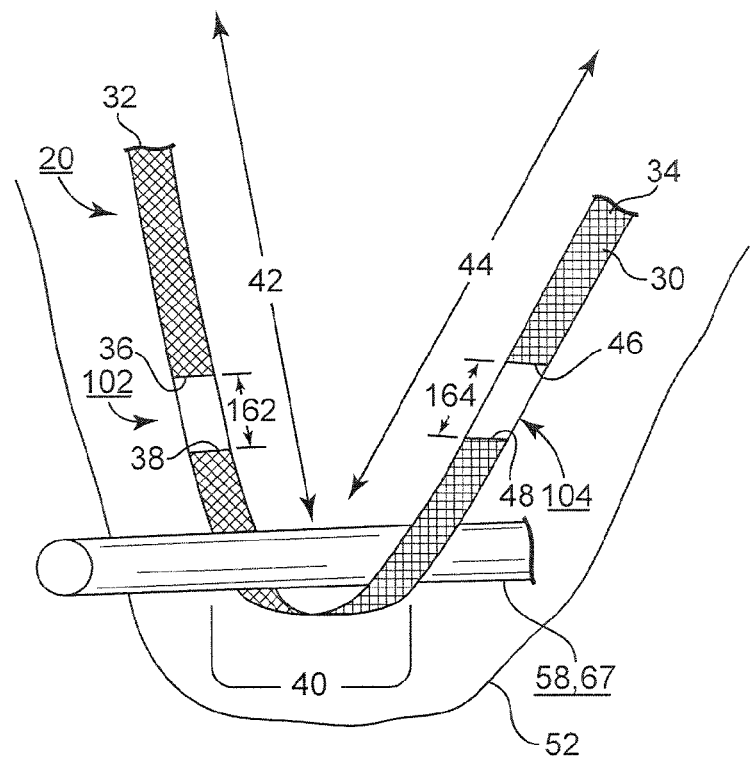
FIG. 6 is a schematic illustration of a generic embodiment of an adjustable tension sling of the present invention having sling tension adjustment mechanisms formed in gaps or spaces in the sling mesh forming the sling end portions such that the sling tension adjustment mechanisms are interposed between and attached to sling intermediate ends that are spaced apart by an adjustment spacing.
Figure 7:
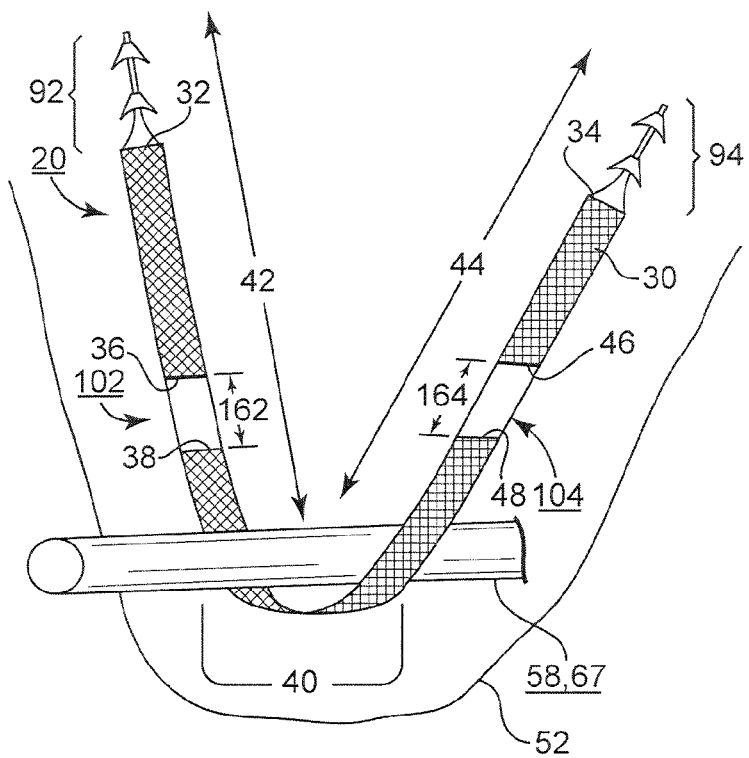
FIG. 7 is a schematic illustration of the generic embodiment of FIG. 6 having optional tissue anchors extending from the sling ends to aid in the operation of the sling tension adjustment mechanisms.

Turning to FIGS. 6 and 7, in accordance with embodiments of the present invention, a sling tension adjustment mechanism is incorporated into or on a section of one or preferably both of the sling end portions 42 and 44 proximal to but spaced from the central support portion 40 that can be adjusted at least in the acute post-operative healing phase. A first sling end portion tension adjustment mechanism 102 is schematically depicted extending between and coupled to sling intermediate ends 36 and 38 of sling end portion 42. The gap or adjustment spacing 162 between sling intermediate ends 36 and 38 is shortened to increase tension or lengthened to decrease tension in sling end portion 42 Similarly, a second sling end portion tension adjustment mechanism 104 is schematically depicted extending between and coupled to sling intermediate ends 46 and 48 of sling end portion 44. The gap or adjustment spacing 164 between sling intermediate ends 46 and 48 is shortened to increase tension or lengthened to decrease tension in sling end portion 44. The spacing of each sling tension adjustment mechanism 102 and 104 from the central support portion 40 is selected in relation to the anatomy for either male or female fecal or urinary incontinence slings and the implantation route or technique to facilitate access or engagement with an externally applied adjustment actuator or an actuator element extending percutaneously from a skin incision. The adjustment mechanisms are generally adjusted to adjust the length and/or tension of the end portions 42 and 44 to thereby tension the center support portion 40 and draw it closer to the urethra 58 or anus 67 to relax tension of the center support portion 40 to release pressure on the urethra 58 or anus 67.

As shown in FIG. 7, it may be desirable to stabilize the sling ends 32 and 34 in tissue by optionally providing sling tissue anchors 92 and 94 extending from the sling ends 32 and 34. The anchors 92 may take any of the forms disclosed in the above-referenced U.S. Patent Application Publication No. 2005/0004576, for example. Generally speaking such tissue anchors 92 and 94 can be readily drawn through tissue in the direction away from the sling ends 32 and 34, respectively, but resist retraction back through the tissue. Advantageously, the sling tissue anchors 92 and 94 may be extended through and bear against the rectus fascia or the transobturator to stabilize the sling ends 32 and 34 to set sling tension and to resist being drawn toward the sling tension adjustment mechanisms 102 and 104 when tension is increased.

Figure 8:
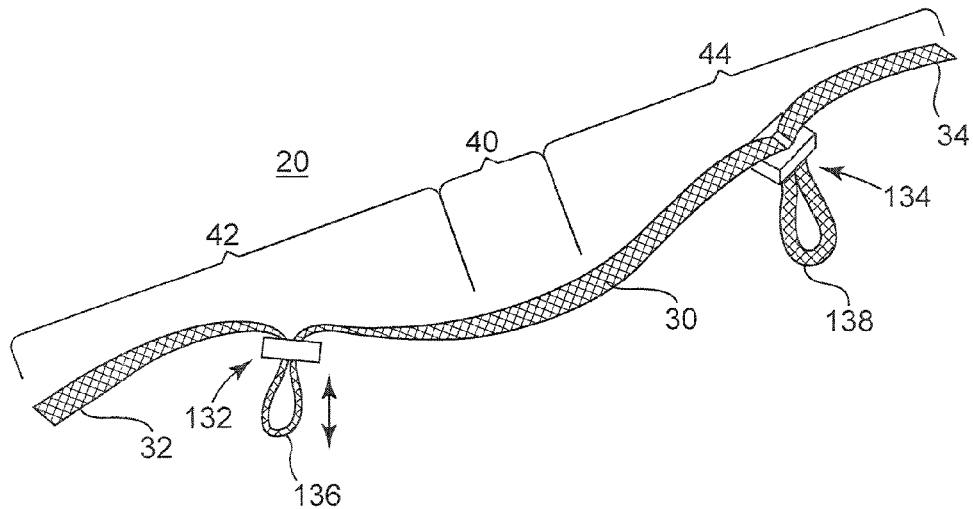
FIGS. 8 and 9 are schematic illustrations of an embodiment of an adjustable tension sling, wherein sliding locks that engage intermediate ends or loops of the sling mesh are incorporated into the sling end portions to increase and/or decrease the sling tension.
Figure 9:
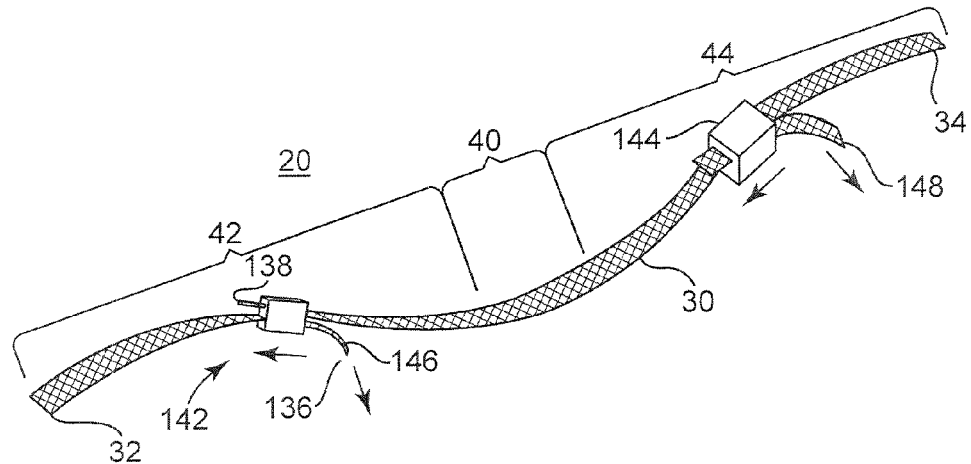

In certain particular embodiments of the invention depicted in FIGS. 8 and 9, the end portion tension adjustment mechanisms comprise sliding locks 132 and 134 (FIG. 8) or 142 and 144 (FIG. 9) that engage the end portions 42 and 44 of the sling mesh 30. In one variation shown in FIG. 16, sections of the sling mesh 30 are looped and passed through channels of sliding locks 132 and 134. In the other variation shown in FIG. 9, the sling intermediate ends are drawn through channels of the sliding locks 142 and 144. It will be understood that the depicted slings 20 are disposed in the patient's body the manner depicted in FIG. 3 or FIG. 4. The loops 136, 138 or free ends 146, 148 function as actuator elements that can be grasped through the skin incisions 82 and 84 (or through a vaginal incision if a single incision approach is chosen) and pulled upon with respect to the sliding locks 132, 134 or 142, 144 to shorten the lengths of the end portions 42, 44 and increase tension on the urethra 58.

Sliding locks 132, 134 and 142, 144 operate similar to zip-tie locks. It will be understood that the depicted loops 136, 138 and the free ends 146, 148 can comprise sutures or zip-lock tapes fastened to intermediate ends of the sling mesh 30 so that the sutures or zip-lock tapes are drawn through channels of the sliding locks 132, 134 and 142, 144.

A further specific embodiment of the present invention is depicted in FIG. 10, wherein the end portion 42 is severed at intermediate ends 36 and 38 to form a gap or adjustment spacing 162, and the end portion 44 is severed at intermediate ends 46 and 48 to form a gap or adjustment spacing 164. Sutures 156 and 158 are threaded back and forth through mesh pores adjacent the intermediate ends 36, 38 and 46, 48, respectively, and across the respective adjustment spacings 162 and 164, to function as draw strings for later adjustment of the adjustment spacings 162 and 164 during the acute healing phase. The suture 156 and adjustment spacing 162 comprise sling end portion tension adjustment mechanism 152 of end portion 42, and the suture 158 and adjustment spacing 164 comprise sling end portion tension adjustment mechanism 154 of end portion 44.

In this embodiment, the suture ends 166 and 168 of respective sutures 156 and 158 extending from the skin incisions 82 and 84 during implantation of the sling 20 function as the adjustment actuators. The suture ends 166 and 168 may be grasped and pulled to shorten the adjustment spacings 162 and 164 to thereby shorten the sling end portions 42 and 44 and thereby decrease the sling length and increase tension applied by the center support portion 40 to the urethra 58 (or anus).

A further adjustment suture 108 (optionally formed of biodegradable material) is optionally placed around the sling mesh 30 and extended through the vaginal skin incision 62 to enable manual tension adjustment. The suture ends 106 may be grasped and pulled to function as an actuator element and pull the sling mesh away from the urethra 58 to release tension applied by the center support portion 40 to the urethra 58 (or anus).

In the absence of adjustment suture 108, the sling central support portion 40 may be accessed by reopening the vaginal incision 62 to pull on the sling 20 to draw the sutures 156 and 158 back through the mesh pores, thereby increasing the sling length and decreasing tension applied by the center support portion 40 to the urethra 58 (or anus).

Optionally, a biodegradable sheath may be placed over the adjustment mechanisms 152 and 154 and at least a portion of the sling mesh to inhibit tissue ingrowth into the mesh pores and adjustment spacings 162 and 164 and thereby ease adjustment of the sling 20 until the sheath is absorbed and tissue ingrowth encapsulates and immobilizes sling mesh 30.

The suture ends 166, 168, and 106 may be severed at the respective incisions 82, 84, and 62 following final adjustment.

Certain sling implantation procedures for urethral and fecal slings involve employing implantation instruments having needles that are advanced from a first skin incision to a second skin incision to form first and second or right and left (non-suprapubic) tissue pathways around the urethra 58 or the anus 67. The instruments or other instruments are then employed to push or pull the sling end portions 42 and 44 through the first and second pathways to dispose the sling ends near or through the skin incisions 82 and 84 as shown in FIGS. 3 and 4. The above-described embodiments contemplate implantation in such tissue pathways.

Other sling implantation procedures for urethral and fecal slings have sling ends configured to engage sling implantation tool needle ends to be pushed from a single incision adjacent the urethra 58 (or the anus 67) through first and second tissue pathways to dispose the sling end portions extending away from the urethra 58 (or anus 67). The skin incisions 82 and 84 are not necessarily made, and the sling ends are disposed at subcutaneous locations.

Figure 11A:
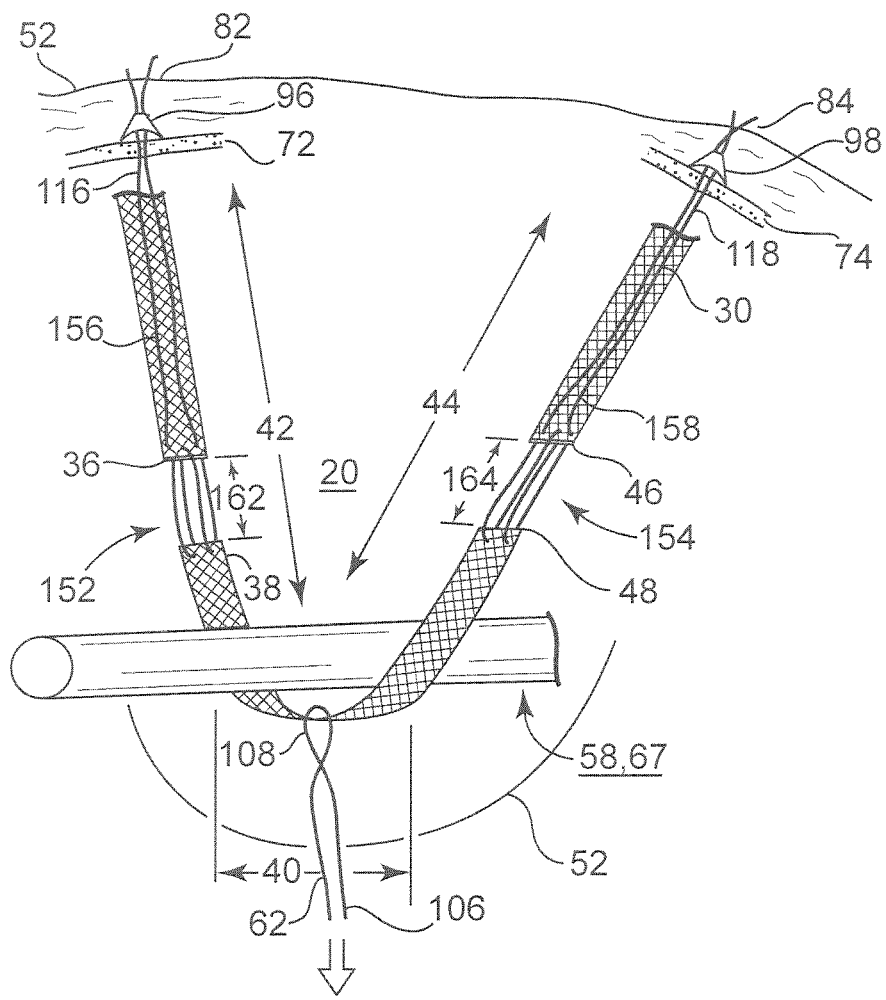
FIG. 11A is a schematic illustration of a variation of the adjustable tension sling of FIG. 10, wherein the sling tension adjustment sutures extend through or around tissue anchors and extend through the skin to be available to increase and/or decrease the sling tension.

In a variation of this embodiment of the invention depicted in FIG. 11A, the sutures 156 and 158 are drawn through tissue anchors 96 and 98 that are passed through and bear against subcutaneous tissue layers 72 and 74, respectively. Generally speaking, the tissue anchors 96 and 98 have channels or bores that one or both of the sutures 116 and 118 are passed though that grip the sutures with sufficient force to maintain sling tension. The suture retaining force may be overcome by manipulation of the suture and tissue anchor to increase or decrease sling tension during post-operative recuperation.

The suture ends extending through the skin incisions 82 and 84 are placed under the skin 52, and the incisions are closed. During chronic implantation, adjustments of sling tension may take place by reopening the skin incisions 82 and 84 to access the suture ends and the tissue anchors 96 and 98.

In this embodiment, the suture 156 passes through a slidable bore of the tissue anchor 96 and through the same skin incision 82 that the tissue pathway is created for the sling 20. Similarly, the suture 158 is depicted extending through a slidable bore of the tissue anchor 98 and through the same skin incision 84 that the tissue pathway is created for the sling 20. For example, the tissue pathway may extend through the right and left transobturator membranes (tissue layers 72 and 74) that the tissue anchors 96 and 98 are passed through and bear against.

Figure 11B:
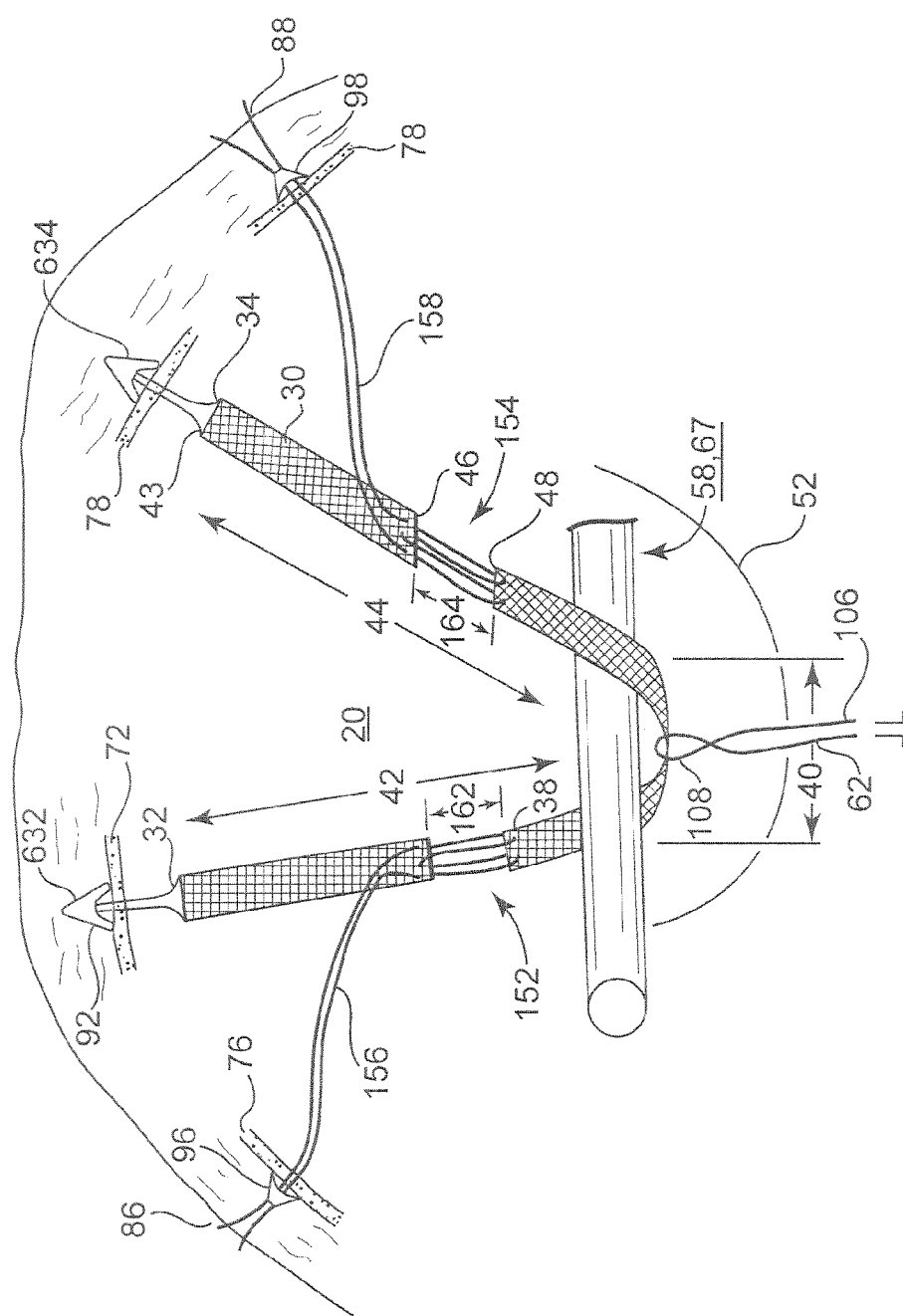
FIG. 11B is a schematic illustration of a further variation of the adjustable tension sling of FIG. 10, wherein the sling ends incorporate tissue anchors passed through and engaging tissue layers and the tension adjustment sutures extend through or around further tissue anchors and extend through the skin to be available to increase and/or decrease the sling tension.

In a further variation of this embodiment of the invention depicted in FIG. 11B, tissue anchors 632 and 634 are coupled to the sling ends 32 and 34, respectively, and the sutures 156 and 158 are passed through the tissue anchors 96 and 98. In the implantation procedure, the tissue anchor 632 and the sling end portion 42 are pushed from a single skin incision below the urethra 58 or anus 67 through a first tissue pathway such that the tissue anchor 632 is passed through and bears against tissue layer 72. Similarly, the tissue anchor 634 and the sling end portion 43 are pushed from the skin incision below the urethra 58 or anus 67 through a second tissue pathway such that the tissue anchor 634 is passed through and bears against tissue layer 74.

The suture 156 and tissue anchor 96 are pushed through a further tissue pathway such that the tissue anchor 96 is passed through and bears against a separate tissue layer 76 and then through a skin incision 86. Similarly, the suture 158 and tissue anchor 98 are pushed through a further tissue pathway such that the tissue anchor 96 is passed through and bears against a separate tissue layer 76 and then through a skin incision 88. Alternatively, the sutures 156 and 158 can first be passed by themselves through the skin incisions 86 and 88, respectively, and the tissue anchors 96 and 98 can be applied over the sutures 156 and 158 to bear against the tissue layers 76 and 78, respectively. In a related embodiment, the various sling embodiments can be used without tissue anchors.

Tension can be applied by pulling on the suture ends of sutures 156 and 158, respectively while applying pressure against the subcutaneous tissue anchors 96 and 98, thereby decreasing the spacings 162 and 164. Tension on sutures 156 and 158 can be released to lengthen spacings 162 and 164 by exposing and manipulating the tissue anchors 96 and 98.

It will be understood that the tissue layers 72, 74, 76, and 78 may comprise a muscle layer, fascia or transobturator membrane. Tissue layers 72 and 76 may be the same or a different tissue layer, and tissue layers 74 and 78 may be the same or a different tissue layer. The particular locations of skin incisions 86 and 88 and the respective tissue anchors 96 and 98 may include obturator, abdominal, pelvic, perineal and rectal regions.

The tissue anchors 632, 634, 96, and 98 may take any of the forms disclosed in the above-referenced '002 patent and in U.S. Patent Application Publication Nos. 2005/0004576 and 2006/0089525.

A wide variety of other specific embodiments of the invention employing adjustment mechanisms bridging a gap between the sling intermediate ends 36, 38 and 46, 48 to adjust spacings 162 and 164 are contemplated. In the following embodiments, the adjustment actuator acts upon the sling end portion adjustment mechanisms 102 and 104 by percutaneous direct access to an adjustment tool or transcutaneous transmission of adjustment commands to an adjustment control of the adjustment mechanism. In these embodiments, both shortening and lengthening of the length of the adjustment spacings 162 and 164 for increasing and decreasing sling tension are contemplated by these embodiments.

Figure 12:
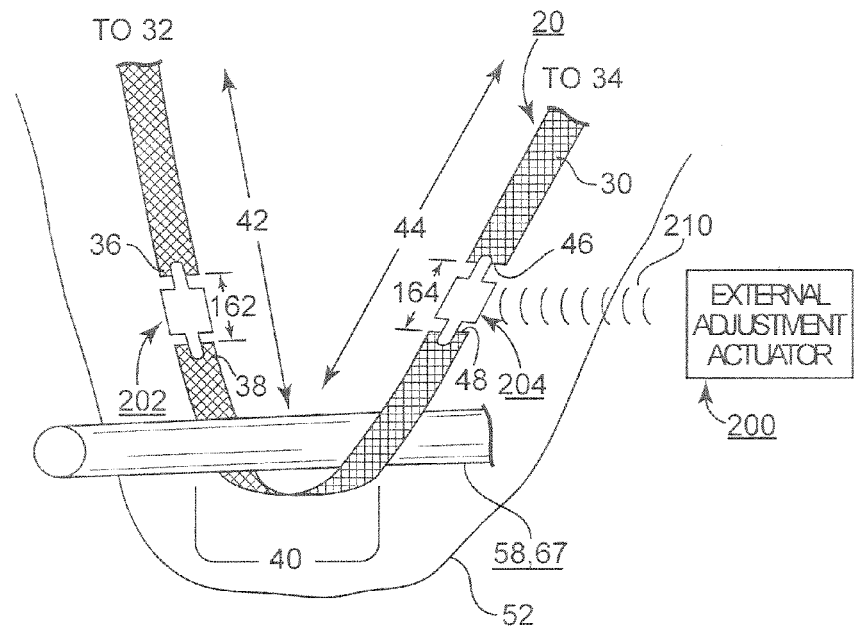
FIGS. 12 and 13 are schematic illustrations of further preferred embodiments of an adjustable tension sling having sling tension adjustment mechanisms bridging adjustment spacings in the sling end portions adapted to be adjusted by commands transcutaneously transmitted from an external adjustment actuator to increase and/or decrease the tension applied locally to the urethra.

Referring to FIG. 12, adjustment mechanism 202 is disposed across the adjustment spacing 162 and affixed to sling intermediate ends 36 and 38, and adjustment mechanism 204 is disposed across the adjustment spacing 164 and affixed to sling intermediate ends 46 and 48. An external adjustment actuator 200 is depicted brought into proximity to or applied against the skin 52 for generating an adjustment command 210 that is communicated transcutaneously through the skin 52 and underlying fat, tissue and fascia to adjustment mechanism 204. It will be understood that the external adjustment actuator 200 may also be brought into proximity to the skin 52 for generating a similar adjustment command communicated transcutaneously through the skin 52 and underlying fat, tissue and fascia to adjustment mechanism 202. The adjustment mechanisms 202 and 204 comprise electro-mechanical systems or elements or materials that respond to the transmitted command 210 to effect the adjustment in length of the adjustable spacings 162 and 164. In a related embodiment, mechanisms 202 and 204 are shape memory alloy (e.g. nitinol) elements that contract in size and expand in size depending on the stimulus.

Figure 13:
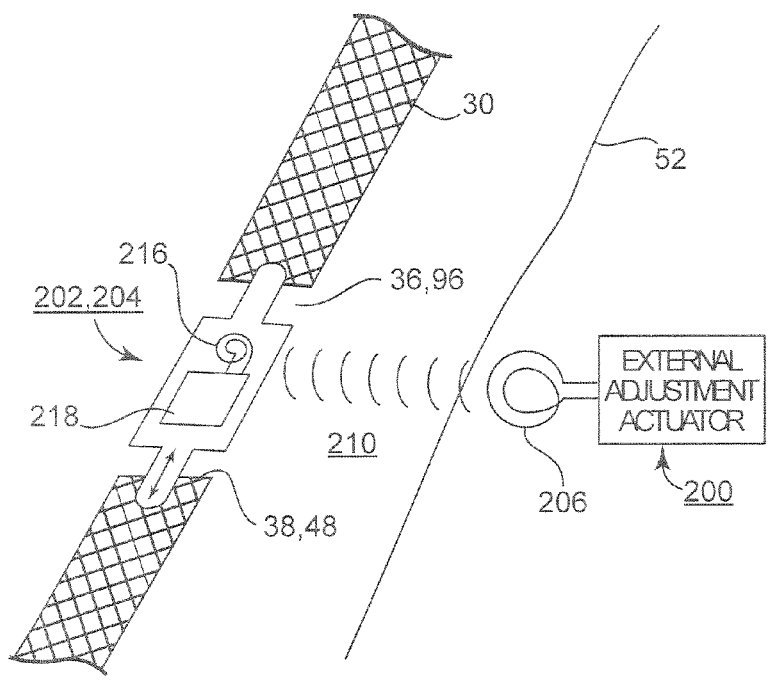
Figure 14:
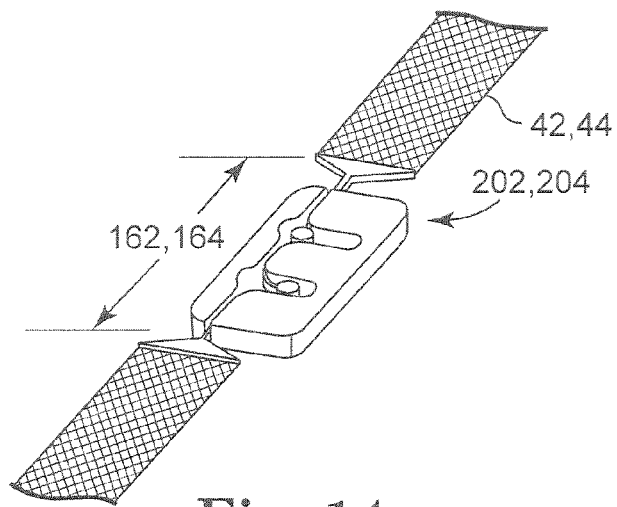
FIGS. 14-17 are schematic illustrations of further preferred embodiments of an adjustable tension sling having sling tension adjustment mechanisms bridging adjustment spacings in the sling end portions comprising serpentine roller adjustment mechanisms that adjusts the length of an adjustment spacing in response to an externally applied command.

In one variation of this embodiment depicted in FIG. 13, the external adjustment actuator 200 is an RF signal generator that generates an RF signal 210 through antenna 206 applied to the patient's skin as command 210. The adjustment mechanisms 202 and 204 each incorporate an RF antenna 216 that receives the RF signal and apply the received signal to internal electro-mechanical drive mechanism 218 for extending or contracting the length of the adjustment mechanisms 202 and 204.

Alternatively, the RF signal 210 is a power signal that is received by antenna 216 to generate a current that is applied to resistive heating elements or heat responsive elements forming the electro-mechanical drive mechanism 218 of each of adjustment mechanisms 202 and 204. For example, the electro-mechanical drive mechanism 218 of the adjustment mechanisms 202 and 204 may comprise chambers holding a heat responsive fluid that expands as heat is applied, and the expanded fluid drives pistons in the chambers to increase the overall length of the adjustment mechanisms 202 and 204. Or, the electro-mechanical drive mechanism 218 may comprise a heat responsive bi-metal strip that is heated by the received current and expands or contracts in length to expand or contract the length of the adjustment mechanisms 202 and 204.

Alternatively, the external adjustment actuator 200 generates a pulsed or steady magnetic field as the command 210. The adjustment mechanisms 202 and 204 incorporate magnetic responsive switches, e.g., reed switches or MAGFETs within the electro-mechanical drive mechanism 218 that switch states and operate the electro-mechanical drive mechanism 218 to extend or contract the length of the adjustment mechanisms 202 and 204.

Alternatively, the external adjustment actuator 200 is simply a heating or chilling pad that is applied to the skin to locally heat or cool the underlying tissue and the adjustment mechanisms 202 and 204 to expand or contract a heat responsive element or material that is incorporated into the adjustment mechanisms 202 and 204. The heating and/or cooling of the heat responsive element or material extends and/or contracts the length of the adjustment mechanisms 202 and 204.

Alternatively, the sling tension adjustment mechanisms 202 and 204 comprise light responsive elements, and the external adjustment actuator 200 comprises a light source (laser or diode) that emits light pulses of a light frequency capable of penetrating the skin and underlying fat layers and fascia as the command 210 that the light responsive elements are capable of detecting. An electro-mechanical drive mechanism 218 responds to the output signals of the light detectors to adjust the length of the adjustment mechanisms 202 and 204.

FIGS. 14-17 are schematic illustrations of a serpentine roller that may be incorporated into the adjustment mechanisms 202 and 204 to adjust the length of the adjustment spacings 162 and 164. The intermediate ends 36, 38 and 46, 48 are attached to ends of a band 230 that extends through a channel 226 of the housing 220, the channel 226 including two chambers 222 and 224. The band 230 extends around roller 232 disposed in chamber 222 and roller 234 disposed in chamber 224. The lengths of the adjustment spacings 162, 164 depend on the location of the rollers 232 and 234 in the respective channels 222 and 224.

Figure 15:
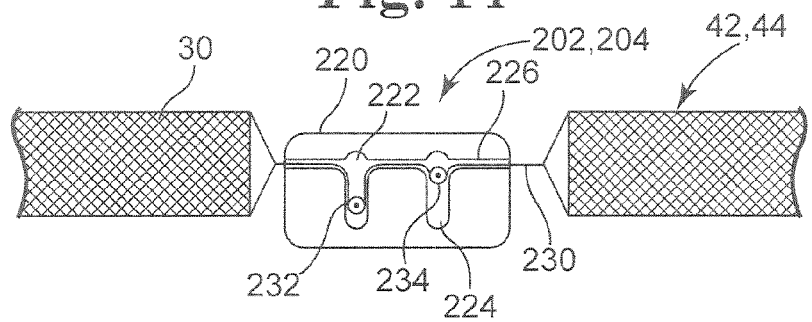
Figure 16:
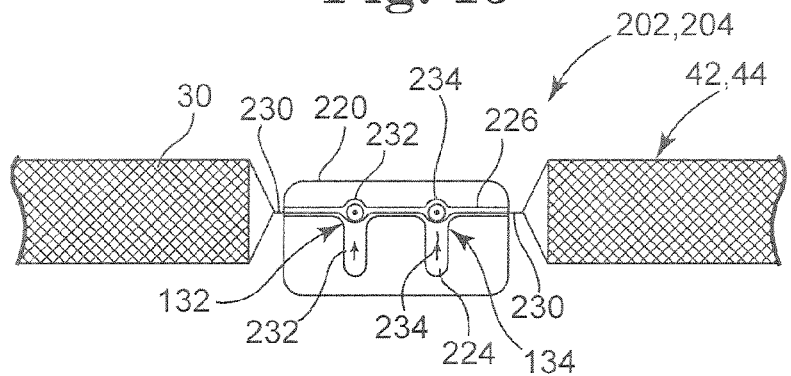
Figure 17:
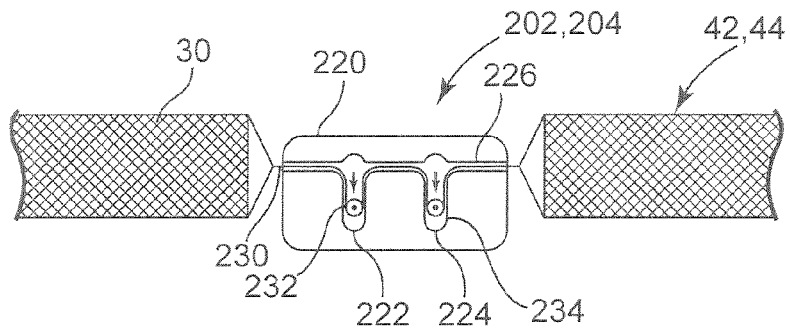

A maximum length of the adjustment spacings 162, 164 is obtained with the rollers 232 and 234 disposed substantially out of the respective channels 222 and 224 as shown in FIG. 16. A minimum length of the adjustment spacings 162, 164 is obtained with the rollers 232 and 234 disposed fully within the respective channels 222 and 224 as shown in FIG. 17. An intermediate or neutral length of the adjustment spacings 162, 164 is obtained with the roller 232 disposed fully within the respective channels 222 and the roller 234 disposed substantially out of the respective channel 224 as shown in FIG. 15. The sling 20 would be implanted with the rollers 232 and 234 disposed in the neutral position of FIG. 15, and later adjustments to the position of FIG. 16 or FIG. 17 would be made with an external adjuster applied to the patient's skin 52. It is contemplated that movement of the rollers 232 and 234 would be controlled by an electro-mechanical interface between the rollers 232 and 234 and any mechanism responsive to commands 210 generated by the external actuator 200 as described above.

Figure 18:
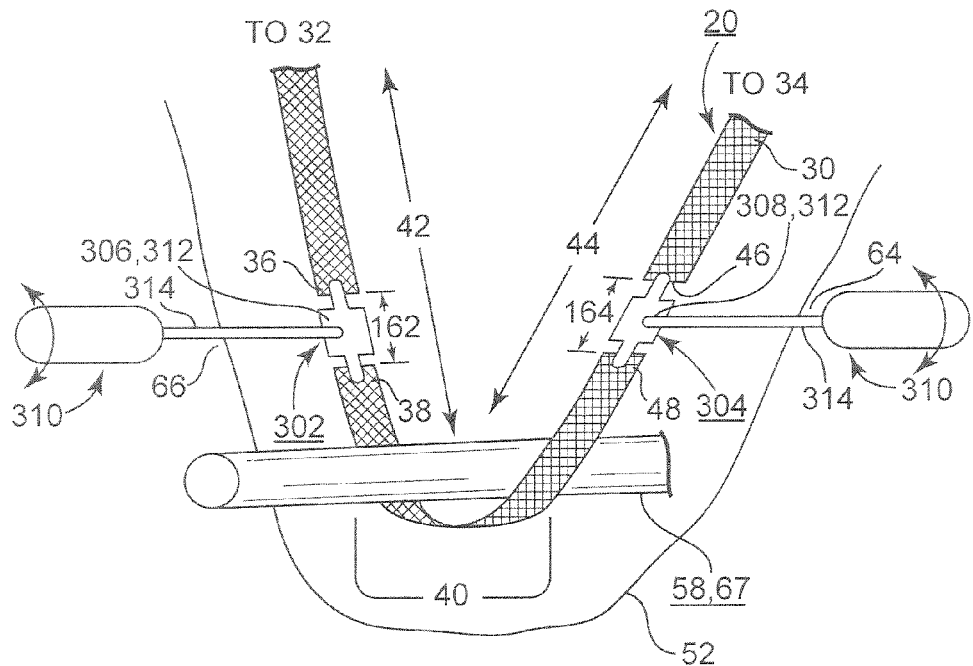
FIG. 18 is a schematic illustration of a further preferred embodiment of an adjustable tension sling, wherein the adjustment mechanism is adjusted by an external adjustment actuator comprising an external adjustment actuator having an engaging end at the end of a shaft adapted to be percutaneously advanced into engagement with the adjustment mechanism to adjust the length of an adjustment spacing between intermediate sling ends in the sling end portions.

In further embodiments illustrated schematically in FIG. 18, the external adjustment actuator 310 has an actuator-engaging end 312 at the end of a shaft 314. The tension adjustment mechanisms 302 and 304 are shaped with actuator end receptacles 306 and 308, respectively, that can be manually palpated through the skin 52. The actuator engaging end 312 and shaft 314 can be inserted percutaneously through skin incisions 64 and 66 to fit the actuator engaging end 312 into the actuator end receptacles 306 and 308. The external adjustment actuator 310 is depicted in engagement (at separate times) with both actuator end receptacles 306 and 308 in FIG. 18. Various rotatable mechanisms within the tension adjustment mechanisms 302 and 304 are contemplated that can be rotated by manual rotation of the external adjustment actuator 310 in one direction to shorten the sling end portions 42 and 44 together to increase sling tension and that can be rotated by manual rotation of the external adjustment actuator 310 in the other direction to lengthen the sling end portions 42 and 44 to separate apart to decrease sling tension. The actuator engaging end 312 is shaped to both penetrate tissue and to have mating surfaces for engaging the end receptacles 306 and 308 to enable rotation in both directions.

The tension adjustment mechanisms 302 and 304 depicted in FIGS. 19-22 each comprise a bobbin 316 mounted for rotation in a receptacle of a housing 320 fixed at one end to the sling intermediate end 36, 46, the bobbin 316 shaped with the actuator end receptacles 306, 308 extending axially into one side of the bobbin 316. A band or strand 330 extends from a fixed connection with the other sling intermediate end 38, 48 into a channel 322 in housing 320 and around a groove of the bobbin 316 to a fixed coupling with the bobbin 316. The bobbin 316 is formed with three detents 332, 334, 336 spaced apart around its circumference, and the free end of a catch 324 fixed at its other end to housing 320 engages one of the detents 332, 334, 336.

Figure 19:
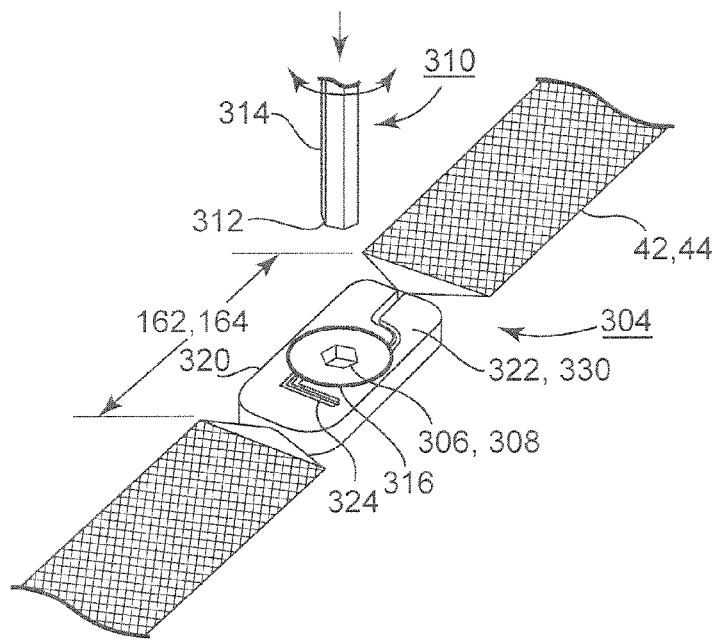
FIG. 19 is a schematic illustration of one embodiment of the sling tension adjustment mechanisms of FIG. 18 employing a rotatable bobbin, a fixed catch and detents around the bobbin circumference.
Figure 20:
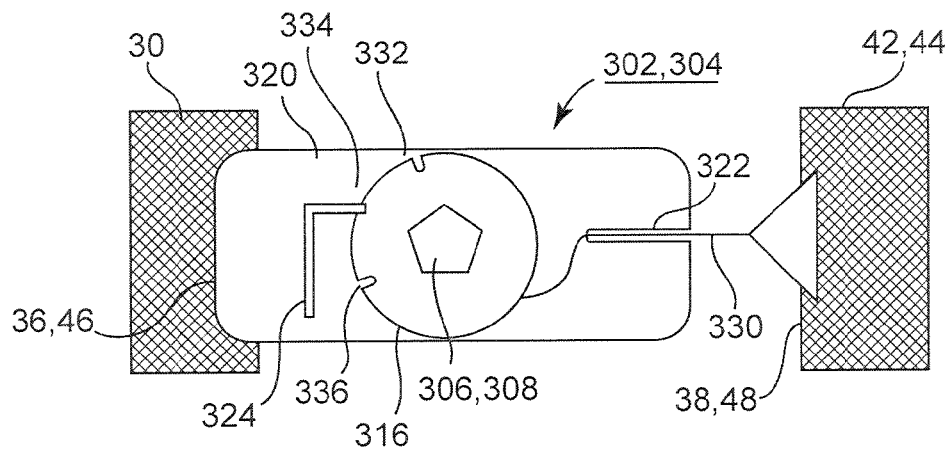
FIGS. 20-22 are schematic illustrations of the adjustment mechanism of FIG. 19 that adjusts the length of an adjustment spacing in response to an externally applied external adjustment actuator.

In this embodiment, the actuator end receptacles 306, 308 have a five sided socket shape, and the engaging end 312 of the shaft 314 of external adjustment actuator 310 is also shaped as a mating five-side wrench having a distal point and is shown poised to be inserted into the actuator end receptacle 306, 308 in FIG. 19. The neutral position of the bobbin 316 at the time that the sling 20 is implanted is depicted in FIG. 20. At a later date, the external adjustment actuator 310 can be used to engage and rotate the bobbin 316 to either increase or decrease the amount of the band or strand 330 taken up on the bobbin groove and to thereby shorten or extend, respectively, the adjustment spacing 162, 164, and tighten or loosen, respectively, the sling 20 and increase or decrease, respectively, tension applied by the sling central support portion 40 to the urethra 58 (or anus).

Figure 21:
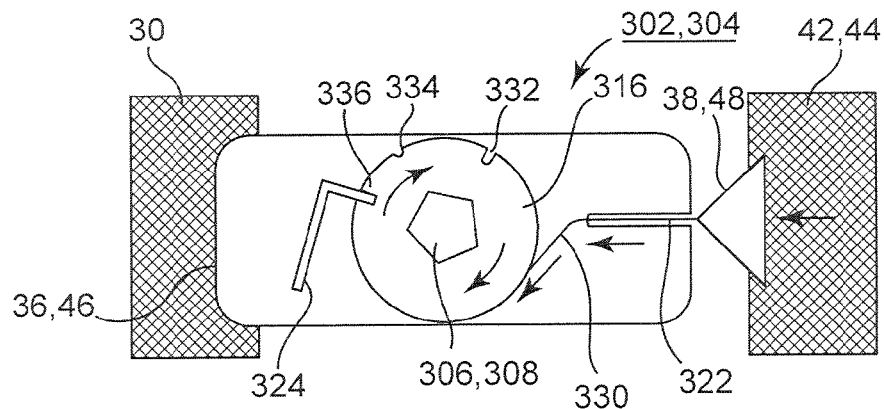
Figure 22:
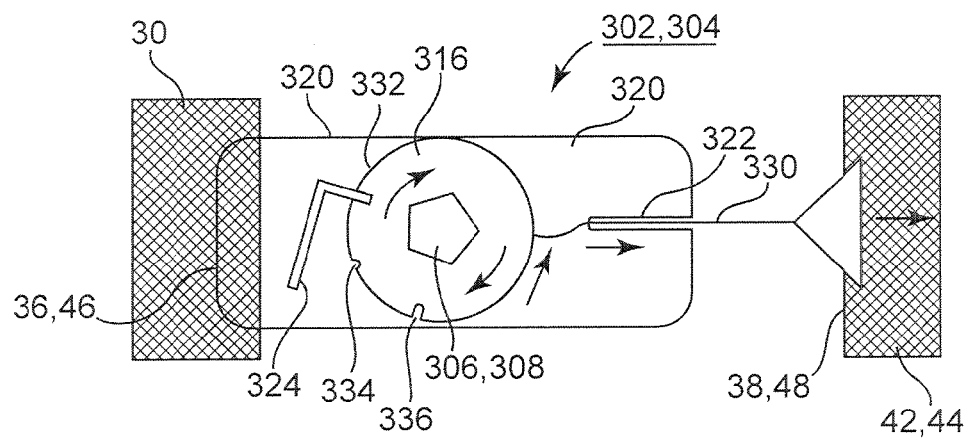

As shown in FIG. 21, a minimum length of the adjustment spacing 162, 164 is obtained by clockwise rotation of the bobbin 316 to move the catch end 324 out of detent 334 and along the outer edge of the bobbin 316 until the catch end engages detent 336. As shown in FIG. 22, a maximum length of the adjustment spacing 162, 164 is obtained by counter-clockwise rotation of the bobbin 316 to move the catch end 324 out of detent 334 and along the outer edge of the bobbin 316 until the catch end engages detent 332.

Figure 23:
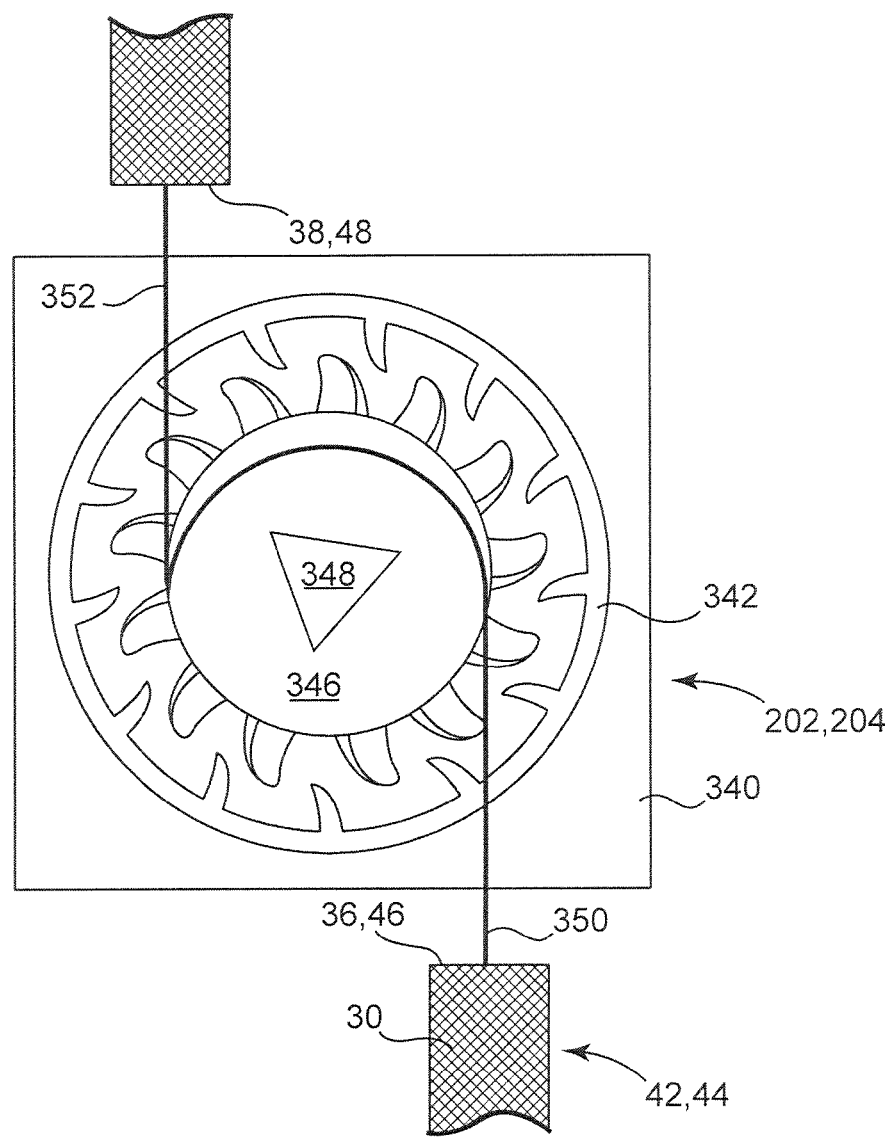
FIG. 23 is a schematic view in section of a variation on the embodiment of FIG. 19, wherein the adjustment mechanism housing supports a rotatable bobbin surrounded by a fixed detent ring providing an increased range of adjustments.
Figure 24:
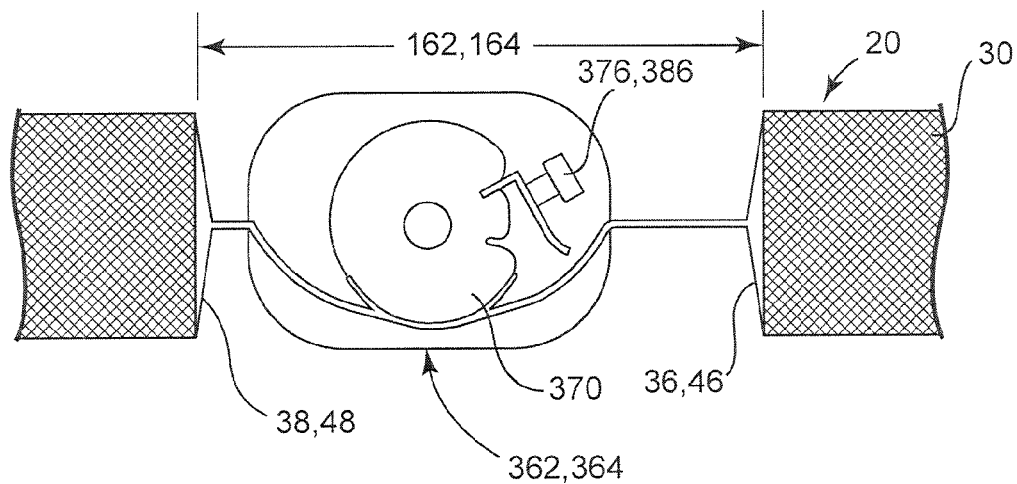
FIGS. 24-26 are schematic plan illustrations of a further embodiment of the adjustment mechanism of FIG. 18, wherein a dual cam assembly having a first cam operates to decrease the adjustable spacings from the neutral length illustrated in FIG. 24 to the contracted length of FIGS. 25A-25D and a second cam operates to increase the adjustable spacings to the extended length of FIGS. 26A-26D.
Figure 26A:
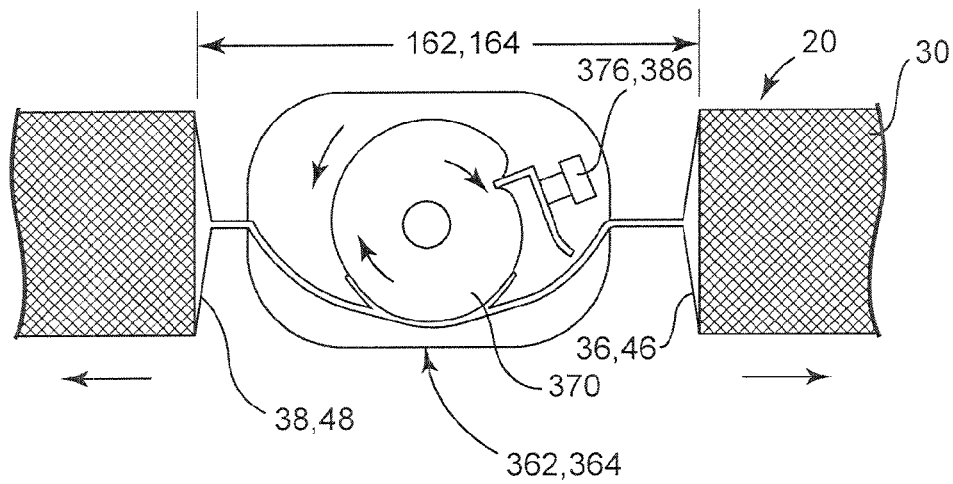

An alternative detent arrangement of the bobbin and housing is depicted in FIG. 23. In this variation, the housing 340 supports a rotatable bobbin 346 surrounded by a fixed detent ring 342. The actuator-engaging receptacle 348 is shaped to receive an actuator end shaped like a three-sided Keith needle. A first band or strand 350 extends from a fixed end about a portion of the circumference of the bobbin 346 and is coupled at its other end to the intermediate end 36, 46 of the sling 20 formed of mesh 30. A second band or strand 352 extends from a fixed end about a portion of the circumference of the bobbin 346 and is coupled at its other end to the intermediate end 38, 48 of the sling 20. The rotatable bobbin 346 and fixed detent ring 342 further comprise a plurality of flexible tabs or teeth that interlock like gear teeth.

Again, a neutral position of the bobbin 346 is established at the time that the sling 20 is implanted is depicted. At a later date, the Keith needle style external adjustment actuator 310 can be used to engage the receptacle 348 and rotate the bobbin 346 clockwise to decrease or counterclockwise to increase the amount of the bands or strands 350, 352 taken up on the bobbin grooves. The clockwise and counterclockwise bobbin rotations thereby extend or shorten, respectively, the adjustment spacing 162, 164, and loosen or tighten, respectively, the sling 20 and decrease or increase, respectively, tension applied by the sling central support portion 40 to the urethra 58.

Figure 25A:
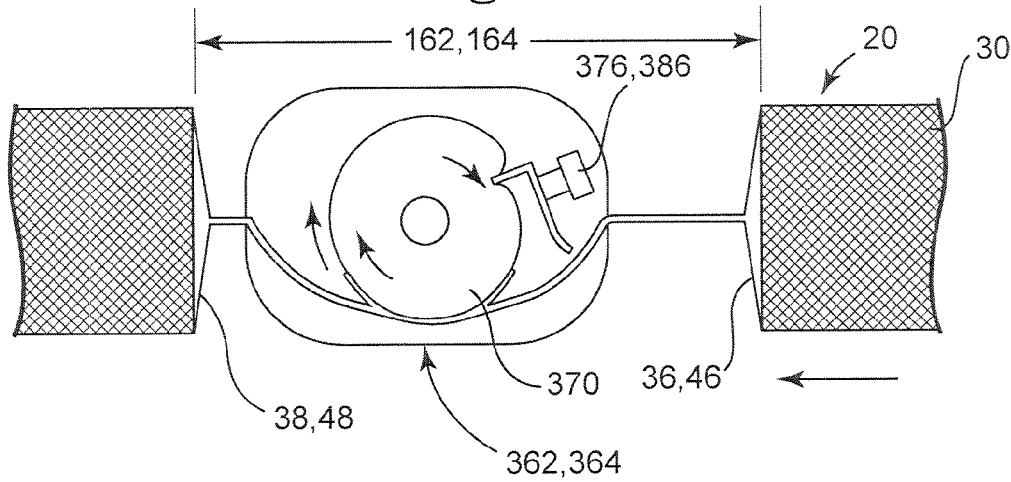
Figure 25D:
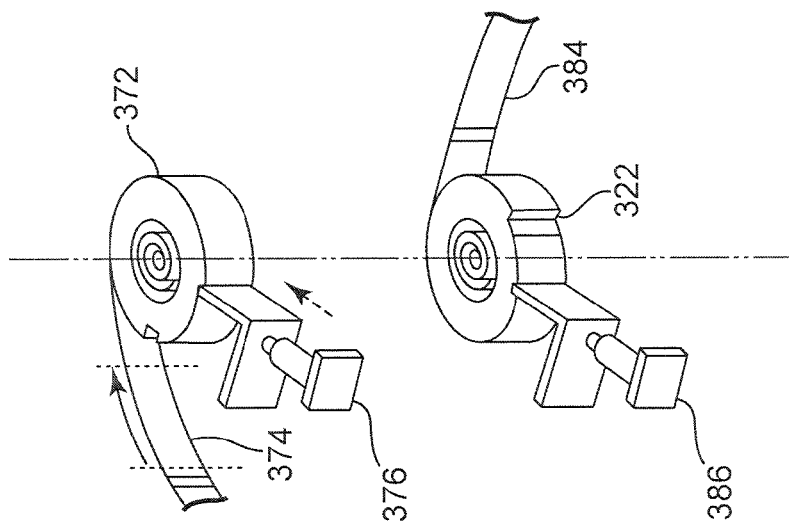
Figure 25C:
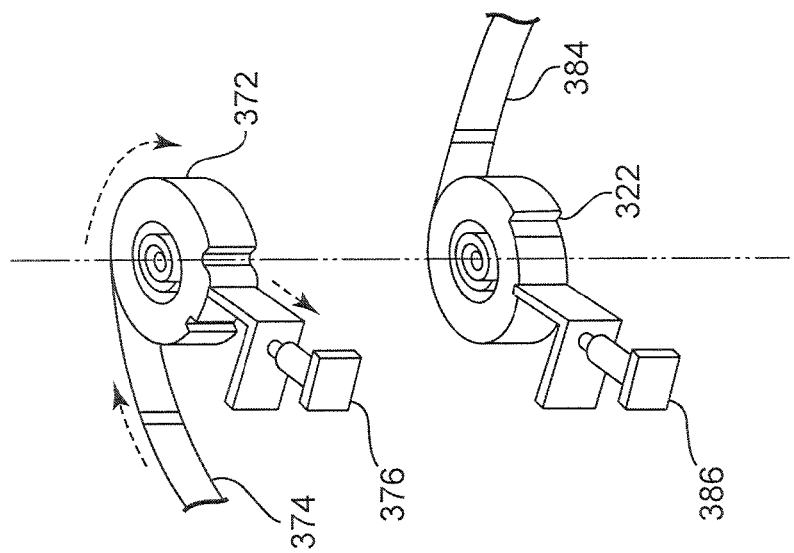
Figure 25B:
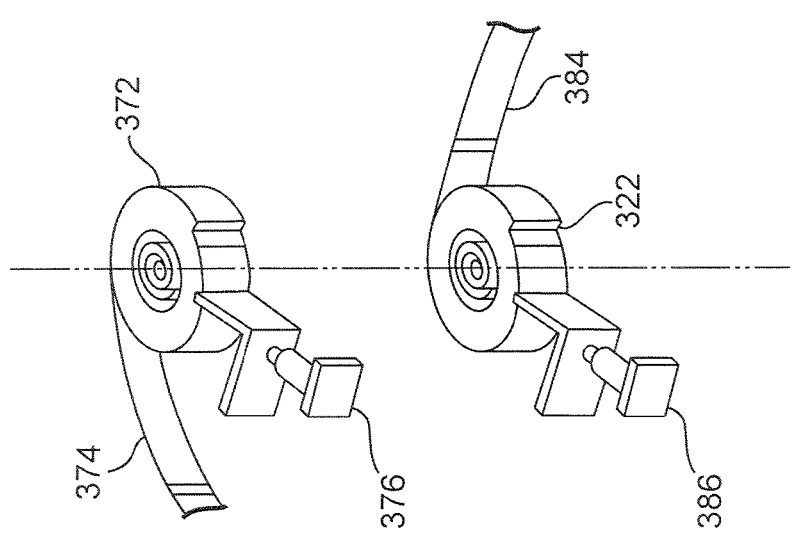
Figure 26D:
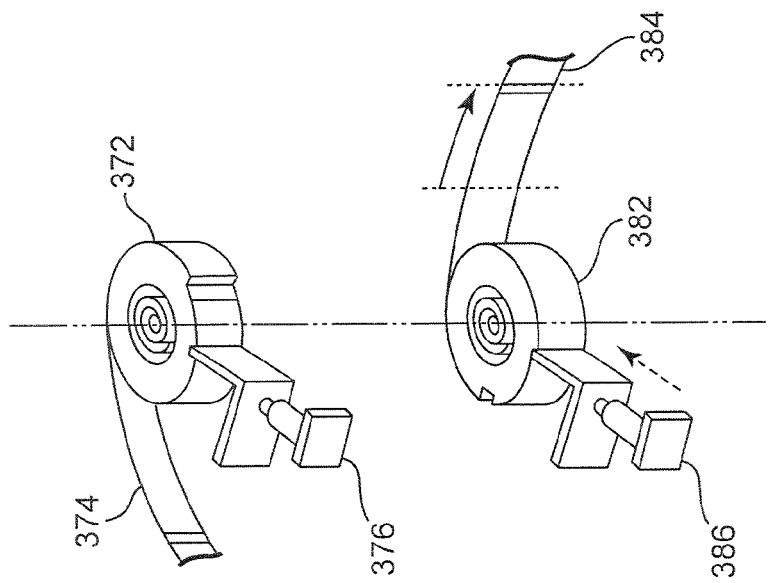
Figure 26C:
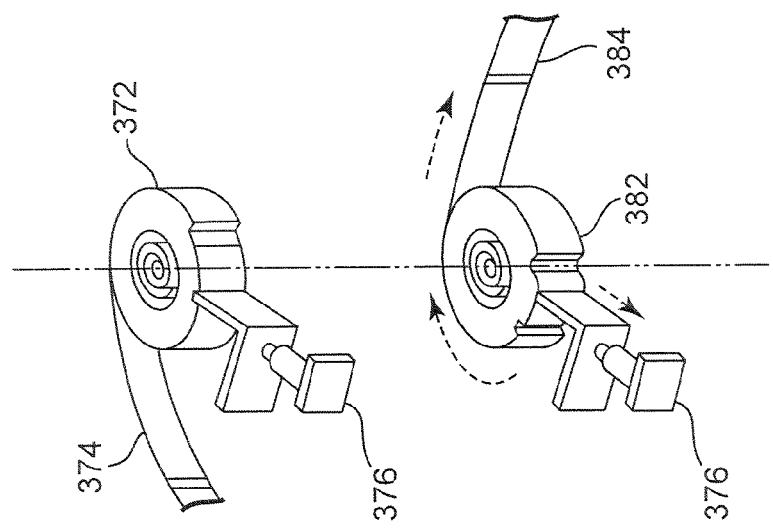
Figure 26B:
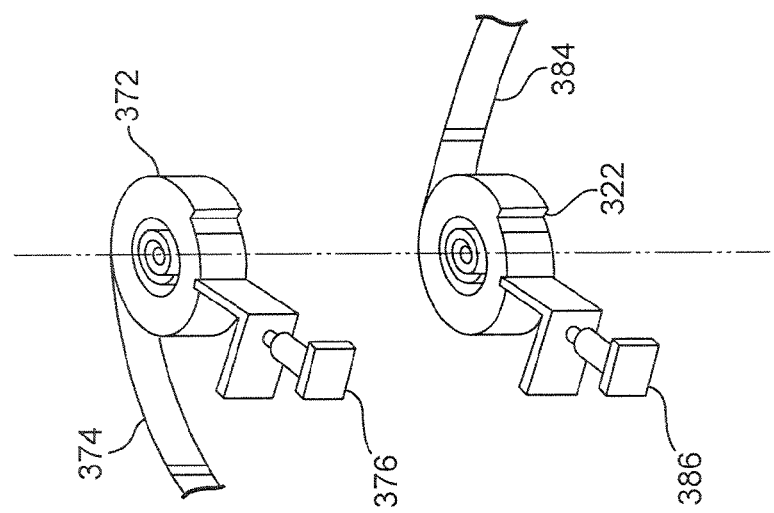

An alternative dual cam adjustment mechanism 362, 364 is depicted in FIGS. 24, 25A-25D, and 26A-26D disposed in the adjustable spacings 162, 164. The tension adjustment mechanisms 362, 364 each comprise a dual cam assembly 370 comprising a first cam 372 coupled to first tether 374 and a first cam follower 376 and a second cam 382 coupled to a second tether 384 and second cam follower 386. The ends of the first and second tethers 374 and 384 are coupled to the sling intermediate ends 36, 46, and 38, 48 respectively. The first cam 372 rotated with respect to cam follower 376 operates to decrease the adjustable spacings 162, 164 from the neutral length of FIG. 24 to the contracted length of FIG. 25A as shown in FIGS. 25B-25D. The second cam 382 rotated with respect to cam follower 38 operates to increase the adjustable spacings 162, 164 from the neutral length of FIG. 24 to the contracted length of FIG. 26A as shown in FIGS. 26B-26D. The external adjustment actuator 310 (FIG. 18) is operated to engage either the first or the second cam 372 or 382 to increase or decrease sling tension, respectively. Any suitable socket and actuator configuration may be employed for effecting selective rotation of the cams.

Figure 27:
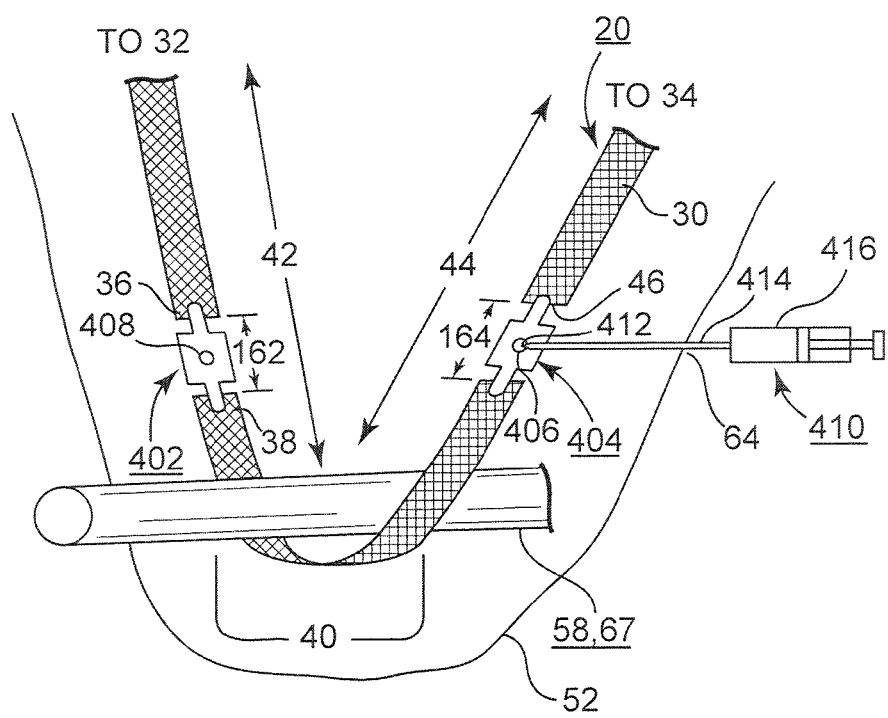
FIG. 27 is a schematic illustration of a further preferred embodiment of the adjustable tension sling, wherein the adjustment mechanism is adjusted by an external fluid delivery/withdrawal syringe adapted to be percutaneously advanced into engagement with a fluid port of the adjustment mechanism to adjust the length of the adjustment spacing between intermediate sling ends in the sling end portions.
Figure 28:
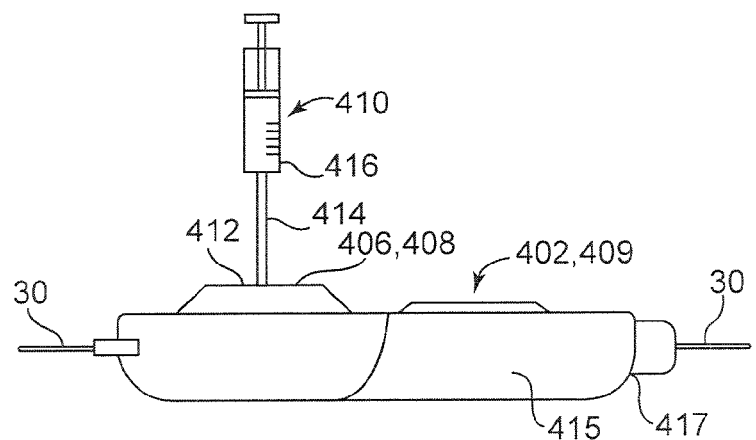
FIGS. 28-31 are schematic plan side or top views illustrating one, single action, hydraulic cylinder, adjustment mechanism of FIG. 27 having a fluid chamber adapted to be filled or be emptied of fluid using the syringe of FIG. 27 to adjust the length of the adjustment spacing between intermediate sling ends in the sling end portions.

In yet further embodiments of the second category depicted schematically in FIG. 27, the external adjustment actuator is a syringe 410 or the like that is inserted percutaneously through a skin incision to engage a port 406, 408 of a fluid retaining chamber of the sling tension adjustment mechanism 402, 404.

Figure 29:
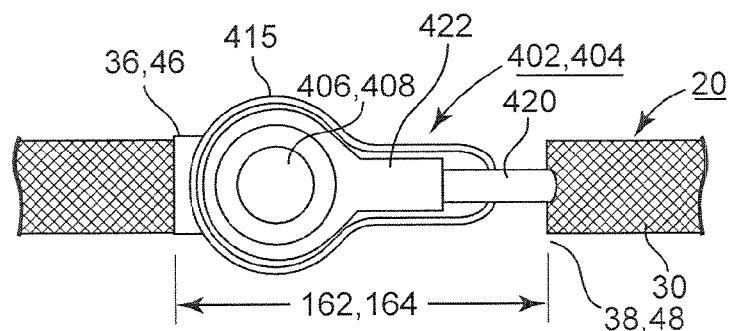
Figure 30:
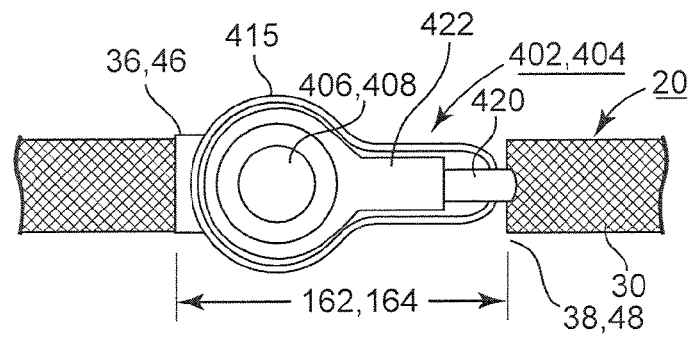
Figure 31:
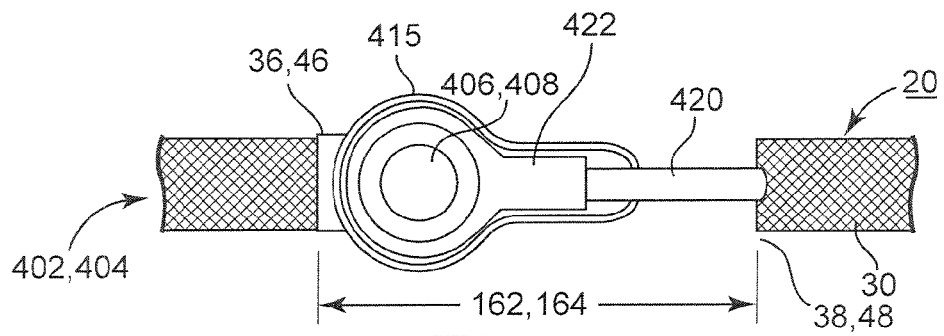
Figures 32, 33:
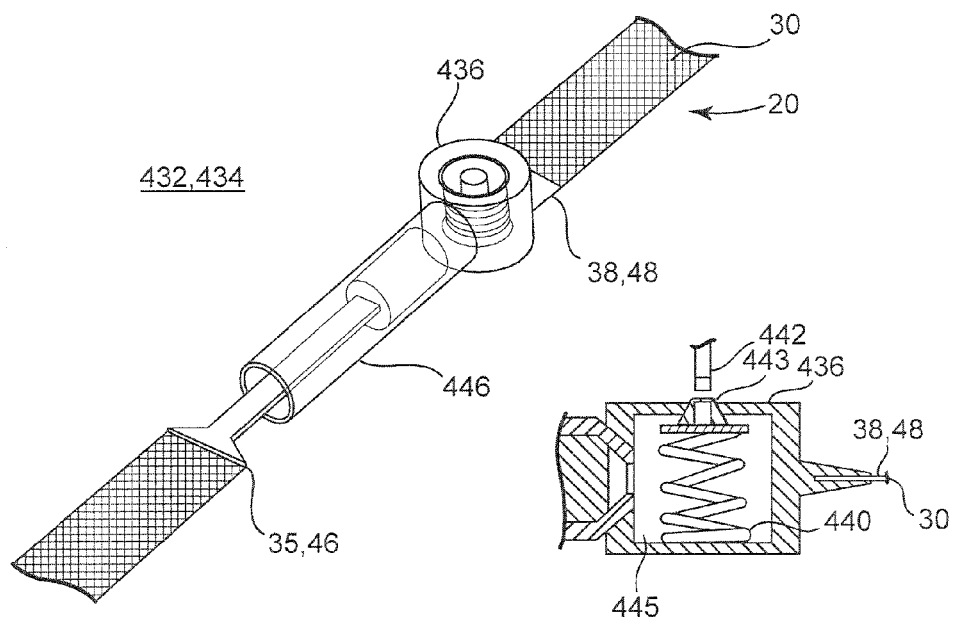
FIGS. 32-36 are schematic perspective, side or top views in partial section illustrating a further single action, hydraulic cylinder, adjustment mechanism of FIG. 27 having a fluid chamber adapted to be filled or be emptied of fluid using the syringe of FIG. 27 to adjust the length of the adjustment spacing between intermediate sling ends in the sling end portions.
Figure 34:
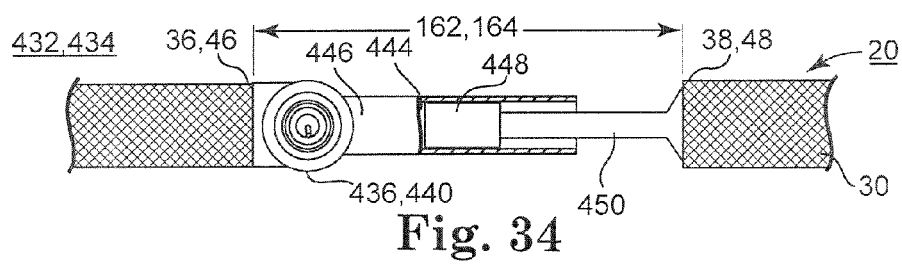

In the embodiment depicted in FIGS. 28-31, the port 406, 408 comprises a penetrable, resealable septum, and a needle stop may be included within the fluid chamber opposite the resealable septum to prevent needle perforation of the wall of the fluid retaining chamber within the outer housing 415. The port 406, 408 is coupled to sling intermediate end 36, 46, and a rod 420 is coupled at its free end to the sling intermediate end 38, 48. The port 406, 408 accesses a cylinder within housing 422 so that the fluid delivered through the septum of the port 406, 408 is also delivered into the cylinder. A piston coupled to the rod 420 (which may simply be an enlarged diameter end of rod 420) is also enclosed within the cylinder of housing 422. Rod 420 extends through a C-shaped opening 417 in the end of outer housing 415 that guides but does not inhibit movement of rod 420. The adjustment spacing 162, 164 is adjusted by injecting or withdrawing fluid from the fluid chamber to laterally extend or retract the piston mounted rod 420 to increase or decrease the adjustment spacing 162, 164 as shown in FIGS. 29-31.

A variation on this embodiment is depicted in FIGS. 32-36, wherein a sling tension adjustment mechanism 432, 434 is substituted for the sling tension adjustment mechanism 402, 404 of FIGS. 27-31. In this variation, the port 436 is formed with a syringe needle interlock 443, and the syringe has a special interlocking tip 442 that opens and enters the interlock 443 to deliver or withdraw fluid from or to the syringe chamber. The port 436 is coupled to a housing 446 enclosing a cylinder or fluid chamber 444 that the fluid is delivered into. The interlock 443 is spring loaded by spring 440 within the port chamber 445. A piston 448 is also enclosed within the housing 446 and coupled to a rod 450 extending from the housing end. The port 436 is coupled to sling intermediate end 36, 46, and the rod 450 is coupled at its free end to the sling intermediate end 38, 48.

Figure 35:
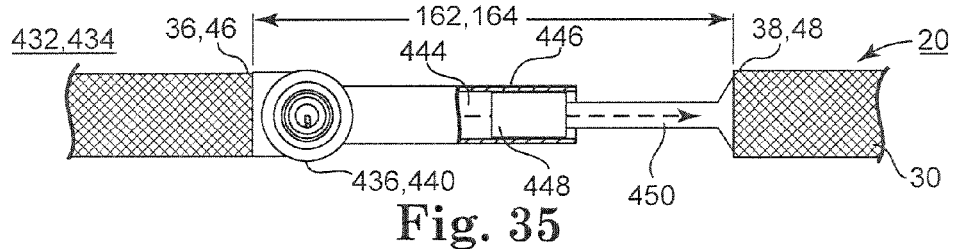
Figure 36:
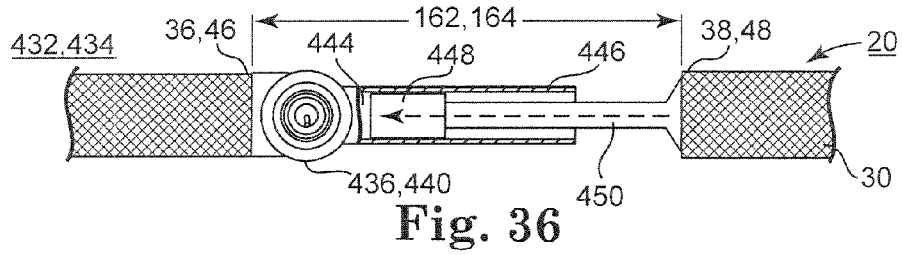
Figure 37:
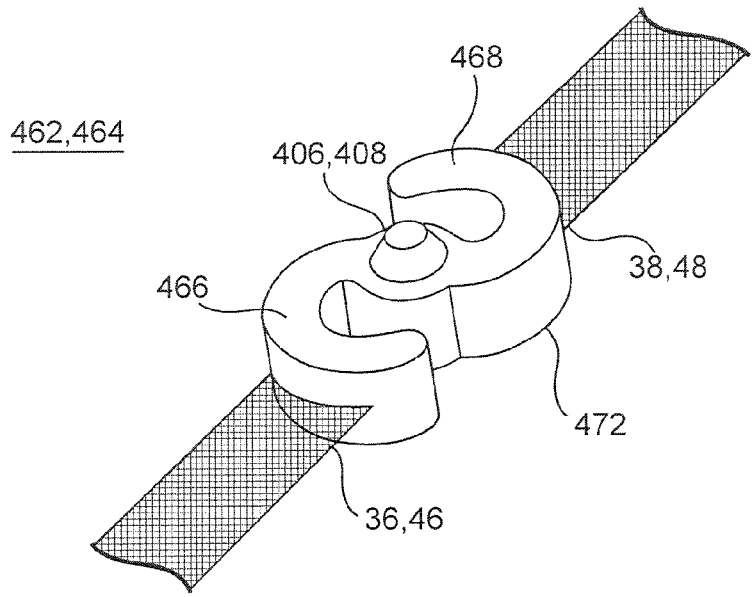
FIGS. 37-40 are schematic perspective or top views illustrating a still further single action, hydraulic adjustment mechanism of FIG. 27 having a fluid chamber adapted to be filled or be emptied of fluid using the syringe of FIG. 27 to adjust the length of the adjustment spacing between intermediate sling ends in the sling end portions.
Figure 38:
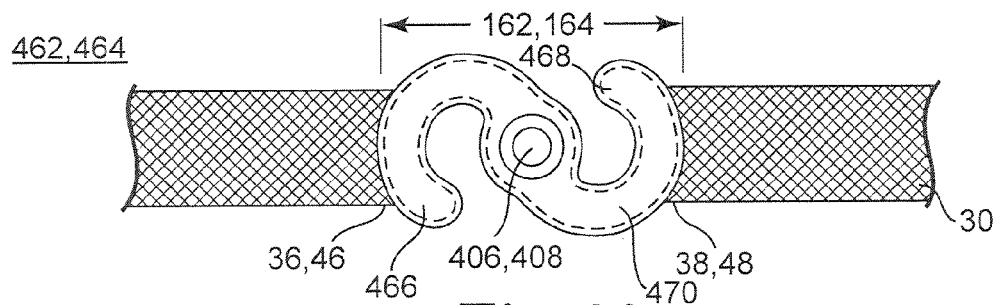

The volume of fluid delivered into the fluid chamber 444 dictates the position of the cylinder 448 within the chamber 444 and the extension of the rod 450. The adjustment spacing 162, 164 is therefore adjusted by injecting or withdrawing fluid from the fluid chamber 444 to laterally extend or retract the piston 448 and rod 450 to increase or decrease the adjustment spacing 162, 164 as shown in FIGS. 35-36.

The sling tension adjustment mechanisms 402, 404 and 432, 434 depicted in FIGS. 27-36 comprise single action, hydraulic pistons, wherein the fixed housing is coupled to one sling intermediate end and the movable rod end is coupled to the other intermediate sling end. It will be understood that the sling tension adjustment mechanisms 402, 404 and 432, 434 depicted in FIGS. 27-36 may be modified to function as dual action, hydraulic pistons having axially aligned and opposed pistons coupled to respective rods, and the rod free ends of each mechanism coupled to the sling intermediate ends 36, 46 and 38, 48.

A still further variation on this embodiment of the second category illustrated in FIG. 27 is depicted in FIGS. 37-40, wherein a sling tension adjustment mechanism 462, 464 is substituted for the sling tension adjustment mechanism 402, 404 of FIGS. 27-31. In this dual action variation, the external adjustment actuator is the syringe 410 or the like that is inserted percutaneously through a skin incision to engage a port 406, 408 of a fluid chamber 470 of the sling tension adjustment mechanism 462, 464. The port 406, 408 comprises a penetrable, resealable septum, and a needle stop may be included within the fluid chamber opposite the resealable septum to prevent needle perforation of the wall of the fluid chamber 470.

Figure 39:
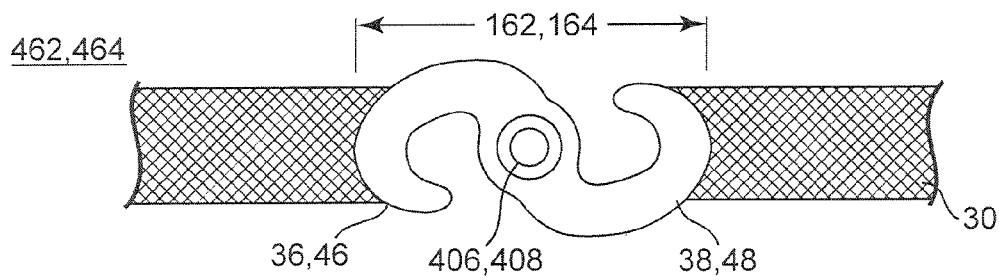
Figure 40:
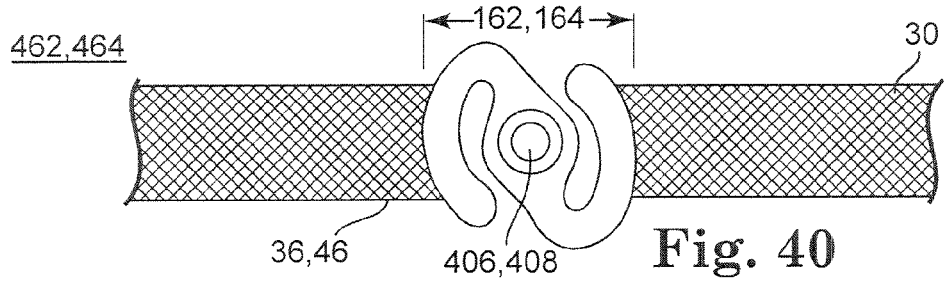

The S-shaped chamber housing 472 enclosing the fluid chamber 470 is shaped with opposed spiral arms 466 and 468 respectively coupled to sling intermediate end 36, 46 and end 38, 48. The housing 472 is formed of a material that is expandable as fluid volume and pressure increases as shown in FIG. 39 and contractible as fluid volume and pressure decreases as shown in FIG. 40. The adjustment spacing 162, 164 is therefore adjusted by injecting or withdrawing fluid from the fluid chamber 470 to laterally extend or retract the opposed spiral arms 466 and 468 to increase or decrease the adjustment spacing 162, 164 as shown in FIGS. 37-40.

In a further alternative variation (not shown), the arms 466 and 468 may be corrugated with one or more corrugation to function in the manner of bellows. In such case, the arms 466 and 468 may be spiral as depicted or extend in axial alignment and away from one another to increase or decrease the adjustable spacing 162, 164.

Figure 41:
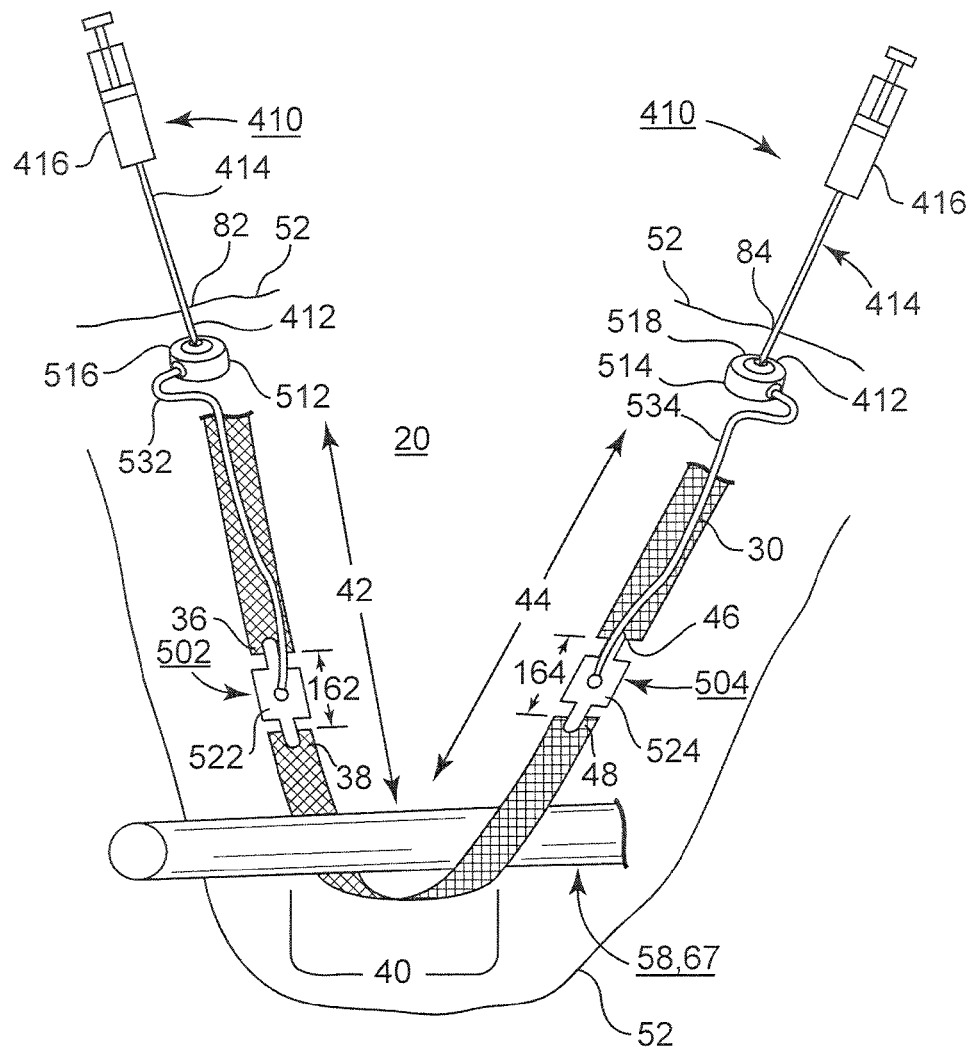
FIG. 41 is a schematic illustration of a further preferred embodiment of the adjustable tension sling, wherein the adjustment mechanism is adjusted by an external fluid delivery/withdrawal syringe adapted to be percutaneously advanced into engagement with a fluid port of a subcutaneously implantable fluid reservoir coupled to the adjustment mechanism to adjust the length of the adjustment spacing between intermediate sling ends in the sling end portions.

In certain further embodiments of the second category of the invention depicted schematically in FIG. 41, the sling tension adjustment mechanisms 502 and 504 comprise fluid reservoirs 512 and 514, housings 522 and 524, respectively, and tubes 532 and 534 extending between the fluid reservoirs 512 and 514 and housings 522 and 524, respectively, alongside the sling end portions 42 and 44, respectively. The housings 522 and 524 are coupled to the sling intermediate ends 36, 38 and 46, 48, respectively, and define the adjustment spacings 162 and 164, respectively.

The fluid reservoirs 512 and 514 are adapted to be implanted just below the skin 52 adjacent the skin incisions 82 and 84, respectively. Alternatively, the tubes 532 and 534 may extend through the skin incisions 82 and 84 to dispose the fluid reservoirs 512 and 514 outside the skin during the healing phase. In that case, the tubes 532 and 534 may be pulled upon to detach their distal ends from tube fittings on the housings 522 and 524 after tissue ingrowth into the mesh pores has secured the sling 20 in position. Tissue ingrowth should maintain the adjustment spacings 162, 164 even if the hydraulic fluid (saline) then escapes from fluid cylinders and chambers within the housings 522 and 524.

The fluid reservoirs 512 and 514 have respective fluid delivery/withdrawal ports 516 and 518 that may be percutaneously accessed by needle tip 412 of syringe 410 to introduce fluid into the fluid reservoir 512, 514 or to withdraw fluid from the fluid reservoir 512, 514 following implantation of the sling 20 to thereby adjust the amount of fluid in the fluid chambers of housings 522 and 524 and adjust the length of the adjustable spacings 162 and 164.

It will be understood that the housings 522, 524 may incorporate any of the adjustment mechanisms 402, 404 or 432, 434 or 462, 464 and variations thereof described above with the tubes 532, 534 and fluid reservoirs 512 and 514 substituted for the above-described fluid delivery/withdrawal ports.

Figure 46:
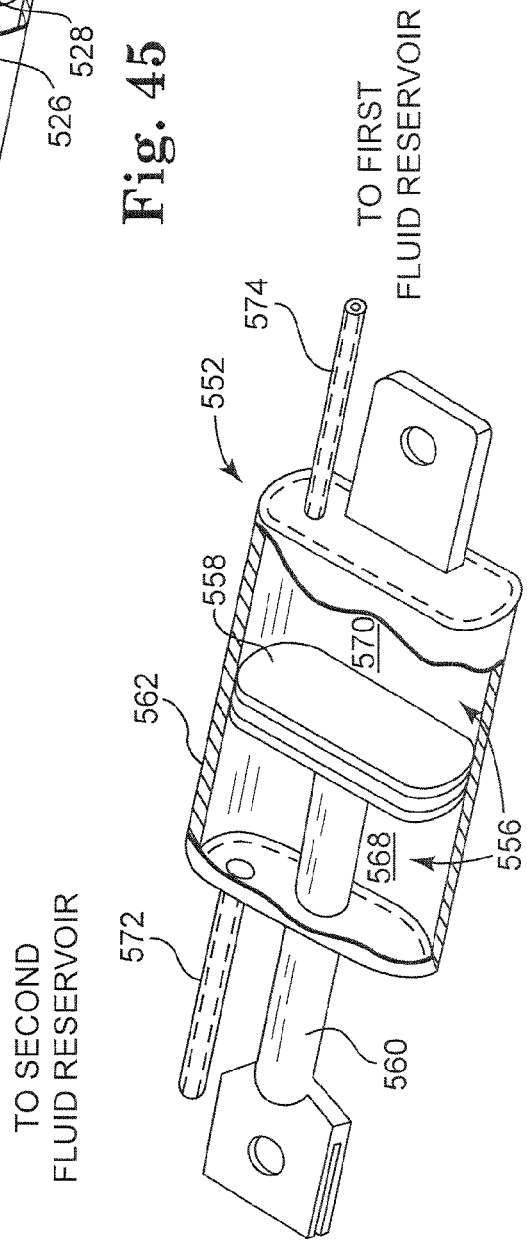
FIG. 46 is a perspective view in partial section of a dual action, hydraulic cylinder, adjustment mechanism adapted to be employed as depicted in FIG. 41 having fluid chamber portions adapted to be filled or be emptied of fluid using a syringe to add or withdraw fluid from subcutaneously implanted fluid reservoirs coupled to the fluid chamber portions to adjust the length of the adjustment spacing between intermediate sling ends in the sling end portions.

In FIGS. 42-45, alternative forms of adjustment housings 522 and 524 of the adjustment mechanisms 502, 504 and 502', 504' containing fluid chambers, pistons, and connecting rods are depicted in greater detail. The housing 522, 524 encloses a fluid chamber 526, a piston 528 and a rod 530 extending axially from one end of the housing 522, 524. In the particular single action cylinder designs depicted in FIGS. 42-45, the housing 522, 524 is elliptical in lateral cross-section having a major ellipse axis corresponding generally to the width of the mesh 30 of sling 20 so that the minor ellipse axis minimizes overall thickness of the sling 20. The housing wall 542, fluid chamber 526, and piston 528 may be shaped more oblong than elliptic as shown in FIG. 46. The sling intermediate end 36, 46 is coupled by thermoplastic rivets or sutures or the like to the stationary end of housing 522, 524, and the sling intermediate end 38, 48 is coupled by thermoplastic rivets or sutures or the like to the movable free end of rod 530 in each housing 522, 524. It will be understood that the piston 528 is formed with a ring or rings that provide a tight seal with the housing wall 542 defining the fluid chamber 526 to minimize fluid loss.

Figure 42:
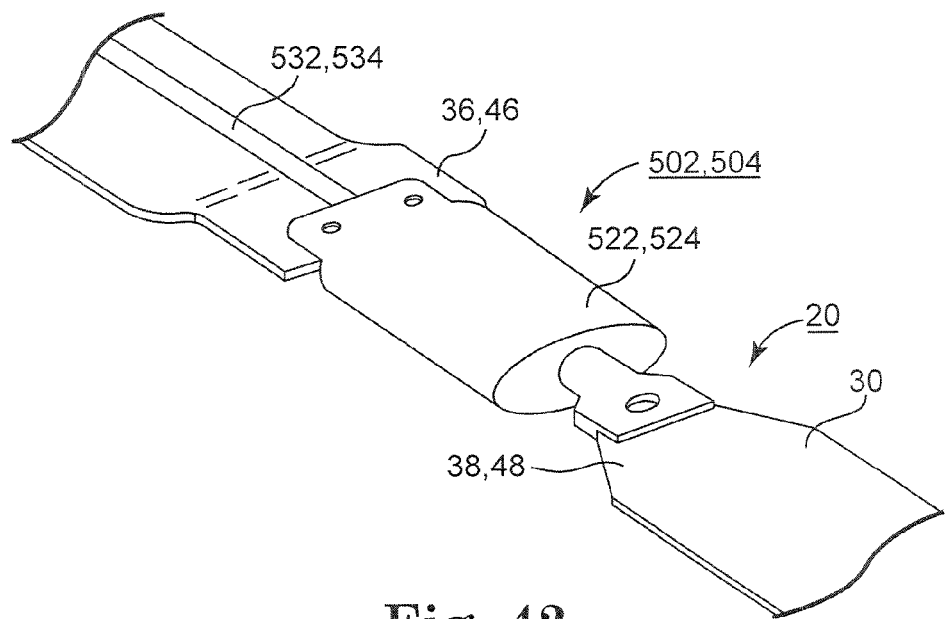
FIGS. 42-44 are schematic perspective views in partial section illustrating a single action, hydraulic cylinder, adjustment mechanisms of FIG. 41 having fluid chambers adapted to be filled or be emptied of fluid using the syringe of FIG. 41 to adjust the length of the adjustment spacing between intermediate sling ends in the sling end portions.
Figure 43:
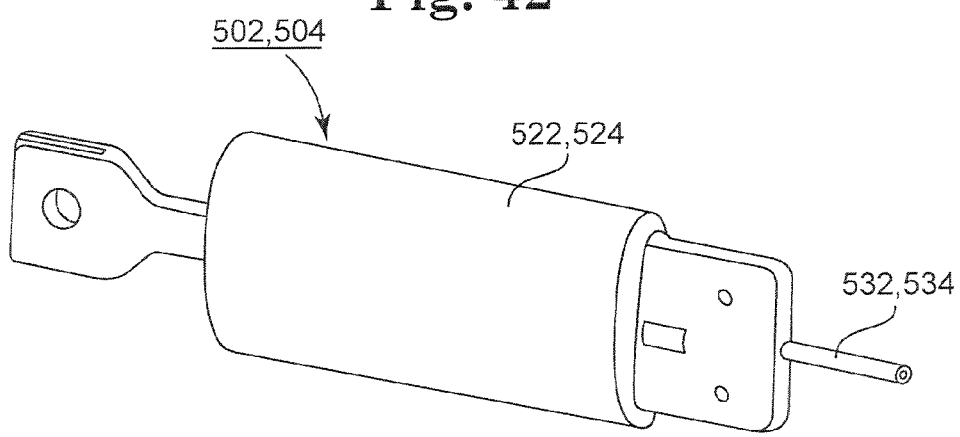
Figure 44:
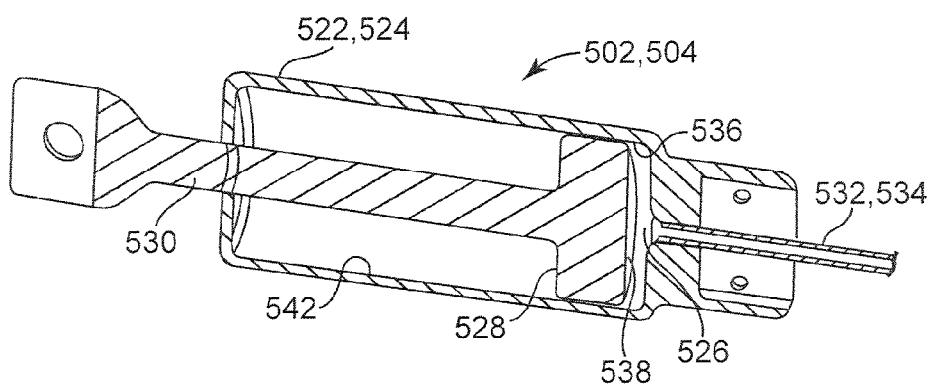
Figure 45:
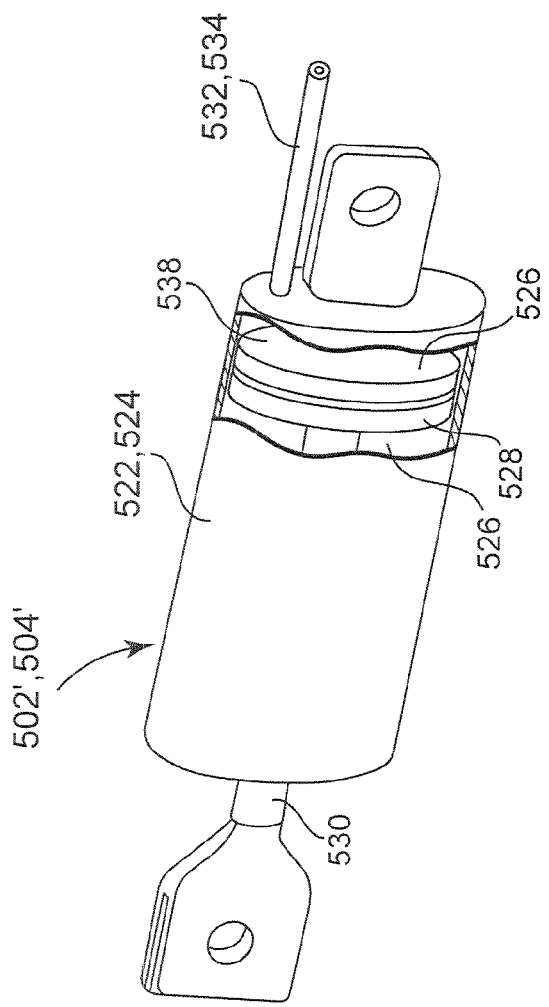
FIG. 45 is a perspective view in partial section of a further single action, hydraulic cylinder, adjustment mechanism adapted to be employed as depicted in FIG. 41 having fluid chamber portions adapted to be filled or be emptied of fluid using a syringe to add or withdraw fluid from subcutaneously implanted fluid reservoirs coupled to the fluid chamber portions to adjust the length of the adjustment spacing between intermediate sling ends in the sling end portions.

In the variation of this embodiment of adjustment mechanism 502, 504 depicted in FIGS. 42-44, the tubes 532 and 534 extend from the end of the housing 522, 524 opposite the rod 530 and centrally along the axes of the mesh 30 of each of the end portions 42 and 44, respectively, to the fluid reservoirs 512 and 514, respectively, to supply fluid to or withdraw fluid from the chamber portion defined by the housing interior wall 536 and the piston head 538. In the variation of adjustment mechanism 502', 504' depicted in FIG. 45, the tube 532, 534 extends offset from the axis of the sling mesh 30.

A dual action hydraulic cylinder form of an adjustment mechanism 552 similar to adjustment mechanisms 502, 504 and 502', 504' is depicted in FIG. 46. An oblong shape of the piston 558, the housing 562, and fluid chamber 556 is also depicted in FIG. 46 that may be substituted for the elliptical shapes of the piston 528, housing 522, 524, and fluid chamber 526, respectively, of FIGS. 42-45.

The dual action adjustment mechanism 552 requires two subcutaneously implantable fluid reservoirs (not shown) or a dual action fluid reservoir and tubes 572 and 574 extending alongside the sling mesh to subcutaneous implantation sites. The housing 562 encloses a fluid chamber 556, piston 558 and rod 560 extending through an opening in one end of the housing 562. The fluid chamber 556 comprises a contracting chamber 568 coupled to tube 572 on one side of piston 558 and an extending chamber 570 coupled to tube 574 on the other side of the piston 558.

In use, the adjustment mechanism 552 is substituted for the adjustment mechanisms 502 and 504 of FIG. 41 to define the adjustment spacings 162 and 164 as a function of the position of the piston 558 in the fluid chamber 556. The adjustment spacing 162, 164 is lengthened if fluid is introduced into chamber portion 570 from the first fluid reservoir through tube 574 while fluid is simultaneously withdrawn from chamber portion 568 into the second fluid reservoir through tube 572. Conversely, adjustment spacing 162, 164 is shortened if fluid is introduced into chamber portion 568 from the second fluid reservoir through tube 572 while fluid is simultaneously withdrawn from chamber portion 570 into the first fluid reservoir through tube 574.

Any of the above-described single action hydraulic adjustment mechanisms can be modified in this fashion to function as a dual action hydraulic adjustment mechanism. It may be desirable to provide a locking mechanism to maintain the adjusted position of the piston and rod of the single or dual action hydraulic adjustment mechanisms disclosed herein after setting the adjustment spacing. Leakage and blow-by of the pressurized hydraulic fluid may occur causing the adjustment spacing to change before tissue ingrowth into the sling mesh pores stabilizes the sling.

FIGS. 47 and 48 illustrate one form of locking mechanism 405 incorporated into a single action hydraulic cylinder adjustment mechanism 402, 404 of the type shown in FIGS. 28-31. In the depicted single action, hydraulic cylinder, adjustment mechanism 402', 404', upper and lower lines of serrations or teeth 421 and 423 extend along the rod 420. The rod 420 extends from the cylinder 455 within housing 422 and passes through a locking ring 425 mounted to slightly rock or pivot on axle 427 supported by the outer housing 415. A counterweight rod 429 also extends from the axle within the outer housing 415. Serrations or teeth are also formed on the inner wall of the locking ring 425 in alignment and engagement with the upper and lower lines of serrations or teeth 421 and 423.

The frictional engagement of the serrations of the locking ring 425 and the upper and lower lines of serrations or teeth 421 and 423 function as the locking mechanism 405 and tend to inhibit movement of the rod 420, but the engagement force is overcome when fluid is added to or removed from the cylinder. The piston and rod 420 can therefore move between its limits due to the change in fluid pressure. If fluid pressure gradually decreases due to leakage, the counterweight rod 429 tends to cause the locking ring 425 to pivot on axle 427 to engage the teeth together to resist movement of the rod 420. It will be understood that the outer housing 415 may extend completely around the locking ring 425 and the housing 422 to isolate them from body tissue.

FIGS. 49 and 50 illustrate another form of locking mechanism 435 incorporated into a single action hydraulic cylinder adjustment mechanism 402, 404 of the type shown in FIGS. 28-31. In the depicted single action hydraulic cylinder adjustment mechanism 402", 404", the locking mechanism 435 comprises modifications to the rod 420 providing reduced diameter sections 437, 439, and a laterally extending pin 441, a pair of springs 447, 449 disposed around rod sections 437, 439, and a rotatable sleeve 457 disposed over the rod 420. The rotatable sleeve 457 surrounding rod 420 extends through the C-shaped opening 417 in housing 415. A spiral slot 451 with a plurality of notches 453 is formed in the rotatable sleeve 457, and the pin 441 extends through the spiral slot 451 and can be engaged in a notch 453.

The adjustment spacing 162, 164 is adjusted by injecting or withdrawing fluid from the fluid chamber to laterally extend or retract the piston mounted rod 420 to increase or decrease the adjustment spacing 162, 164. In the process, rod 420 is moved within cylinder 455 against the spring force of one or the other of the springs 447, 449 and the outwardly extending pin 441 travels along the spiral slot 447, rotating the sleeve 457. The spring force functions as a detent by lodging the pin 441 into engagement with the closest notch 453. The engagement resists any change in rod position that might otherwise occur due to loss of fluid from the cylinder. However, the engagement force can be overcome when fluid is added to or removed from the cylinder. It will be understood that the outer housing 415 may extend completely around the pin 441 and the housing 422 to isolate them from body tissue.

These locking mechanisms may be incorporated into the various single and dual action hydraulic cylinder adjustment mechanisms disclosed herein.

Figure 51:
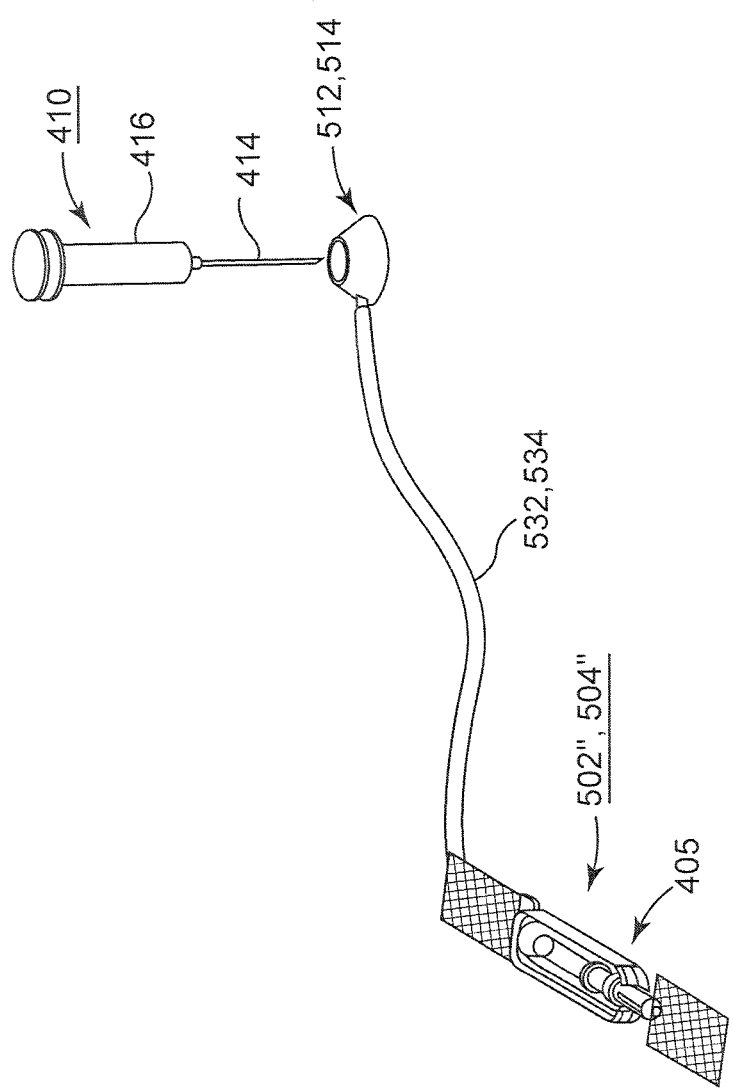
FIG. 51 is a schematic Illustration of a miniaturized, single action, hydraulic cylinder, adjustment mechanism incorporating the locking mechanism illustrated in FIGS. 47 and 48.
Figure 52:
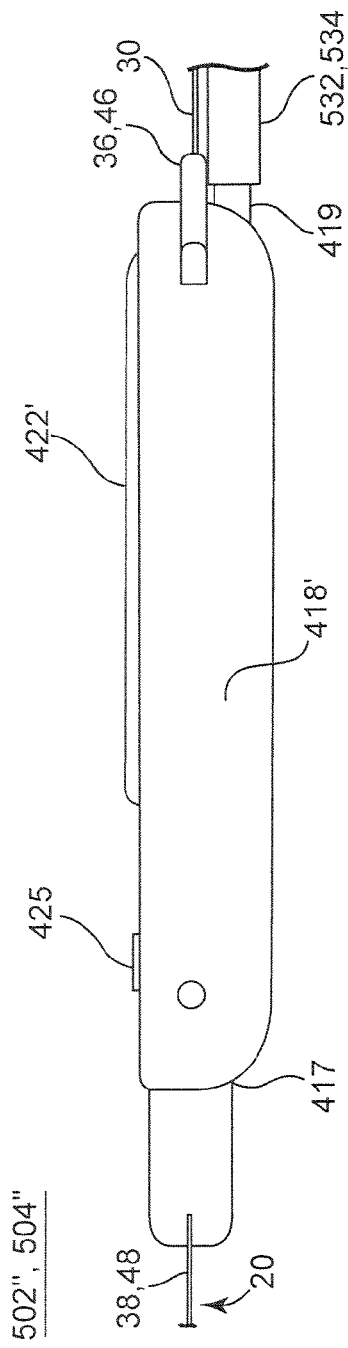
FIG. 52 is a side plan view of the miniaturized, single action, hydraulic cylinder, adjustment mechanism of FIG. 51.
Figure 53:
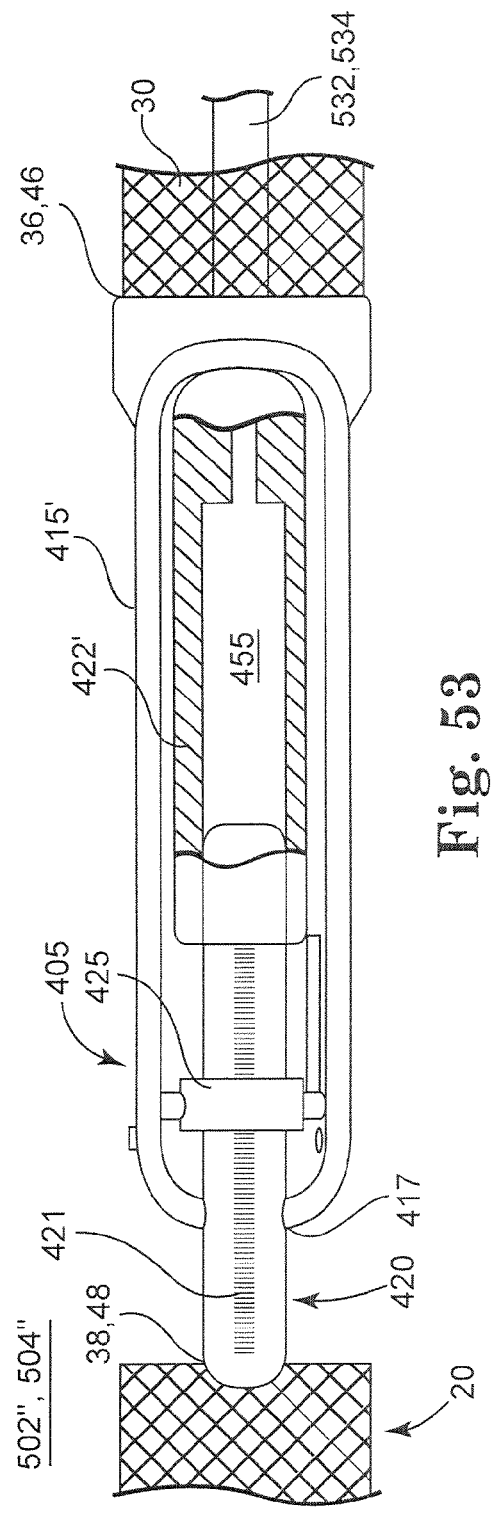
FIG. 53 is a top plan view in partial section of the miniaturized, single action, hydraulic cylinder, adjustment mechanism of FIG. 51.

A further miniaturized single action hydraulic cylinder adjustment mechanism 402", 404" is depicted in FIGS. 51-53 that may be substituted for the above-described adjustment mechanism 502, 504 of FIG. 41. In this embodiment, the width and height or diameter of the modified housing 415' is sized to correspond generally to the width of the sling mesh 30 of sling 20. The locking mechanism 405 described above is incorporated into the modified housing 415' although locking mechanism 435 may be substituted for locking mechanism 405. The cylinder 455 is directly coupled to a tube coupling 419 that the end of the tube 532, 534 is affixed to. The syringe 410 is employed to penetrate the septum of the fill port 512, 514 to add or remove fluid from cylinder 455 and adjust the rod 420 to adjust the adjustable spacing as described above with respect to FIG. 41. As noted above, the tube distal end may be detached from the fluid coupling 419 when tissue ingrowth immobilizes the sling mesh 30. It will be understood that the outer housing 415' may extend completely around the locking ring 425 and the housing 422' to isolate them from body tissue.

The adjustable mechanism of the second aspect of the sling 20 of the present invention may also comprise miniaturized mechanical mechanisms that are adjustable outside the patient's skin or percutaneously through the patient's skin during the healing phase. In certain embodiments the external adjustment actuator comprises an elongated gear drive instrument having a shaft extending between a handle and an engaging end shaped to be percutaneously advanced through the skin. The adjustment mechanism comprises a driven gear means engageable by the engaging end the gear drive for operating the spacing adjustment means to increase or decrease the adjustment spacing.

A miniaturized gear driven adjustment mechanism 802, 804 is depicted in FIGS. 54 and 55 that may be substituted for the above-described adjustment mechanisms 502 and 504 of FIG. 41. An adjustment mechanism housing 822 is attached at one end to the intermediate sling end 36, 46 and encloses a gear chamber 826 and a rod chamber 824. A driven gear 828 is enclosed within the gear chamber 826, and a rod 820 having a spiral thread 834 extending around its circumference extends through the rod chamber 824 and out of housing end opening 832. The spiral thread 834 engages gear threads within the bore of the driven gear 828. One end of the rod 820 is coupled to the intermediate sling end 38, 48.

A gear drive 810 comprises an elongated drive shaft 812 extending through a sheath lumen 814 of a drive sheath 816 to a drive gear 830 within the gear chamber 826 of an outer housing 822. The teeth of the drive gear 830 and the driven gear 828 are in engagement. The drive sheath 816 extends through the skin incisions following implantation to enable adjustment of the length of the rod 820 within the rod chamber 824. The gear drive handle 818 may be grasped and rotated to rotate the drive shaft 812 and the drive gear 830. Rotation of the driven gear 828 around the rod 820 in one direction drives the rod 820 out of the rod chamber 824 and lengthens the adjustment spacing 164, 166, whereas rotation of the driven gear 828 around the rod 820 in the other direction drives the rod 820 into the rod chamber 824 and shortens the adjustment spacing 164, 166.

The distal end of drive shaft 812 may be shaped to detachably engage axially with the drive gear 830 so that the drive sheath 816 and shaft 812 may be axially pulled upon from their proximal ends outside the skin to detach from the housing 822 and drive gear 830, respectively, and be drawn out through the skin incision after tissue ingrowth into the mesh pores has secured the sling 20 in position.

Figure 56:
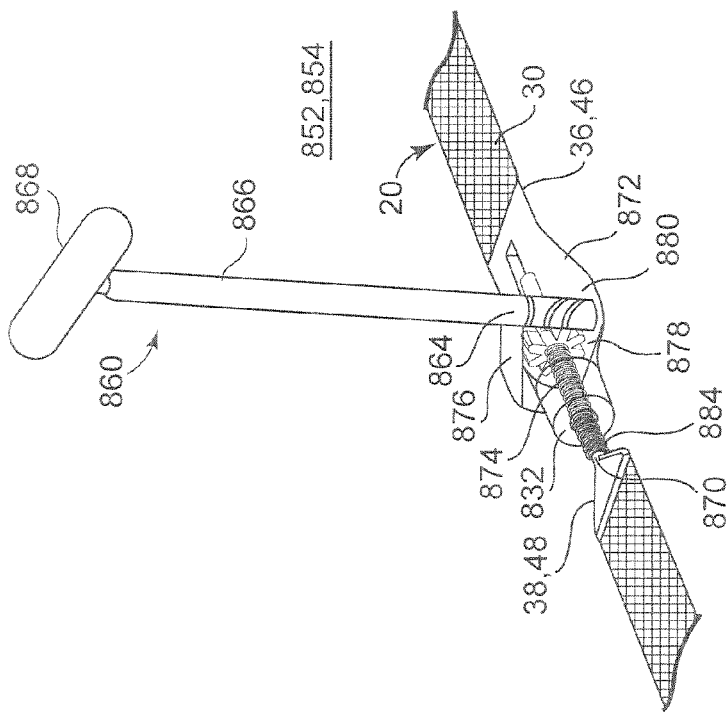
FIG. 56 is a schematic Illustration of a further miniaturized, mechanical gear, adjustment mechanism that is adjusted by a gear drive external adjustment actuator extended percutaneously through the patient's skin to engage the gear drive and adjust sling tension.

An alternative, miniaturized, gear driven adjustment mechanism 852, 854 is depicted in FIG. 56 that may be substituted for the above-described adjustment mechanisms 302 and 304 of FIG. 18. An adjustment mechanism housing 872 is attached at one end to the intermediate sling end 36, 46 and encloses a gear chamber 876 and a rod chamber 874. A driven gear 878 is enclosed within the gear chamber 876, and a rod 870 having a spiral thread 884 extending around its circumference extends through the rod chamber 874 and out of housing end opening 832. The spiral thread 884 engages gear threads within the bore of the driven gear 878. One end of the rod 870 is coupled to the intermediate sling end 38, 48.

A gear driver 860 comprises an elongated drive shaft 866 having a spiral drive gear 880 at the distal end of the drive shaft 866 and a handle 868 at the proximal end of the drive shaft 866. The distal end of the gear drive 860 may be shaped to be percutaneously advanced through the patient's intact skin at pre-made incisions to interact with the driven gear 878. The distal end of the drive shaft 866 is extended through an opening in the housing 872 and into engagement with the drive gear 880 to adjust of the length of the rod 870 within the rod chamber 874. The teeth of the drive gear 880 and the driven gear 878 are depicted in engagement in FIG. 56. The gear drive handle 868 may be grasped and rotated to rotate the drive shaft 866 and the drive gear 880. Rotation of the driven gear 878 around the rod 870 in one direction drives the rod 870 out of the rod chamber 874 and lengthens the adjustment spacing 164, 166, whereas rotation of the driven gear 878 around the rod 870 in the other direction drives the rod 870 into the rod chamber 874 and shortens the adjustment spacing 164, 166.

It will be understood that alternatively, the gear drive may take the form of gear drive 810 of FIG. 54 that is temporarily left extending through the skin incisions following implantation of the sling. In that case, the distal end of drive shaft 812 may be shaped to detachably engage axially with the drive gear 880 so that the drive sheath 816 and shaft 812 may be axially pulled upon from their proximal ends outside the skin to detach from the housing 872 and drive gear 880, respectively, and be drawn out through the skin incision after tissue ingrowth into the mesh pores has secured the sling 20 in position.

Figure 57:
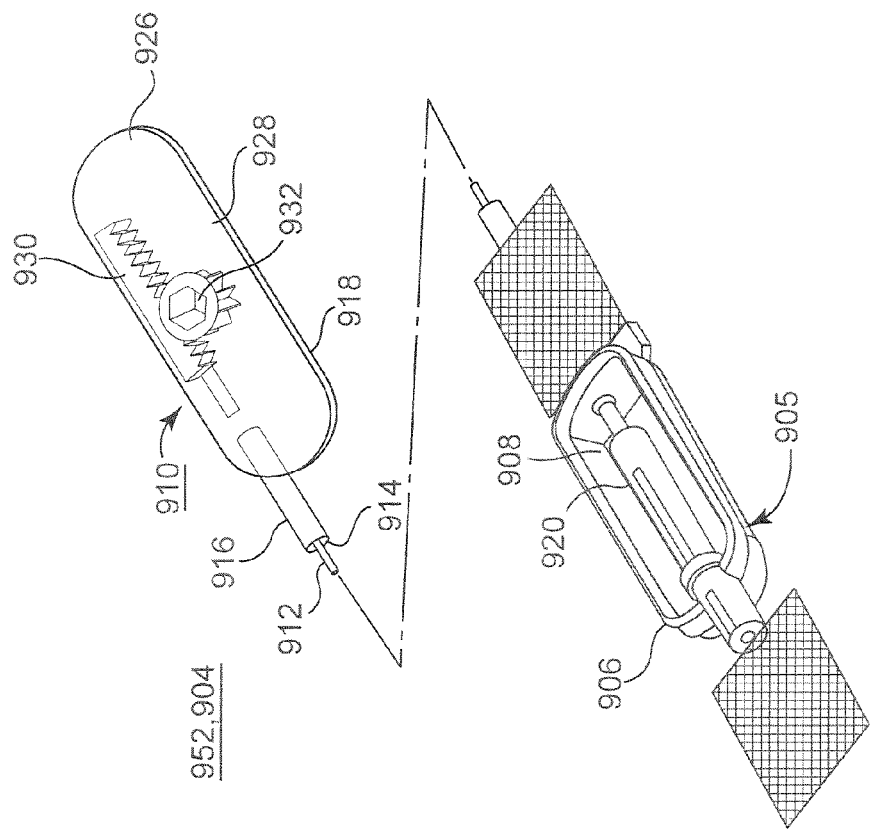
FIG. 57 is a schematic Illustration of a still further miniaturized, mechanical gear, adjustment mechanism that is adjusted by a rack and pinion gear drive extended temporarily through the patient's skin.

A still further alternative, miniaturized, mechanical drive mechanism 902, 904 is depicted in FIG. 57 that may be substituted for the above-described adjustment mechanisms 502 and 504 of FIG. 41. In this embodiment, the adjustment spacing 164, 166 is adjusted by a rack and pinion gear drive 910 extended temporarily through the patient's skin or implanted under the patient's skin and accessed percutaneously with an external adjustment actuator 310 shaped to engage the pinion gear drive 910 similar to external adjustment actuator 310 shown in FIG. 18.

In the embodiment depicted in FIG. 57, the gear drive 910 comprises an elongated drive shaft 912 extending through a sheath lumen 914 of a drive sheath 916 from a gear drive housing 918 to the mechanical drive mechanism 902, 904. The proximal end of the sheath 916 is coupled to the gear drive housing 918. The gear drive housing 918 encloses a gear chamber 926 in which a rack 930, coupled at one end to the proximal end of the drive shaft 912, is disposed for lateral movement, and a pinion 928 is positioned for rotary movement. The teeth of the rack 930 and the pinion 928 are in engagement. A hex shaped recess 932 is formed in the pinion to be engaged by a hex wrench to rotate the pinion 928 and laterally move the rack 930 within the gear chamber 926.

The distal ends of the sheath 916 and the drive shaft 912 are coupled to one end of the housing 906 of the drive mechanism 902, 904. The housing 906 takes the form of the housing 415' of FIGS. 51-53 and is depicted without a cover to expose the rod chamber 908 and the rod 920 and locking mechanism 905 disposed therein. Locking mechanism 905 corresponds to locking mechanism 405 described above and may take other forms or may not be provided in this embodiment.

Rotation of the pinion 928 in one direction drives the rack 930 and the drive shaft 912 in one direction to drive rod 920 out of the rod chamber 908 and lengthen the adjustment spacing 164, 166. Rotation of the pinion 928 in the other direction drives the rack 930 and the drive shaft 912 in the other direction to pull rod 920 into the rod chamber 908 and shortens the adjustment spacing 164, 166.

A still further alternative, miniaturized, mechanical drive mechanism 952, 954 is depicted in FIGS. 58A-58D that may be substituted for the above-described adjustment mechanisms 502 and 504 of FIG. 41. In this embodiment, the adjustment spacing 164, 166 is also adjusted by a rack and pinion gear drive 910 extended temporarily through the patient's skin or implanted under the patient's skin and accessed percutaneously with an external adjustment actuator 310 shaped to engage the rack and pinion gear drive 910 as described above with respect to FIG. 57.

In this embodiment, the housing 956 is coupled at one end to the sling intermediate end 36, 46, and encloses a rack chamber 958 and a driven rack 962 within the rack chamber 958. The driven rack 962 in rack chamber 958 is coupled at one rack end to the end of the drive shaft 914 and at the other rack end to the sling intermediate end 38, 48. A pivotally mounted catch 964 is shaped to engage rack teeth 962 and to guide movement and help maintain rack 960 in a selected position in the rack chamber 958 to define the adjustment spacing 162, 164.

Figure 58A:
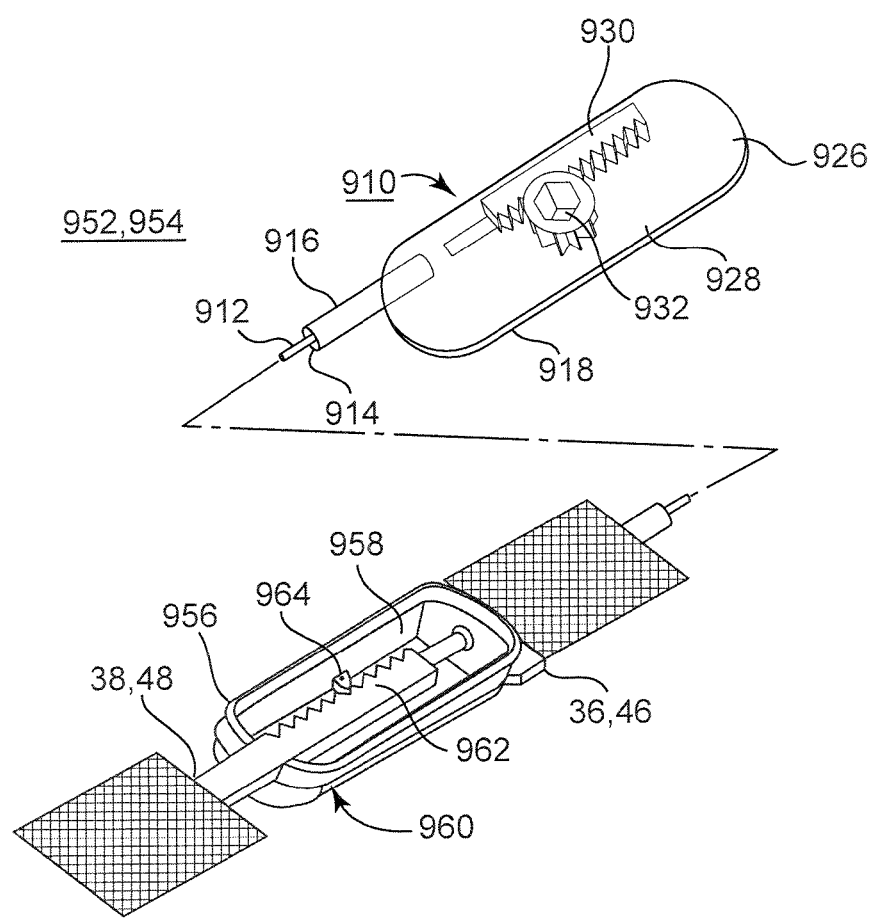
FIGS. 58A-58D are schematic views in partial section illustrating adjustment of sling tension through use of the rack and pinion gear drive extended temporarily through the patient's skin to adjust the miniaturized, mechanical gear, adjustment mechanism of FIG. 57.
Figure 58B:
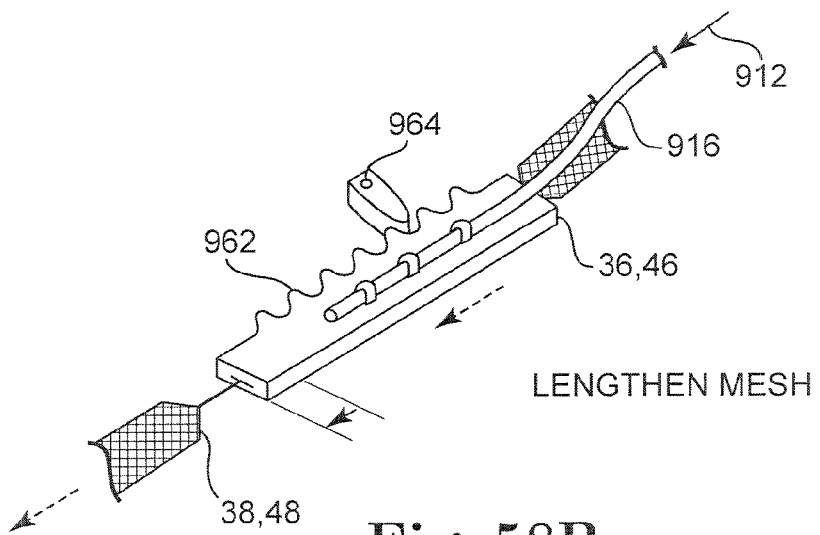
Figure 58C:
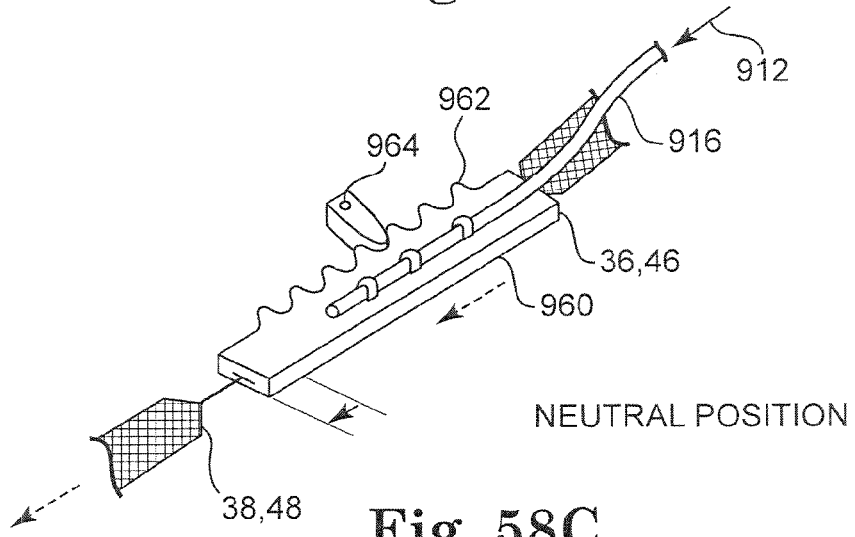
Figure 58D:
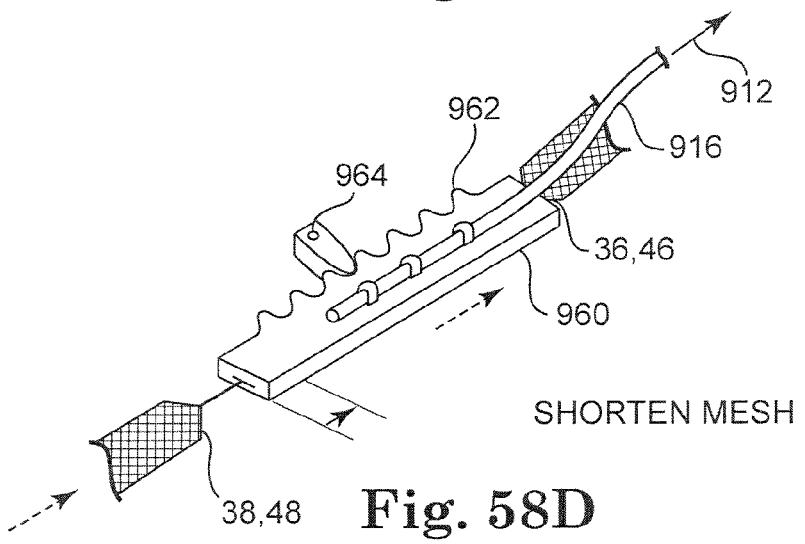

Rotation of the pinion 928 in one direction drives the drive rack 930 and the drive shaft 912 in one direction to move drive rack 962 out of the rack chamber 958 and lengthen the adjustment spacing 164, 166 as shown in FIG. 58B. Rotation of the pinion 928 in the other direction moves the rack 930 and the drive shaft 912 in the other direction to pull rod 920 into the rack chamber 958 and shortens the adjustment spacing 164, 166, as shown in FIG. 58D.

It will be understood that the gear drive housing 918 can be implanted under the skin. It will also be understood that each gear drive housing 918 can be temporarily left extending through the skin incisions following implantation of the sling. In this case, the distal end of drive shaft 912 may be shaped to detachably engage axially with the rod 920, and the distal end of the sheath 916 may detachably engage with the end of the housing 906 or 956. After tissue ingrowth into the mesh pores has secured the sling 20 in position, the drive sheath 916 and shaft 912 may be axially pulled upon from their proximal ends outside the skin to detach from the housing 906 or 956 and rod 920 or rack 960, respectively, and be drawn out through the skin incision.

With respect to the embodiment of FIGS. 58A-58D, it will be understood that the drive pinion 928 can alternatively be integrated into the rack chamber 958 in lieu of or alongside the pivoting catch 964. In this variation, the gear drive 910, sheath 916, and the shaft 912 would be eliminated, and the pinion 928 located if the rack chamber 958 could be accessed by the percutaneously inserted hex wrench 310 in the manner described above with respect to FIGS. 18-23.

It will be understood that the above-described embodiments of the second category of the sling of the invention may be modified by substituting other support materials than open pore mesh 30, particularly in the central support portion 40, e.g., homograft or allograft materials or nonporous synthetic materials. Moreover, other materials and structures may be substituted for the mesh 30 in the sections of constituting one or both of the end portions extending from the intermediate ends 38 and 48 to the ends of the central support portion 40. For example, one or more straight or spiral suture may be substituted for all or part of such sections.

While the above-described embodiments of adjustable tension slings depict methods and apparatus for adjusting sling tension in each end portion, it will be understood that in each case only one adjustment mechanism may be provided acting on or within one sling end portion (or alternatively on both end portions 1).

It will also be understood that all of the above-described embodiments of the urethral or fecal slings may optionally incorporate a sling central portion adjustment mechanism, e.g., suture 108 illustrated in FIGS. 10 and 11 or as otherwise described herein.

Furthermore, it will be understood that all of the above-described embodiments of the urethral or fecal slings illustrated in FIGS. 12 through 58 may optionally incorporate tissue anchors coupled to the sling ends extending from or incorporated into the sling ends 32 and 34. For example the sling anchor 92 illustrated extending from sling end 32 in FIG. 11 could be incorporated into a suture extending from the sling ends 32 and 34 in each such embodiment to assist in tensioning the sling end portions 42 and 44 during adjustment of the tension adjustment mechanisms.

Many of the embodiments described herein can be used in connection with prolapse and pelvic floor repairs (men and women) that may require post-operative adjustment of the implanted mesh or graft or sling. They may also be used in connection with prostatectomies or hysterectomies and to support any other body tissue within the pelvic area or other parts of the body including but not limited to, hernia repair, and shoulder and abdominal repairs. Examples of meshes, grafts and prolapse repairs are described in U.S. Publication Nos. 2004-0039453 A1, 2005-0250977 A1, and 2005-0245787 A1, which are hereby incorporated by reference in their entirety.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical surgical procedures that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A system for providing support to body tissue to alleviate incontinence, comprising:

an elongated incontinence sling having a central support portion adapted to be positioned to support any one of the urethra or anus, the elongated incontinence sling having first and second sling end portions extending from the central support portion through body tissue;

a tension adjustment mechanism acting on or within one or both of the sling end portions, wherein the tension adjustment mechanism is attached to and extends through an adjustment spacing intermediate the first sling end portion and the central support portion and includes a drive mechanism provided in a housing and having a rack device, the rack device having a plurality of teeth and a non-rotating catch engageable with the plurality of teeth, with an external portion of the rack extending out of the housing and operatively connected to the first sling end portion;

wherein the non-rotating catch is a pivotable non-rotating catch that engages with the plurality of teeth in response to linear movement of the plurality of teeth; and an external adjustment actuator that operatively engages with the tension adjustment mechanism and selectively changes the adjustment spacing such that extension of the external portion of the rack out of the housing lengthens the adjustment spacing and withdrawing the external portion of the rack into the housing shortens the adjustment spacing to thereby change tension in the central support portion applied to the urethra or anus.

2. The system of claim 1, wherein the external adjustment actuator is adapted to extend through the patient's skin for adjustment.

3. The system of claim 1, further comprising at least one tissue anchor coupled to at least one of the first and second sling end portions and adapted to be passed through body tissue to anchor against the body tissue.

4. The system of claim 1, wherein:
the external adjustment actuator comprises an elongated instrument having a shaft extending between a handle and an engaging end, the external adjustment actuator shaped to be percutaneously advanced through the skin.

5. The system of claim 1, wherein the housing includes a generally hexagonal-shaped recess adapted to receive the external adjustment actuator.

6. The system of claim 1, wherein the mechanism includes a drive shaft operatively connected with the central support portion.

7. The system of claim 1, wherein at least the central support portion is constructed of a mesh material.

8. The system of claim 1, wherein the elongated incontinence sling is constructed of a mesh material.

9. The system of claim 1, wherein the external adjustment actuator is a hex wrench.

10. The system of claim 1, further including a drive sheath operatively connected with the first sling end portion.

* * * * *

UNITED STATES PATENT AND TRADEMARK OFFICE
CERTIFICATE OF CORRECTION

PATENT NO. : 8,460,169 B2  
APPLICATION NO. : 12/305874  
DATED : June 11, 2013  
INVENTOR(S) : Lund et al.

Page 1 of 2

It is certified that error appears in the above-identified patent and that said Letters Patent is hereby corrected as shown below:

On the Title Page

On Page 5, Item (56), under "OTHER PUBLICATIONS", in Column 1, Line 7, delete "Europeon" and insert -- European --, therefor.

On Page 5, Item (56), under "OTHER PUBLICATIONS", in Column 2, Line 34, delete "Incontintence," and insert -- Incontinence, --, therefor; Column 2, Line 36, delete "Magentic" and insert -- Magnetic --, therefor; Column 2, Line 45, delete "Incontience," and insert -- Incontinence, --, therefor; Column 2, Line 56, delete "Cirriculum Vitae," and insert -- Curriculum Vitae, --, therefor; Column 2, Line 69, delete "Uroloyg," and insert -- Urology, --, therefor.

On Page 6, Item (56), under "OTHER PUBLICATIONS", in Column 1, Line 1, delete "L'Interpostion" and insert -- L'Interposition --, therefor.

On Page 6, Item (56), under "OTHER PUBLICATIONS", in Column 2, Line 10, delete "Advaned" and insert -- Advanced --, therefor; Column 2, Line 30, delete "Therory" and insert -- Theory --, therefor; Column 2, Line 64, delete "Appliations" and insert -- Applications --, therefor; Column 2, Line 65, delete "Sling Pklasty" and insert -- Slingplasty --, therefor.

On Page 7, Item (56), under "OTHER PUBLICATIONS", in Column 1, Line 58, delete "Dystfunction," and insert -- Dysfunction, --, therefor.

On Page 7, Item (56), under "OTHER PUBLICATIONS", in Column 2, Line 10, delete "Deptment" and insert -- Department --, therefor; Column 2, Line 23, delete "Infacoccygeal" and insert -- Infracoccygeal --, therefor.

On Page 8, Item (56), under "OTHER PUBLICATIONS", in Column 1, Line 14, delete "Suspenison," and insert -- Suspension, --, therefor; Column 1, Line 19, delete "Gynécolgie" and insert -- Gynécologie --, therefor.

Signed and Sealed this  
Twenty-first Day of October, 2014

Michelle K. Lee  
*Deputy Director of the United States Patent and Trademark Office*

CERTIFICATE OF CORRECTION (continued)
U.S. Pat. No. 8,460,169 B2

On Page 8, Item (56), under "OTHER PUBLICATIONS", in Column 2, Line 16, delete "fcr" and insert -- for --, therefor.

In the Specification

In Column 2, Line 27, delete "uethra" and insert -- urethra --, therefor.

In Column 9, Line 54, delete "proplapse" and insert -- prolapse --, therefor.

In Column 10, Line 58, delete "procine" and insert -- porcine --, therefor.

In Column 12, Line 28, delete "suture" and insert -- sling --, therefor.

In Column 15, Line 46, delete "released" and insert -- release --, therefor.

In Column 19, Line 39, delete "syringe" and insert -- syringe 410 --, therefor; Column 19, Lines 41-42, delete "chamber." and insert -- chamber 416. --, therefor.

In the Claims

Column 28, Line 9, in Claim 6, delete "the mechanism" and insert -- the drive mechanism --, therefor.